(12) United States Patent
Grubbs et al.

(10) Patent No.: US 10,765,777 B2
(45) Date of Patent: Sep. 8, 2020

(54) LIGHT ADJUSTABLE INTRAOCULAR LENSES USING UPCONVERTING CORE-SHELL NANOPARTICLES AND NEAR INFRARED (NIR) LIGHT

(71) Applicant: California Institute of Technology, Pasadena, CA (US)

(72) Inventors: Robert H. Grubbs, South Pasadena, CA (US); Christopher B. Marotta, Valley Village, CA (US)

(73) Assignee: California Institute of Technology, Pasadena, CA (US)

( * ) Notice: Subject to any disclaimer, the term of this patent is extended or adjusted under 35 U.S.C. 154(b) by 85 days.

(21) Appl. No.: 16/020,196

(22) Filed: Jun. 27, 2018

(65) Prior Publication Data

US 2019/0001024 A1    Jan. 3, 2019

Related U.S. Application Data

(60) Provisional application No. 62/526,186, filed on Jun. 28, 2017.

(51) Int. Cl.
 *A61F 2/16*    (2006.01)
 *A61L 27/44*   (2006.01)
 (Continued)

(52) U.S. Cl.
 CPC ............ *A61L 27/44* (2013.01); *A61F 2/1627* (2013.01); *A61F 2/1635* (2013.01); *A61F 2/1659* (2013.01); *A61L 27/047* (2013.01); *A61L 27/14* (2013.01); *A61L 27/26* (2013.01); *A61L 27/446* (2013.01); *A61L 27/52* (2013.01); *A61F 2002/16965* (2015.04); *A61L 2400/12* (2013.01); *A61L 2430/16* (2013.01)

(58) Field of Classification Search
 CPC ........ A61L 27/44; A61L 27/047; A61L 27/14; A61L 27/26; A61L 27/446; A61L 27/52; A61L 2400/12; A61L 2430/16; A61F 2/1627; A61F 2/1635; A61F 2/1659
 See application file for complete search history.

(56) References Cited

U.S. PATENT DOCUMENTS

| | | | |
|---|---|---|---|
| 6,387,379 B1 | 5/2002 | Goldberg et al. |
| 7,727,544 B2 | 6/2010 | Schwartz et al. |

(Continued)

FOREIGN PATENT DOCUMENTS

| | | |
|---|---|---|
| EP | 1882463 A1 | 1/2008 |
| KR | 10-2016-0079154 A | 7/2016 |

OTHER PUBLICATIONS

Zhou et al., "Upconversion nanophosphors for small-animal imaging", Chemical Society Re ews,2012,41, 1323-1349.

(Continued)

*Primary Examiner* — David H Willse
*Assistant Examiner* — Tiffany P Shipmon
(74) *Attorney, Agent, or Firm* — BakerHostetler

(57) ABSTRACT

This disclosure relates compositions comprising upconverting core-shell nanocrystals and photoactive compositions and methods using these compositions to modify treat myopia and other ocular conditions. In some cases, the methods use near infrared irradiation to adjust the refractive power of light adjustable intraocular lenses.

25 Claims, 27 Drawing Sheets
(11 of 27 Drawing Sheet(s) Filed in Color)

(51) Int. Cl.
A61L 27/52 (2006.01)
A61L 27/04 (2006.01)
A61L 27/14 (2006.01)
A61L 27/26 (2006.01)

(56) References Cited

U.S. PATENT DOCUMENTS

| | | | |
|---|---|---|---|
| 8,414,911 B2 | 4/2013 | Mattson et al. | |
| 9,895,467 B2 | 2/2018 | Grubbs et al. | |
| 2005/0027031 A1 | 2/2005 | Chang et al. | |
| 2007/0055369 A1 | 3/2007 | Grubbs et al. | |
| 2011/0171320 A1* | 7/2011 | Dantus | A61K 9/0048 424/617 |
| 2012/0089180 A1* | 4/2012 | Fathi | B41J 2/17559 606/214 |
| 2013/0278989 A1 | 10/2013 | Lam et al. | |
| 2013/0323685 A1* | 12/2013 | Ostler | A61K 6/887 433/228.1 |
| 2014/0148880 A1 | 5/2014 | Deisseroth et al. | |
| 2016/0331868 A1 | 11/2016 | Grubbs et al. | |
| 2017/0020658 A1 | 1/2017 | Grubbs et al. | |

OTHER PUBLICATIONS

Yagci et al., "Photoinitiated Polymerization: Advances, Challenges, and Opportunities", Macromolecules, 2010, 43, 6245-6260.
Wang et al., "Upconversion nanoparticles in biological labeling, imaging, and therapy", Analyst, 2010, 135, 1839-1854.
Sun et al., "Upconversion of Rare Earth Nanomaterials", Annual Reviews Physical Chemistry, Feb. 2015, 66, 619-642.
Seidmeier, A., et al., Chem Soc Rev., 2015, 44, 1526-1560.
Sedlmeier et al., "Surface modification and characterization of photon-upconverting nanoparticles for bioanalytical applications", Chemical Society Reviews, 2015, 44, 1526-1560.
Resch-Genger et al., "Quantum dots versus organic dyes as fluorescent labels", Nature Methods, Aug. 2008, 5, 763-775.
Li, et al., Nanotechnology 2008, 19, 345606, 1-5.
Li et al., "Lab on upconversion nanoparticles: optical properties and applications engineering via designed nanostructure", Chemical Society Reviews, 2015, 44, 1346-1378.
Li et al., "An efficient and user-friendly method for the synthesis of hexagonal-phaseNaYF4:Yb, Er/Tm nanocrystals with controllable shape and upconversion fluorescence", Nanotechnology, Jul. 2008, 19, 345606. 5 pages.
Kramer et al., "Hexagon Sodium Yttrium Fluoride Based Green and Blue Emitting Upconversion Phosphors", Chemistry of Materials, 2004, 16, 1244-1251.
Jacques, "Corrigendum: Optical properties of biological tissues: a review", Physics in Medicine and Biology, Jun. 2013, 58, R37-R61.
Haase et al., "Upconverting Nanoparticles", Angewandte Chemie International Edition, May 2011, 50, 5808-5829.
Deng, R. et al., Nat. Nanotech, 2015, 10, 237-242.
Bunzli et al., "Taking advantage of luminescent lanthanide ions", Chemical Society Reviews, Jun. 2005, 34, 1048-1077.
Boyer, J.C. et al., J. Am. Chem. Soc. 128, 7444-7445.
Boyer et al., "Synthesis of Colloidal Upconverting NaYF4 Nanocrystals Doped with Er3+, Yb3+ and Tm3+ via Thermal Decomposition of Lanthanide Trifluoroacetate Precursors", Journal of the American Chemical Society, May 2006, 128, 23, 7444-7445.
Auzel, "Upconversion and Anti-Strokes Processes with f and d Ions in Solids", Chemical Reviews, 2004, 104, 139-173.

* cited by examiner $NaGdF_4:Yb/Tm$  $Yb^{3+}$ $NaGdF_4:A$  $Tm^{3+}$ $NaYF_4$  $Gd^{3+}$ Quencher  $A^{3+}$ "Hydroxy-tButylEster-PEG"
(HBP)

Yield = 27%

NaY:Yb:Tm(75:25:0.03)F$_4$@NaYb:Y(9:1)F$_4$@NaNd:Y(9:1)F$_4$@NaYF$_4$

*Oleic Acid Capped*

*SiO$_2$ Capped*

NaYbF$_4$:Tm,Nd(1%,1%)@NaYF$_4$

NaYbF$_4$:Tm(1%)@NaYbF$_4$:Nd(40%)@CaF$_2$

NaY:Yb:Tm(19:80:1)F$_4$@NaY:Yb:Nd(40:10:50)F$_4$@CaF$_2$

NaYF$_4$@NaYbF$_4$:Tm(1%)@NaYF$_4$

LIGHT ADJUSTABLE INTRAOCULAR LENSES USING UPCONVERTING CORE-SHELL NANOPARTICLES AND NEAR INFRARED (NIR) LIGHT

CROSS REFERENCE TO RELATED APPLICATIONS

This application claims the benefit of priority to U.S. Application Ser. No. 62/526,186, filed Jun. 28, 2017, the contents of which are incorporated by reference herein in their entirety for all purposes.

TECHNICAL FIELD

This invention relates compositions, including light adjusting lenses, and procedures to modify these compositions. In some cases, the methods use near infrared irradiation to adjust the refractive power of light adjustable ocular lenses.

BACKGROUND

A light adjustable lens is an optical device whose refractive properties can be changed after its fabrication and insertion into a human eye. Light adjustable lenses can have a refraction modulating composition dispersed in a polymer matrix. After the lens has been implanted into the eye and refractive stabilization has occurred, the preexisting optical aberrations or those induced by the surgical procedure are measured. In order to correct these optical aberrations (e.g., spherical power, astigmatism, spherical aberration, etc.), a corresponding amount of UV-Vis radiation is applied to the light adjustable lens, which alters the optical properties of the lens either through changes in its shape, its index of refraction, or both. Following one or several irradiations in which portions of the lens have been exposed to selectively and spatially modify the refractive power, the entire lens is irradiated to "lock in" the modified lens.

Prior work describes the use of UV irradiation (320-400 nm) for post-operative power adjustment of light adjustable lenses. For example, a Helium Cadmium (HeCd) laser operating at 325 nm and a mercury (Hg) arc lamp spectrally filtered for the emission lines at 334 and 365 nm have been used for modifying the refractive power of light adjustable lenses. Additionally, the prior work also mentions tripled frequency laser diode pumped solid state YAG laser operating at 355 nm, an argon ion laser operating in between 350-360 nm, a deuterium discharge lamp, and broad band xenon:mercury lamps operating with any narrow band spectral filter are useful sources for conducting UV irradiation tests on light adjustable materials and lenses.

However, there are potential safety issues related to each of these sources. Coherent sources (e.g., lasers) are narrowly focused and have high irradiances that can cause permanent damage to retinal tissues. In addition, such sources must be rasterized across the lens requiring complex control of the beam and increased cost. Extended or more diffuse, incoherent sources such as arc lamps offer a more attractive solution from the standpoint of economic (cost and availability) and safety concerns (coherent vs. non-coherent) but they must be attenuated by as much as a factor of 1000 for use in irradiating the light adjustable lenses. Thus, improper use of the lamp, mechanical, or electrical failure could result in applying high irradiances and radiant exposures to the ocular structures causing damage. Taken together, there remains a need in the art for methods to modify the lens so as to increase the achieved power change, reduce the dose required for lock-in, and improve the retinal safety profile of the procedure.

U.S. Pat. No. 9,895,467 discloses the use of upconverting nanocrystals for use in intraocular lenses. While this use provides substantial benefits, there still remains room for improvement. For example, while single crystal upcconverting nanoparticles described therein to emit at wavelengths suitable for activating the photoinitiators described therein, these emissions tend to be weak, resulting in low quantum yields. The present disclosure addresses these and other concerns.

SUMMARY

The present invention is directed to optical hydrogels, whose shape and/or refractive indices can be catalyzed by the application of light, methods of preparing the same, and optical devices and lenses derived therefrom. Further, the invention relates to optical devices, especially intraocular lenses, whose refractive indices can be changed by an external light source after the healing process associated with implantation of the lens(es) is complete. The lens is stable until a pattern of light of the proper wavelength is used to change the power of the lens. Still further, in some embodiments, the optical hydrogels and/or the intraocular lenses comprise core-shell upconverting nanoparticles or nanocrystals that allow the use of near infrared light to effect the changes with appropriate photoactivators.

Certain embodiments provide optical hydrogels or optical devices, including light adjustable intraocular lenses comprising:
 (a) a photopolymerizable prepolymer;
 (b) a UV-Vis photoinitiator;
 (c) at least one upconverting core-shell nanocrystal; and
 (d) optionally a UV-Vis blocker;
wherein the optical hydrogel or optical device, including light adjustable intraocular lens further optionally comprises a polymer matrix in which the photopolymerizable prepolymer material, the UV-Vis photoinitiator, the optional UV-Vis blocker, and the at least one upconverting nanocrystal are distributed. For its suited purpose, the optical hydrogel or optical device, including light adjustable intraocular lens is transparent or practically transparent.

Where present, the polymer matrix provides the structure for the intraocular lens. It is typically based on (meth)acrylate chemistry which can be hydrophobic or hydrophilic. The photopolymerizable prepolymer may comprise a polyethylene glycol (PEG), a poly[alkyl or dialkyl]siloxane, a poly[meth]acrylate, a poly(amino acid), a poly(amino acid)-copolymer, a polycarbohydrate, a protein, or a polysaccharide backbone, for example comprising an acrylate, methacrylate, acrylamide, methacrylamide, allyloxy, cinnamoyl, or vinyl group.

In certain embodiments, the photoinitator is a chemical or material that absorbs light in a range of from 250 nm to 600 nm. In some cases, the photoinitiator absorbs light in a range of from 300 nm to 450 nm ("blue range", preferably 360 nm to 370 nm) and/or in a range of from 450 nm to 600 nm ("red range").

The present disclosure highlights those light adjustable intraocular lenses comprising at least one type of upconverting core-shell nanocrystal comprising:
 (a) a nanocrystalline core comprising a lanthanide sensitizer capable of absorbing light in a range of from 780 nm to 1020 nm and having at least one emission peak in the range of from 250 nm to 500 nm;

(b) at least one activating shell superposed on the nanocrystalline core, the shell comprising at least one lanthanide activator; and (c) an optionally an optically inert outer layer superposed over the at least one activating shell. The at least one type of upconverting core-shell nanocrystal is capable of absorbing light in the near infrared region and emitting it in the visible region, thereby activating the photosensitizer for polymerizing the prepolymer material(s). In preferred embodiments, the upconverting core-shell nanocrystal emits a wavelength of light that "matches" the absorption maximum of the photosensitizer. Typically, the nanocrystalline core comprises one or more of Er, Fe, Gd, Ho, Tm, Y, or Yb. Within this genus, the nanocrystalline core typically comprises Y and/or at least one of Tm, Er, Fe, or combination thereof. Exemplary cores comprise a $NaGdF_4$, $NaLuF_4$, $LiYF_4$, $NaYF_4$, $KYF_4$, $KYb_2F_7$, $BaF_2$, $CaF_2$, $SrF_2$, $LaF_3$, $YF_3$, $BaYF_5$, $BaGdF_5$, $KY_3F_{10}$, YOF, LuOF, or GdOF host doped with one or more of Er, Fe, Gd, Ho, Tm, Y, or Yb. A more specific example includes a host doped with one or more of (i) Er or Tm and (ii) Yb ($NaYF_4$:Yb, Er/Tm).

In some embodiments, the core-shell nanocrystal comprises an optically inert outer layer that may comprise yttrium, a $C_{6-24}$ saturated or unsaturated fatty acid, an optionally functionalized silicate polymer coating (e.g., mesoporous silica), or a alkali metal fluoride or alkaline earth metal fluoride (e.g., $CaF_2$). This inert outer layer may also further provide functionalization (e.g., di- or polyfunctionalized organic moieties, such as di- or polycarboxylic acids) to link the photoiniator to nanoparticle surface for more effective photochemical interaction.

In still further embodiments, the optical hydrogel, optical device, or light adjustable intraocular lens may further comprising the UV-Vis blocker, such as a benzotriazole compound. When present as an intraocular lens, the structure may further comprise one or both of an IR blocking back layer for light adjustable lens, thereby reducing potential retinal exposure to incident beam and/or a UV blocking front and/or back layer for light adjustable lens, thereby reducing potential retinal exposure to upconverted radiation, emitted by upconverting core-shell nanoparticles.

This disclosure also includes embodiments for methods for adjusting the optical properties of the intraocular lenses described herein.

In certain embodiments, the method of adjusting the optical properties of the light adjustable intraocular lenses described herein comprise irradiating the light adjustable intraocular lens with a near infrared wavelength of light, wherein the irradiation of the light adjustable lens results in a change in a refractive property of the light adjustable intraocular lens. The source of near infrared light may be a laser, having a power consistent with biological exposure limits. The laser may be operating in pulsed mode with defined pulse lengths. In some cases, the laser powers and pulses are selected to improve the relative intensity of the peaks associated with the absorbances of the photosensitizers relative to other optical regions. For example, the near infrared wavelength of light may be applied in a range of from 780 nm to 1020 nm and at a power in a range of from 1 $W/cm^2$ to 5 $W/cm^2$, preferably 1-2.5 $W/cm^2$, and/or using pulses with length less than 6 ms, less than 2 ms, less than 1 ms, less than 500 microsec, and less than 200 microsec. The specific wavelength of irradiation depends on the specific upconverting core-shell nanoparticle composition. Typically, the irradiation is provided after the light adjustable intraocular lens is implanted in an eye of a patient.

The present disclosure is directed to compositions, including light adjustable intraocular lenses, and methods of providing and correcting such lenses inserted into an eye of a patient, methods of altering the refractive properties of these lenses, for example by in situ polymerization or crosslinking of the compositions, and the compositions which allow for these methods.

Certain specific embodiments of the present disclosure include photoactive compositions comprising:

(a) at least one UV-Vis photoinitiator;

(b) a photopolymerizable prepolymer;

(c) at least one type of upconverting material, preferably an upconverting nanocrystal which, when irradiated by a wavelength of near infrared (NIR) light, emits at least one wavelength of light suitable for activating the UV-Vis photoinitiator.

In other aspects of these embodiments, the photoactive composition is adapted for use as a light adjustable lens, preferably an implantable intraocular lens. In certain of these embodiments, the lens further comprises a separate polymer matrix in which the photopolymerizable prepolymer, the UV-Vis photoinitiator, and the at least one type of upconverting nanocrystal are distributed.

In certain aspects of these embodiments, the photoactive composition or the light adjustable intraocular lens (or both) further comprises a UV-Vis blocker. This may be applied to either the "front" or "back" surface of the intraocular lens, for reasons described elsewhere herein, or may be distributed in the lens, either globally or within selective locations within the lens.

Typical materials used in these photoactive compositions or light adjustable lenses are described elsewhere in this disclosure. Preferably these materials are biocompatible and/or suitable for implantation in a patient, more preferably in a human patient. The photoactive compositions are suitable for implantation or deposition with the eye.

In certain embodiments, at least one type of upconverting nanocrystal comprises a lanthanide ion, for example one or more of ion of Er, Gd, Ho, Tm, Y, or Yb. The use of Tm-containing nanocrystals appears to be preferred. Illustrative examples of such upconverting nanocrystal include, but are not limited to, $NaGdF_4$, $NaYF_4$, $BaF_2$, $KYF_4$, or $BaGdF_5$ doped with one or more of Er, Gd, Tm, Y, or Yb. Some specific examples include $NaYF_4$:Yb, Er/Tm; $NaYF_4$:Yb, Er; $NaYF_4$:Yb, Tm; $NaYF_4$:Yb, Er/Gd; $LaF_2$:Yb, Tm. Such upconverting nanocrystal may be of any suitable shape, but hexagonal platelets appear to be preferred. These nanocrystals may also be surface modified with organic moieties to help compatibilize them with the other components of the compositions.

Other specific aspects of the core-shell nanocrystals are described further elsewhere herein.

Other embodiments include methods for using and modifying one of the disclosed light adjustable lenses or photoactive compositions, which may or may not be implanted into the eye of a patient, by irradiating the lens or composition with at least one wavelength of near infrared light, wherein the irradiation results in a change in a refractive property of the light adjustable lens or the compositions. This irradiation may be localized in one or more portions of the lens or composition, or the irradiation may be applied to the entire lens or composition. In at least some cases, this change in refractive property is the result of partial or complete polymerization, copolymerization, or crosslinking of the pre-polymer materials. Where the lens further comprises a separate polymer matrix in which the photopolymerizable prepolymer, the UV-Vis photoinitiator, and the upconverting nanocrystal are distributed, the separate polymer matrix may be inert with respect to the polymerization, copolymerization, or crosslinking of the photopolymerizable prepolymer, such that the photopolymerized prepolymer forms pockets or entangled networks of photopolymerized polymer within the separate polymer matrix. In other cases, the materials of the separate polymer matrix may copolymerize or crosslink with the photopolymerizable prepolymer. Depending on the nature of the irradiation and distribution of materials within the lens or composition, the resulting body may contain localized or distributed networks of polymerized, copolymerized, or crosslinked polymers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present application is further understood when read in conjunction with the appended drawings. For the purpose of illustrating the subject matter, there are shown in the drawings exemplary embodiments of the subject matter. However, the presently disclosed subject matter is not limited to the specific methods, devices, and systems disclosed. In addition, the drawings are not necessarily drawn to scale. In the drawings:

FIG. 8A shows results for compositions where no useful luminescence when using 808 nm source. FIG. 8B shows the effect of various coating layers and ratios of components on the emission in the range of 340 nm to 500 nm, normalized to the 475 nm emission band. FIG. 8C shows an expansion of FIG. 8B in the 365 nm emission band and FIG. 8D shows this same region for the largest 365 nm band producers (Multi-6Shell (May 17, 2016)>YYbTm@YYb@YNd@Y (Jan. 4, 2018—808) >Y@YbTm@Y (May 3, 2016)>YbTmFe@Y (Jan. 5, 2018) >YYbTm@YYb@YNd@Y (Jan. 4, 2018—980)). Note that some of these newer, smaller particles (blends of Cl salt synthesis and the TFA salt synthesis) have produced relative emission intensities similar to their large counterparts.

DETAILED DESCRIPTION OF ILLUSTRATIVE EMBODIMENTS

Figure 1A:
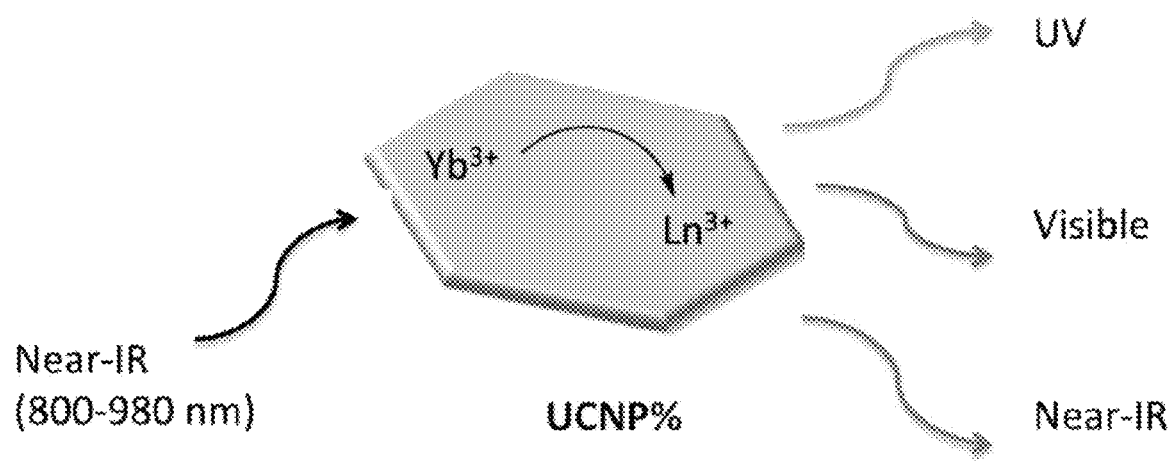
FIGS. 1A and 1B provide schematic representations of the operating principles of a lanthanide-doped upconverting core-shell nanocrystals converting near-IR light to higher energy wavelengths that can drive photochemical reactions.
Figure 1B:
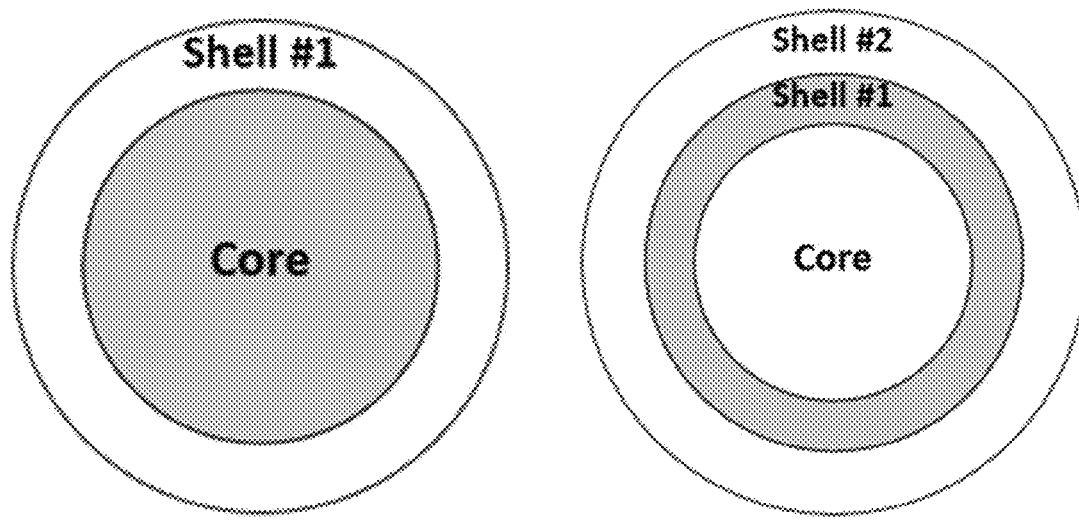
Figure 1B:
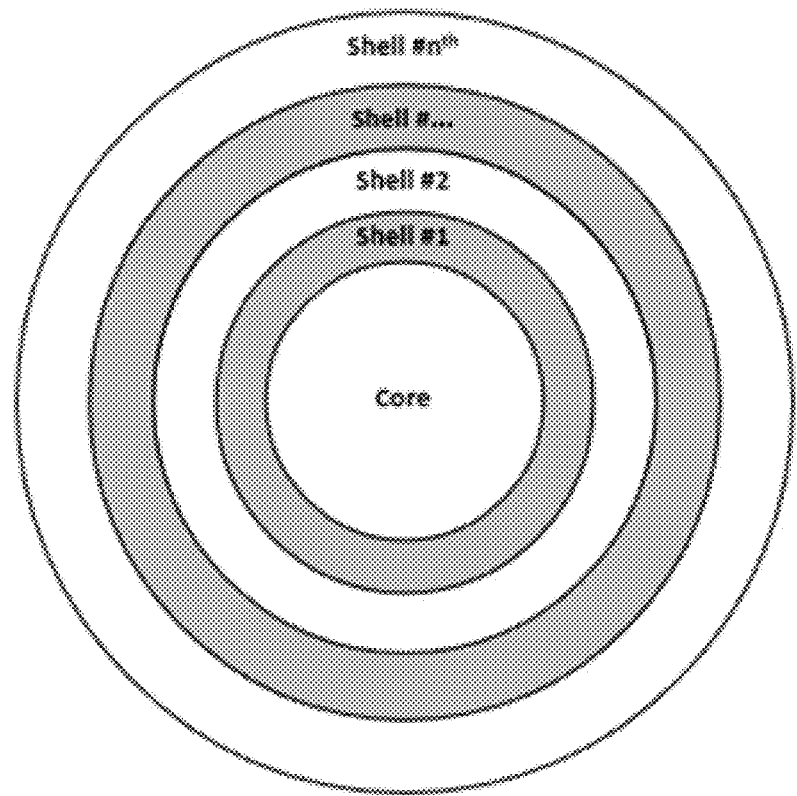
Figure 1B:
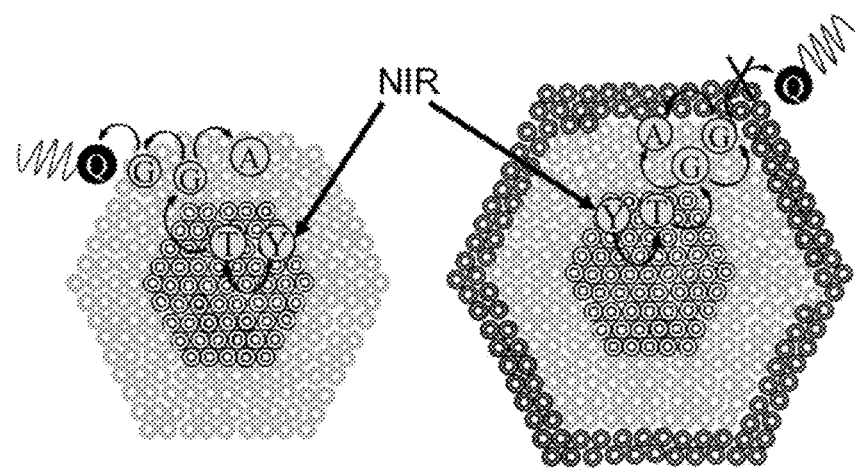
Figure 1B:
Figure 1B:
Figure 1B:
Figure 1B:
Figure 1B:
Figure 1B:
Figure 1B:
Figure 1B:
Figure 2:
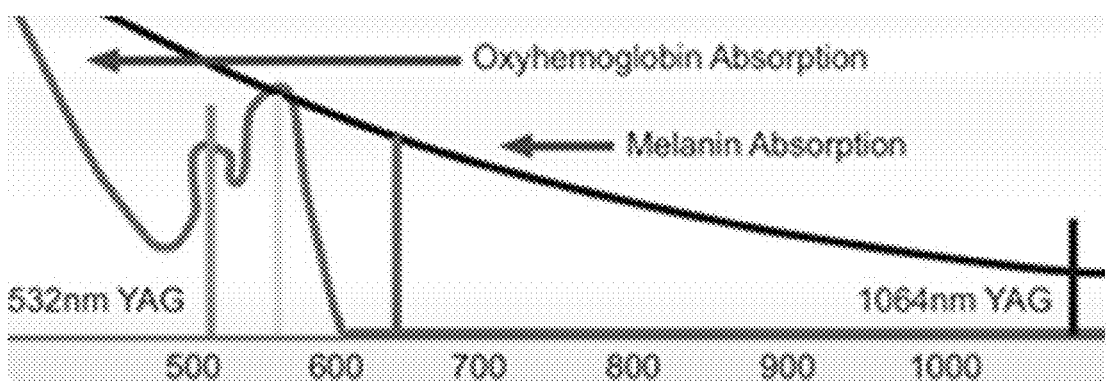
FIG. 2 shows absorption spectra for hemoglobin and melanin. Note minimal absorption at 980 nm used to activate one of the disclosed photoactive compositions.
Figure 3A:
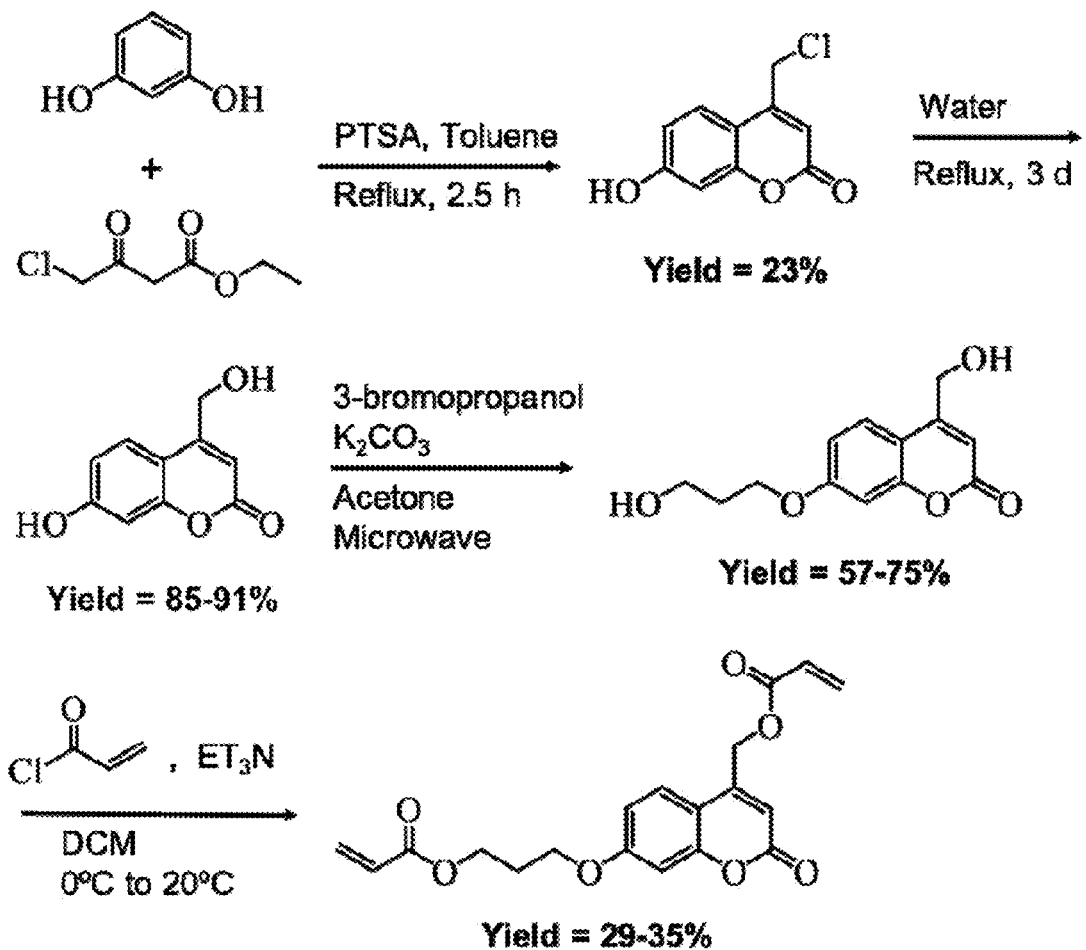
FIGS. 3A-G show seven Schemes for the synthesis and proposed reactions of various diacrylate-coumarin crosslinkers contemplated in this work for use are prepolymers or prepolymer linkers.
Figure 3B:
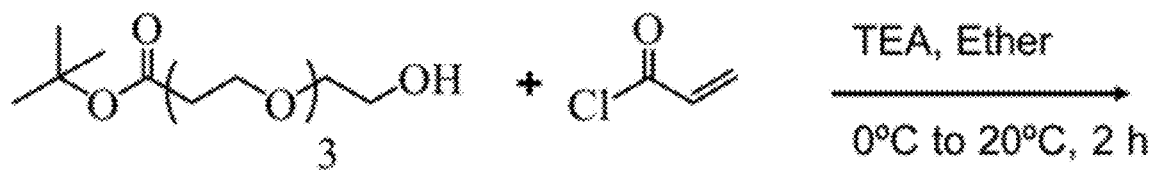
Figure 3B:
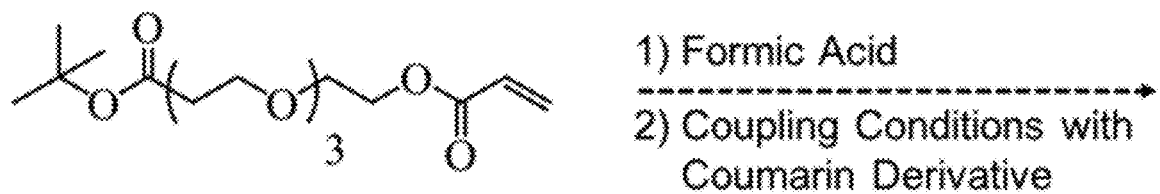
Figure 3B:
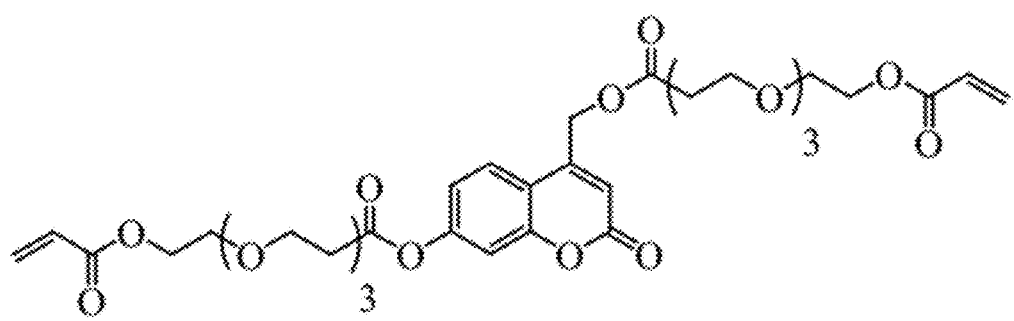
Figure 3C:
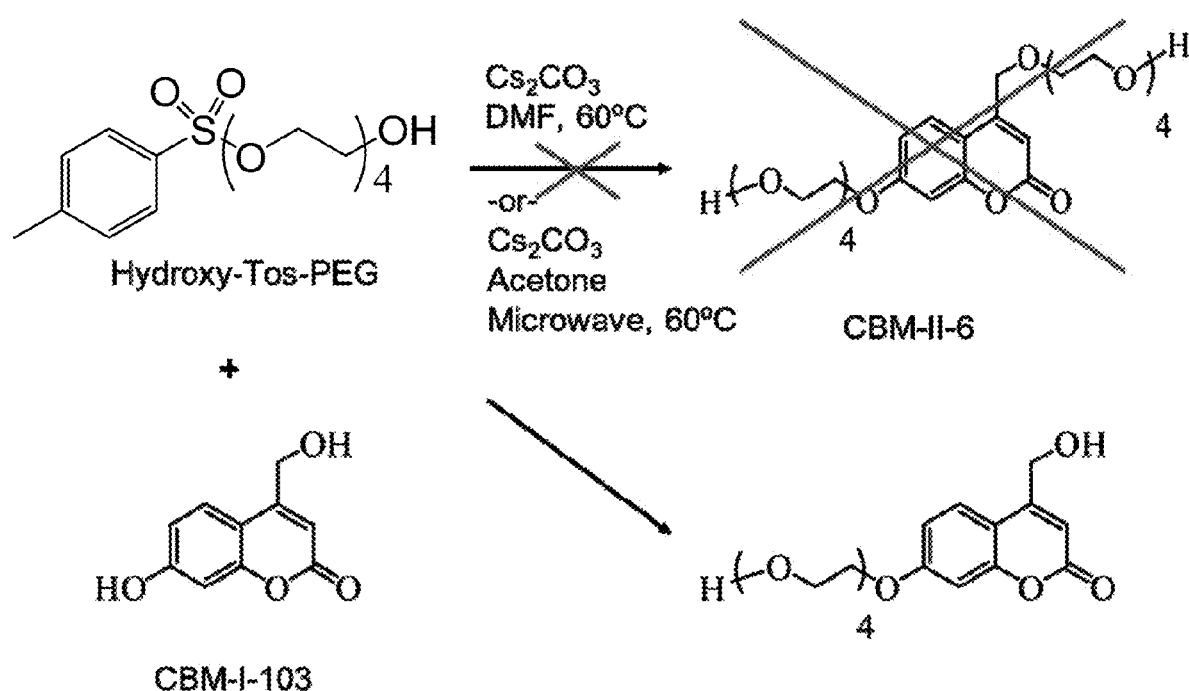
Figure 3D:
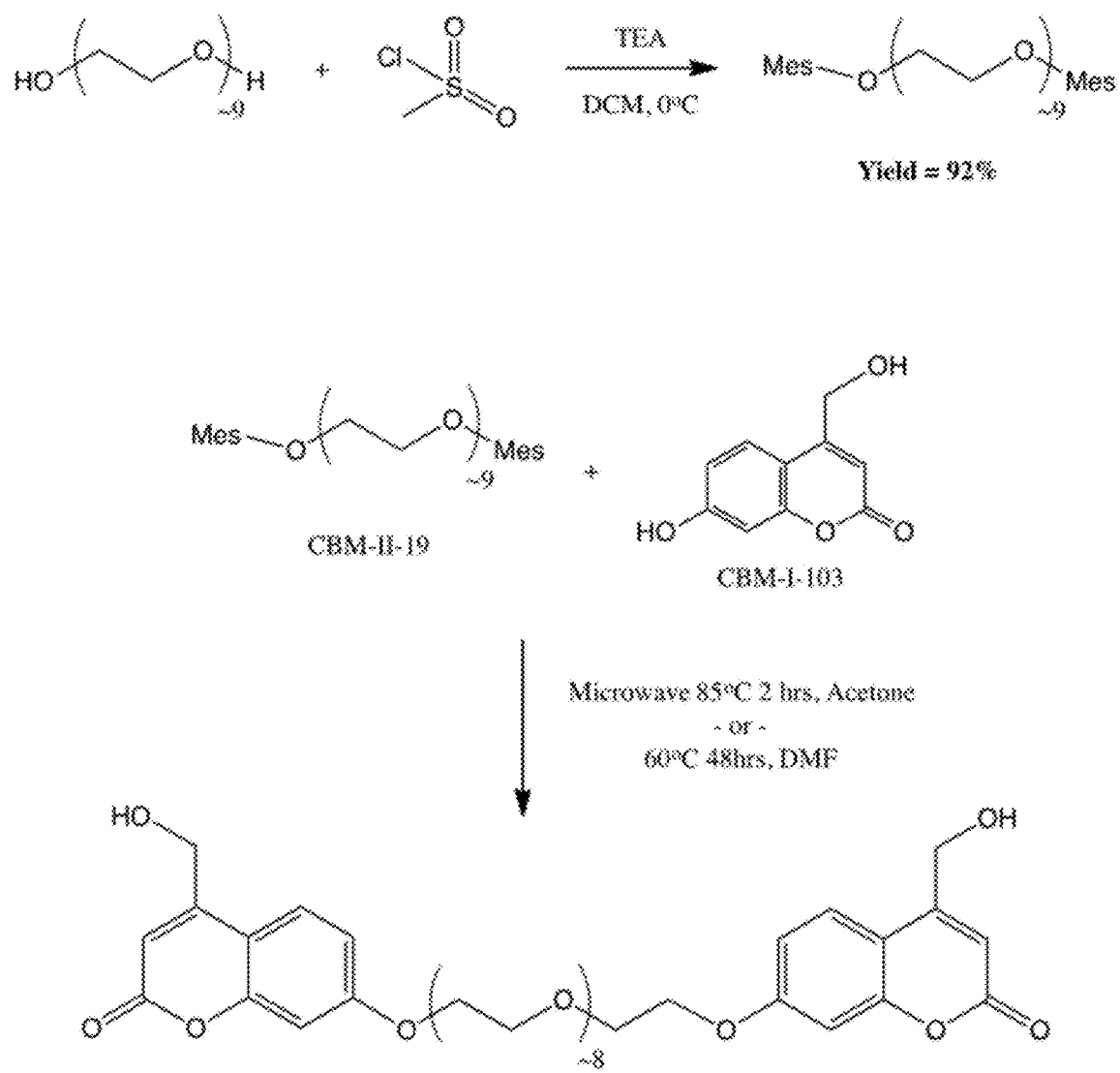
Figure 3E:
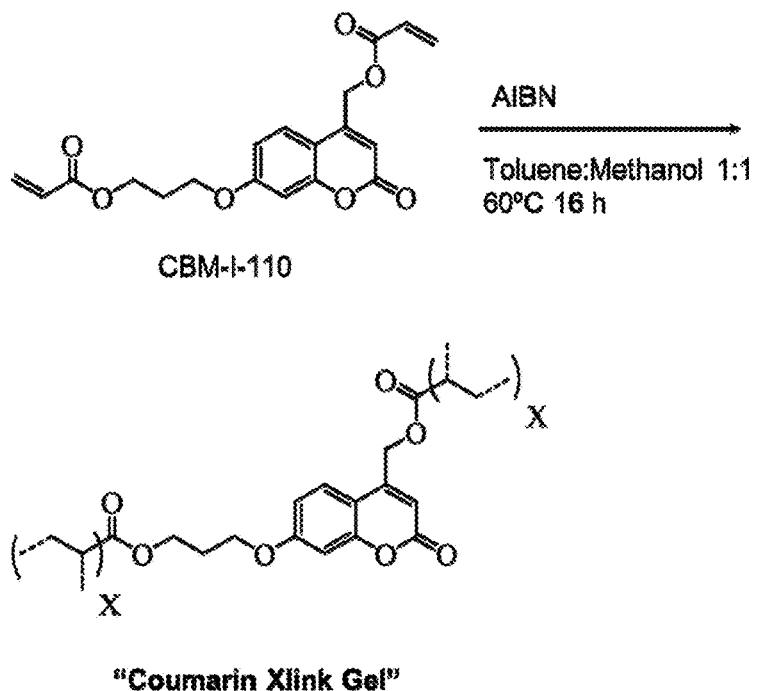
Figure 3F:
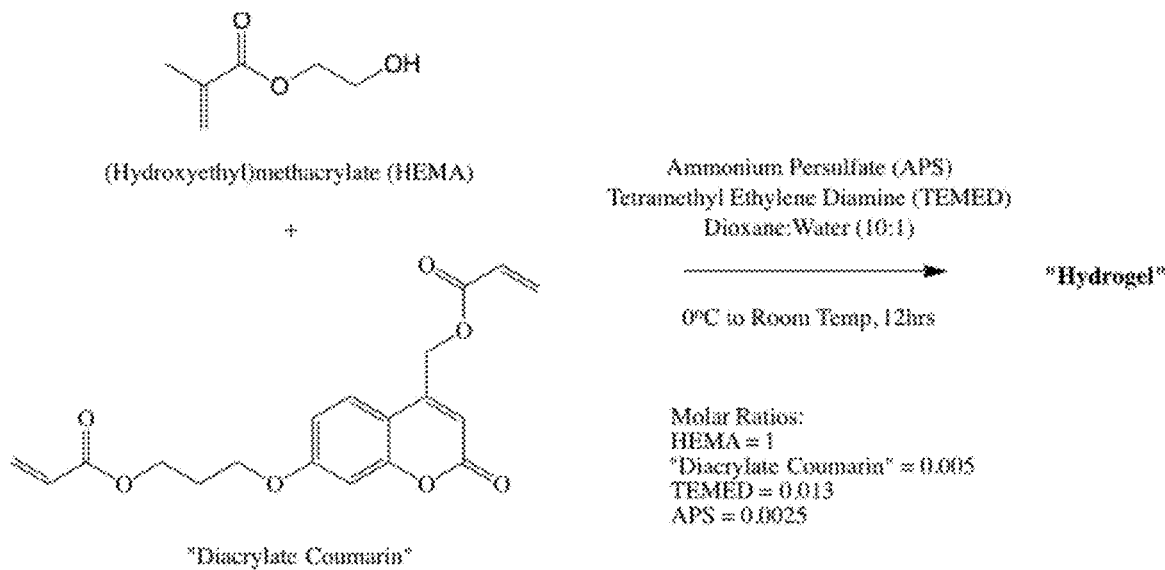
Figure 3G:
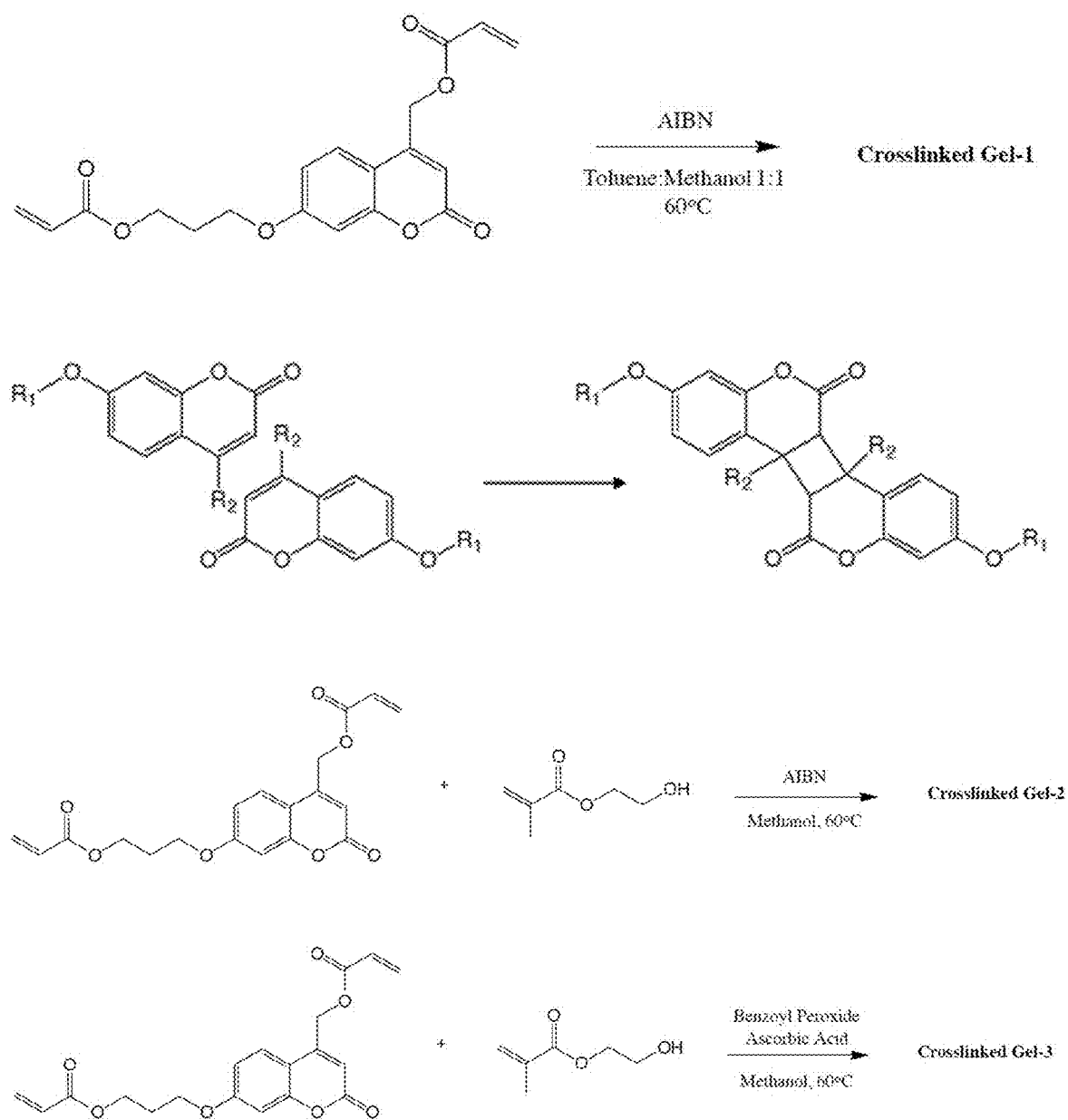

The present disclosure is directed to methods of providing and correcting light adjustable lens (LAL) inserted into an eye of a patient, methods of altering the refractive properties of these light adjustable lenses, for example by in situ polymerization or crosslinking of the compositions, and the compositions which allow for these methods.

Light offers many distinct advantages over other stimuli for controlling polymerization. The intensity and color can be tuned and used for remote activation of a wide range of materials at a specific time and location with relatively high precision. However, most examples of photo-induced polymerization are limited, as their photochemical reactions require the use of high-energy UV or visible light, neither of which can penetrate deeply into tissues and both of which can cause unwanted damage to surrounding tissues.

An appealing strategy to overcome this problem is the use of near infrared (NIR) light, for example through the use of NIR-absorbing upconverting nanoparticles, to induce the same reactions that are generally catalyzed by UV or visible light. The present disclosure recognizes the potential utility of such an approach in treatment of ocular conditions, including degenerative ocular conditions, for example myopia.

The instant disclosure uses a strategy to harness NIR light that takes advantage of NIR-absorbing nanoparticles, including lanthanide-doped upconverting nanoparticles (UCNPs). Such nanoparticles have the unique luminescent property of converting NIR to shorter wavelength, higher energy radiation (a process described as "upconverting"). See, e.g., FIG. 1. Such nanoparticles or nanocrystals offer many advantages, including low autofluorescence, large anti-Stokes shifts, tunable emissions, and high resistance to photobleaching making them suitable for repetitive imaging. In addition, upconverting core-shell nanocrystals are non-blinking, less light scattering, possess low cytotoxicity and can be activated even in deep tissue, as the NIR used for activation is within the optical transparency window of tissues. Thus, the use of long wavelength photochemistry (e.g., NIR light) appear to provide an ideal platform for the development of a safe and efficient optical devices.

The present inventors recognized that the use of upconverting nanoparticles (UCNPs) as the initiator and light-absorbing source in ocular compositions such as light adjustable lenses, thereby moving the wavelength of irradiation from the near UV to longer wavelengths, would eliminate many of the safety issues associated with adjustment and lock-in for light adjustable lenses. These systems can be irradiated with >750 nm, or even >900 nm, light and used to carry out photochemistry at lower wavelengths that would be compatible with current light adjustable lens technology.

As described herein, the concentration must be controlled to a level that allows the photochemistry to take place while shielding the retina. In some embodiments, it is useful to attach the photoinitiator to the nanoparticle to increase the efficiency of the system. upconverting nanocrystals are easily functionalized on their surface by a variety of photoactive groups. The first advantage of such a system is increased safety since the light is outside of the near UV range.

The use of upconverting nanocrystals allow the lens to be adjusted and stable without an initial lock-in procedure. The upconverting nanocrystals require sufficient photon flux to activate and the UV block will prevent the direct activation of the photo initiator (either in solution or attached to the surface of the upconverting nanocrystals). This combination of features will eliminate two of the issues with the present lens formulations. Since the system will not be activated by ambient light, the lens will not have to be protected between the time it is inserted and locked in. Without a required lock-in, the lens can be adjusted multiple times as needed over a reasonable long period of time. If essential, the lens can eventually be locked-in using a safe beam of >900 nm light. Additional advantages of the system are ease of use by eliminating a lock-in step and eliminating the need for eye protection before lock-in. The system also allows for multiple adjustments over an extended period of time and a safe lock-in if needed.

Further, this disclosure addresses some of the concerns associated with using single crystal upconverting nanocrystal previously described, and provide support for new strategies for improving the efficiencies of previous systems. Among these strategies include (a) the use of upconverting core-shell nanocrystals that provides convenient means for increasing emission luminescence and enhancing the relative amplitudes of the higher energy emissions; (b) the use of transition metals, such as iron, also to increase the amplitude of these higher energy emissions; (c) the use of inert coatings to enhance the general brightness of these emissions, and (d) to incorporate Nd and other lanthanide sensitizers into the shell(s) of core-shell nanocrystals to provide additional excitation wavelengths (i.e., below 980 nm), so as to reduce local heating due to minima in the water adsorption spectrum.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or device or a method of making or using a composition or device, it is appreciated that such a description or claim is intended to extend these features or embodiment to embodiments in each of these contexts (i.e., compositions, devices, methods of making, and methods of using).

Light Adjustable Lenses, Including Light Adjustable Intraocular Lenses

The present disclosure is directed to light adjustable optical devices, preferably light adjustable intraocular lenses, comprising:
(a) a photopolymerizable prepolymer;
(b) a UV-Vis photoinitiator;
(c) at least one upconverting core-shell nanocrystal; and
(d) optionally a UV-Vis blocker.

In some embodiments, the optical device further comprises a polymer matrix in which the photopolymerizable prepolymer material, the UV-Vis photoinitiator, the optional UV-Vis blocker, and the at least one upconverting nanocrystal are distributed. For suitability of purpose, the optical devices are transparent or practically transparent. When present as a formed lens, the optical device may also contain coatings on one or more surfaces capable of absorbing certain UV-Vis wavelengths, for reasons discussed elsewhere herein.

In some embodiments, the photosensitive compositions described herein are adapted for use as optical devices in human patients, including those for implanting into human patients. Non-limiting examples of these optical devices being light adjustable intraocular lenses, corneal inlays, corneal rings, or keratoprotheses. In some embodiments, these optical devices are surgically implanted or otherwise positioned within the eye of the patient. In some of these cases, in addition to the photopolymerizable prepolymer material, the optionally functionalized UV-Vis photoinitiator, and the at least one type of optionally functionalized upconverting core-shell nanocrystal, the light adjustable lens further comprises a separate polymer matrix material in which the other ingredients are distributed. This separate polymer matrix is a covalently or physically linked structure that may function as a discrete optical element, and typically gives the light adjustable lens its shape and effects hardness, flexibility and other physical properties of the light adjustable lens. In addition to these characteristics, the light adjustable lens is preferably biocompatible, suitable for implantation into the eye of a patient.

Such polymeric matrix materials may be useful in defining the structure and properties of light adjustable lenses. These polymeric matrix materials, described more elsewhere herein, may be inert with respect to polymerization and/or crosslinking, or may contain substituent functional groups capable of such polymerizing, copolymerizing, or crosslinking with like materials, added prepolymers, or other suitably functionalized materials.

These optical devices can be prepared using techniques the same as or similar to those now utilized for the manufacture of comparable currently available optical devices, for example intraocular lenses. With appropriate cross-link density and water content, the lens can be molded to provide foldable lens of a variety of powers and manufactured with standard haptics The polymer matrix may comprise biocompatible polymers, homopolymers, and/or copolymers. Such biocompatible materials may result from the polymerization of (meth)acrylates, (meth)acrylamides, phosphazenes, siloxanes, vinyls, or mixtures thereof (or any one or more of the prepolymer materials described elsewhere herein). Illustrative examples of the polymer matrix material include: poly[meth]acrylates such as polyalkyl[meth]acrylates and polyhydroxyalkyl [meth]acrylates (where alkyl refers to, e.g., methyl, ethyl, or propyl); polyvinyls such as polystyrene and polyvinyl alcohol (PVA); polyvinylpyrrolidone; polyalkylene oxides, polyvinylpyrroles, polyamino acids, polysaccharides, polysiloxanes such as polydimethylsiloxane; polyphosphazenes; polynucleic acids, as well as copolymers thereof. Such polymers may be substituted or unsubstituted, for example by alkyl groups, or any of the functional groups described herein.

As used herein, the use of the parenthetical "(meth)" refers to the optional presence of methyl or alkyl groups on the named material. For example, the term "(meth)acrylate" refers to materials that include acrylate, methacrylate, or both acrylate and methacrylate monomers, as is recognized in the art for such materials (likewise, "(meth)acrylamide" refers to acrylamide, methacrylamide, or both acrylamide and methacrylamide moieties). In more preferred embodiments, the acrylates or methacrylates (i.e., "(meth)acrylates") are substituted with water compatible functionalities, such as hydroalkyl (e.g., hydroxymethyl, hydroxyethyl, or hydroxypropyl) groups. Nonhydrophilic monomers can be used to help to modify the hydrophilicity and the refractive index of the polymer materials, and in the case of (meth)acrylate polymers, hydrophobic acrylates/methacrylates can be used to tune these properties. Exemplary suitable (meth)acrylates include 2-hydroxymethyl (meth)acrylate, 2-hydroxyethyl (meth)acrylate, methyl-2-(hydroxymethyl)(meth) acrylate, ethyl 2-(hydroxymethyl)(meth)acrylate, 2-phenylethyl (meth)acrylate, methyl(meth)acrylate and 3-phenylpropyl (meth)acrylate.

The polymer matrix typically comprises polymerized [meth]acrylate groups. The polymer matrix may be hydrophilic or hydrophobic. The polymer matrix may further comprise water in a range of from 0.01 wt % to 0.5 wt %, from 0.5 wt % to 1 wt %, from 1 wt % to 2 wt %, from 2 wt % to 3 wt %, from 3 wt % to 4 wt %, from 4 wt % to 5 wt %, from 5 wt % to 7 wt %, from 7 wt % to 10 wt %, from 10 wt % to 20 wt %, from 20 wt % to 30 wt %, from 30 wt % to 40 wt %, from 40 wt % to 45 wt %, from 45 wt % to 50 wt %, or a be present in a range defined by two or more of these ranges, relative to the weight of the polymer matrix.

In certain embodiments, the matrix polymers or copolymers of the light adjustable lens may be inert with respect to crosslinking. In other embodiments, the matrix polymers or copolymers of the light adjustable lens contain suitable functional groups capable of crosslinking in the presence of the photoactivation described herein. In either of these embodiments, the light adjustable lens may also contain additional photopolymerizable materials, or such additional photopolymerizable materials may be absent. Each of these light adjustable lens compositions—polymer matrix materials with or without photoactivatable functional groups, each in the presence of absence of added photopolymerizable prepolymer material—is considered an independent embodiment.

The light adjustable lens may also contain one or more other components, each capable of performing one or more functions. For example, in addition to the separate polymer matrix material which provides structure to the lens, the lens may also include colorants, anti-reflection compounds, biocompatibility-enhancing agents, antibacterial agents, and the like. These may be incorporated onto one or more surfaces of the lens or may be incorporated into the lens body. Many such colorants, anti-reflection compounds, biocompatibility-enhancing agents, antibacterial agents, etc. are known and are suitable to be included in the matrix material, and may be incorporated according to the desired application.

It is worth noting that one or more of the components in the photosensitive compositions may serve two or more functions attributable to the composition, including polymerizing (copolymerizing), crosslinking, photoactivating, or upconverting through suitable tethering groups; e.g., the crosslinking prepolymer may contain a UV-Vis blocking material (discussed elsewhere herein).

Prepolymers

As also described elsewhere herein, the prepolymer may comprise an organic or inorganic monomer, oligomer, macromer, or mixture or combination thereof, capable of polymerization, co-polymerization, and/or crosslinking upon suitable initiation, by activation by the activation provided by at least one UV-Vis photoinitiator. Such prepolymers may contain polymerizable moieties capable of polymerizing, copolymerizing, or crosslinking with other similarly or complementarily functionalized groups. In particular aspects of the invention, the prepolymer may be considered inactive, and in a particular context of the invention is in a non-polymerizable form, until activated by the photoinitiator.

In some embodiments, these prepolymers polymerize or crosslink with the polymer matrix. In other embodiments, the polymer matrix is inert with respect to crosslinking and the prepolymers polymerize or crosslink with themselves or other materials within the polymer matrix.

In some embodiments, the photopolymerizable prepolymer comprises a polyethylene glycol (PEG), a poly[alkyl or dialkyl]siloxane, a poly[meth]acrylate, a poly(amino acid), a poly(amino acid)-copolymer, a polycarbohydrate, a protein, or a polysaccharide backbone.

Exemplary polymerizable groups or moieties include functional groups such as alkenyl, allyl, cyclic ether (e.g., epoxy), cyclic acetal, cyclic siloxane, diene, lactone, lactam, vinyl, terminal vinyl ether, vinylidene, N-vinyl carbazole, or [meth]acrylate groups. In some embodiments. Other examples of suitable cross-linkable groups include but are not limited to acetoxy, alkoxy, amino, anhydride, aryloxy, carboxy, enoxy, epoxy, halide, isocyano, olefinic, and oxine. Especially useful examples of the photopolymerizable prepolymer include [meth]acrylates, polyhydroxyalkyl [meth]acrylates, [meth]acrylamide], allyloxy, cinnamoyl, styrenes, vinylpyrrolidones, and/or mixtures thereof.

Examples of polymerizable monomers containing a double bond include alkyl, aryl, hydroxyalkyl, cycloalkyl (optionally including an O) or amino acrylates, or alkyl, hydroxyalkyl, cycloalkyl (optionally including an O atom) or amino methacrylates, for example methyl, ethyl, butyl, 2-ethylhexyl, phenyl or 2-hydroxyethyl acrylate, tetrahydrofurfuryl acrylate, isobornyl acrylate, methyl methacrylate, cyclohexyl methacrylate or ethyl methacrylate, hydroxyalkyl acrylates such as 2-hydroxyethyl acrylate, etheralkyl acrylates such as 2-methoxyethyl acrylate, alkoxyor aryloxy-poly(alkylene glycol) acrylates such as methoxypoly (ethylene glycol)acrylates, ethoxypoly(ethylene glycol) acrylates, polyethylene glycol diacrylate, methoxypoly (propylene glycol)acrylates, methoxypoly(ethylene glycol)-poly(propylene glycol)acrylates or their mixtures, aminoalkyl acrylates such as 2-(dimethylamino)ethyl acrylate (DMAEA), fluoroacrylates, silyl acrylates, phosphorus acrylates such as alkylene glycol phosphate acrylates, methacrylic monomers such as methacrylic acid or its salts, alkyl, cycloalkyl, alkenyl or aryl methacrylates, such as methyl methacrylate (MMA), lauryl methacrylate, cyclohexyl methacrylate, allyl methacrylate, phenyl methacrylate or naphthyl methacrylate, hydroxyalkyl methacrylates such as 2-hydroxyethyl methacrylate or 2-hydroxypropyl methacrylate, etheralkyl methacrylates such as 2-ethoxyethyl methacrylate, alkoxy- or aryloxy-poly(alkylene glycol) methacrylates such as methoxypoly(ethylene glycol) methacrylates, ethoxypoly(ethylene glycol)methacrylates, methoxypoly(propylene glycol)methacrylates, methoxypoly(ethylene glycol)-poly(propylene glycol)methacrylates or their mixtures, aminoalkyl methacrylates such as 2-(dimethylamino)ethyl methacrylate (DMAEMA), fluoro methacrylates such as 2,2,2-trifluoroethyl methacrylate, silyl methacrylates such as 3-methacryloylpropyltrimethylsilane, and phosphorus methacrylates such as alkylene glycol phosphate methacrylates, hydroxyethylimidazolidone methacrylate, hydroxyethylimidazolidinone methacrylate, or 2-(2-oxo-1-imidazolidinyl)ethyl methacrylate.

Silicone acrylates may also be used. Further exemplary polymerizable moieties include acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride. Further exemplary polymerizable moieties include: vinylaromatic monomers such as styrene or substituted styrenes, (e.g., alphamethylstyrene), acrylonitrile, acrylamide or substituted acrylamides, 4-acryloylmorpholine, Nmethylolacrylamide, methacrylamide or substituted methacrylamides, trimethylolpropane triacrylate, acryloyl chloride, N-methylolmethacrylamide, methacrylamidopropyltrimethyl ammonium chloride (MAPTAC), itaconic acid, maleic acid or its salts, maleic anhydride, alkyl or alkoxy- or aryloxy-poly (alkylene glycol) maleates or hemimaleates, vinyl alcohols, vinylpyridine, vinylpyrrolidinone, (alkoxy) poly(alkylene glycol)vinyl ether or divinyl ether, such as methoxy poly(ethylene glycol)vinyl ether, poly(ethylene glycol)divinyl ether, olefin monomers, among which mention may be made of ethylene, butene, hexene and 1-octene and also fluoro olefin monomers, and vinylidene monomers, among which mention may be made of vinylidene fluoride, these monomers being used alone or as a mixture of at least two aforesaid monomers.

Examples of polymerizable monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

In some embodiments, the photopolymerizable prepolymer comprises a oligomer, macromer, or even polymer having a polyethylene glycol (PEG), a poly[alkyl or dialkyl] siloxane, poly(amino acids), poly(amino acid)-copolymer, polycarbohydrate, a polypeptide/protein, or a polysaccharide backbone.

Exemplary polysaccharides include poly(hyaluronic acid), dermatansulfate, chondroitinsulfate, and or keratansulfate.

Exemplary polypeptides include elastins. Elastins include native elastin, engineered elastin, or a mixture thereof. Some engineered elastin contain one or more natural amino acid substitutions suitable for polymerization. Alternatively or additionally, the engineered elastin may further or instead comprises one or more non-natural amino acids comprising one or more chemical groups that are appropriate for polymerization, for photoinitiation, or both. For example, an elastin, modified by attachment of two or more methacryl or acryl groups, is a useful material.

In certain embodiments, these prepolymers may comprise photocleavable linkages; said composition being deformable upon cleavage of the photocleavable linkages, said photocleavable linkages being receptive to cleavage with an application of at least one activating wavelength of light in a range of from about 200 nm and about 1000 nm (1 micron). Typically, these photocleavable linkages are receptive to photocleavage by an application of a double or multiple photon irradiation ("multiphoton excitation"), for example comprising at least one coumarin moiety, nitrobenzyl-ether moiety, nitroindoline-ether moiety, or p-hydroxyphenacyl moiety, or a combination thereof. Other cross-linkers such as ortho nitro benzyl alcohol derivatives (e.g., Table 1) can also be used as fragment of cleavable cross-linker. See also the systems shown in the Schemes of FIGS. 3A-G.

TABLE 1

Some exemplary cross-linkers

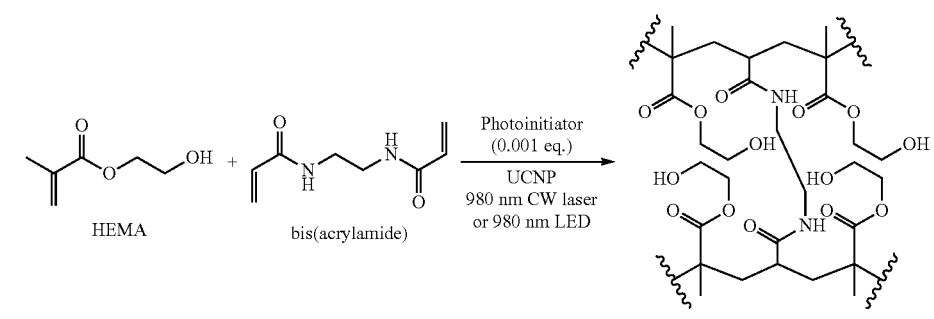

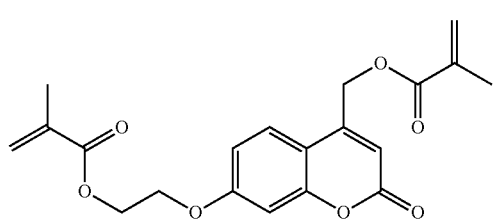 [SMILES: C=C(C)C(=O)OCCOc1ccc2c(COC(=O)C(=C)C)cc(=O)oc2c1]

TABLE 1-continued

Some exemplary cross-linkers

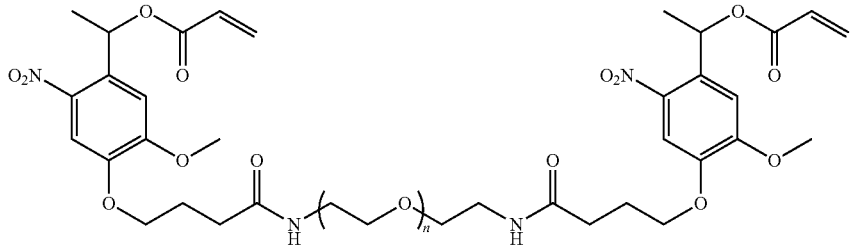

The use of photocleavable crosslinkers offers additional flexibility in tuning the optical properties of lenses.

Photoinitiators

A photoinitiator, and especially a UV-Vis photoinitiator is a compound capable of converting absorbed light energy, generally or especially UV or visible light, into chemical energy in the form of initiating species, e.g., free radicals or cations. In some embodiments, the photoinitator absorbs light or has an absorption maximum in a range of from 250 nm to 600 nm. In other embodiments, the photoinitiator absorbs light or has an absorption maximum in a range of from 300 nm to 400 nm. In certain embodiments, the photoinitator exhibits an absorption maximum in range of from 350 nm to 450 nm ("blue range," defined as including one or more ranges of from 350 nm to 360 nm, from 360 nm to 370 nm, from 370 nm to 380 nm, from 380 nm to 390 nm, from 390 nm to 400 nm, from 400 nm to 410 nm, from 410 nm to 420 nm, from 420 nm to 430 nm, from 430 nm to 440 nm, or from 440 nm to 450 nm, preferably 360 nm to 370 nm) or in a range of from 450 nm to 600 nm ("red range," defined as including one or more ranges including from 450 nm to 500 nm, from 500 nm to 550 nm, or from 550 nm to 600 nm).

Based on the mechanism by which initiating radicals are formed, photoinitiators are generally divided into two classes: Type I photoinitiators undergo a unimolecular bond cleavage upon irradiation to yield free radicals; Type II photoinitiators undergo a bimolecular reaction where the excited state of the photoinitiator interacts with a second molecule (a co-initiator) to generate free radicals. UV photoinitiators of both Type I and Type II are known whereas visible light photoinitiators generally belong to the Type II class. Such "initiating species" serve to initiate polymerization in a suitable photopolymerizable material, in this case, either tissue or a photopolymerizable material. The photoinitiators may be in particular embodiments water soluble, inhibited by oxygen, and are preferably biocompatible.

Any suitable photoinitiator may be used in the invention so long as it is photoactivatable and upon photoactivation it either initiates polymerization of the photopolymerizable prepolymer, functionalized matrix, or other component.

In certain embodiments, the photoinitator comprises an acetophenone, a benzophenone, a benzoin ether, a benzil ketal, an α-dialkoxyacetophenone, an alkylphenone, an α-hydroxyalkylphenone, an α-aminoalkylphenone, a xanthone, or a thioxanthone moiety.

Exemplary photoinitiators include but are not limited to at least one of an acetophenone, anisoin, an anthraquinone, a sodium salt of anthraquinone-2-sulfonic acid, benzil, benzoin, a benzoin ether (e.g., ethyl, methyl, isopropyl, isobutyl ether), benzophenone, 3 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino) benzophenone, camphorquinone, 2-chlorothioxanthen-9-one, dibenzosuberenone, 2,2-diethoxyacetophenone, 4,4'-dihydroxybenzophenone, 2,2-dimethoxy-2-phenylacetophenone, 2,2-dimethoxy-1,2-diphenylethan-1-one, 4-(dimethylamino)benzophenone, 4,4'-dimethylbenzil, 2,5-dimethylbenzophenone, 3,4-dimethylbenzophenone, eosinY, 4'-ethoxyacetophenone, 2-ethylanthraquinone, fluorescein, hydroxyacetophenone, 3-hydroxybenzophenone, 4-hydroxybenzophenone, 1-hydroxycyclohexyl phenyl ketone, 2-hydroxy-2-methylpropiophenone, 2-mercaptothioxanthone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, or a thioxanthen-9-one. Also useful in the practice of the invention are photoinititators having two initiators linked by a short polymer backbone, e.g., benzoin polydimethyl siloxane Benzoin (B-pdms-B) wherein two benzoin moieties are linked by a dimethyl siloxane bridge. In some cases, the photoinitiator may also be associated with a sensitizer. Suitable sensitizers include p-(dialkylamino aldehyde); n-alkylindolylidene; and bis [p-(dialkyl amino) benzylidene] ketone.

Typically these operate by absorbing light in the 300-400 nm range. Other photoinitiators which may function by absorbing at higher wavelengths may also be attractive for accessing lower energy, higher wavelength emissions (e.g., 400 to 500 nm). Examples of such photoinitiators include IRGACURE™ 369 (2-benzyl-2-(dimethylamino)-1-(4-morpholinophenylphenyl)butan-1-one), IRGACURE™ 819 ((phenylphosphoryl)bis((2,6-dimethylphenyl)methanone))), and IRGACURE™ 784, respectively, available from Ciba Specialty Chemicals. Still other strategies include moving towards type II photo-initiators and aim for something that absorbs in the "red" range (650-700 nm) of the visible spectrum.

In preferred embodiments, the photoinitiator compound comprises Eosin Y, Eosin B or fluorescein. Eosin Y is most commonly known as a water soluble xanthene dye. Eosin Y is a Type II photoinitiator that is typically used in combination with triethanolamine (TEOA). However, as with other Type II photoinitiators, any suitable co-initiator can be used. Having an absorption peak around 514 nm, Eosin Y is activated efficiently by low-toxicity, visible (green) light. Notably, Eosin Y itself has been shown to exhibit biocompatibility in a range of applications.

Upconverting Core-Shell Nanocrystals

Upconverting materials include those materials which exhibit an anti-Stokes shift on absorption and emission of energy; that is, having absorbed a wavelength of energy, it emits one or more wavelengths of higher energy (lower wavelength). In the instant case, these upconverting materials are preferably upconverting core-shell nanocrystals which, when irradiated by a wavelength of near infrared (NIR) light, emits at least one wavelength of light suitable for activating the UV-Vis photoinitiator. In certain aspects of this disclosure, the NIR light includes at least one wavelength in range of from about 750 nm to about 1400 nm (or within one of the subranges described elsewhere herein).

As described herein, such upconverting nanocrystals comprise at least one lanthanide ion. As used herein, the term lanthanide ion refers to an ion of any one of the lanthanide elements, including La, Ce, Pr, Nd, Pm, Sm, Eu, Gd, Tb, Dy, Ho, Er, Tm, Yb, or Lu. In certain preferred embodiments, the lanthanide ion is one or more of Er, Gd, Ho, Tm, Y, or Yb.

Such lanthanide ions are typically present as dopants in fluoride or oxide type crystals, for example, in crystals comprising $NaGdF_4$, $NaYF_4$, $BaF_2$, $KYF_4$, or $BaGdF_5$. Compostions of these crystals doped with one or more of Er, Gd, Tm, Y, or Yb are known for their characteristic emissive properties. Specific examples include $NaYF_4$:Yb, Er/Tm; $NaYF_4$:Yb, Er; $NaYF_4$:Yb, Tm; $NaYF_4$:Yb, Er/Gd; and $LaF_2$:Yb, Tm. Other examples include those upconverting nanocrystal comprising $NaYF_4$, $BaF_2$, $CaF_2$, $LaF_2$, $KYF_4$, $Y_2O_3$, $Y_2O_2S$, or $BaGdF_5$ doped with one or more of Er or Tm and Yb (for example, and especially $NaYF_4$:Yb, Er/Tm).

Core-shell materials, as the name implies, are particles or in this case crystalline materials comprising a crystalline core surrounded by one or more layer, which may be photoactive or inert. Such nanoparticles/nanocrystals offer the possibility of tuning both the emission and absorptions of the nanocrystals, for example to increase the relative amplitude of higher energy emissions and improve the quantum yields of the processes described herein. Core-shell nanoparticles, both cores and shells may be prepared by wet chemical methods as opposed to epitaxial growth means, thereby producing such materials less expensively than in other methods, but with comparable performance. Such methods also allow for the incorporation of other dopants (e.g., transition metals such as Fe), at least more conveniently than other methods. Two such wet chemical methods are disclosed herein.

In certain embodiments, the at least one type of upconverting core-shell nanocrystal comprises:

(a) a nanocrystalline core optionally comprising a lanthanide sensitizer capable of absorbing light in a range of from 780 nm to 1020 nm and having at least one emission peak in the range of from 250 nm to 500 nm;

(b) at least one shell superposed on the nanocrystalline core, the at least one shell comprising at least one lanthanide activator; and (c) an optically an inert outer layer superposed over the at least one activating shell. Such compositions may comprise multiple shells may be used, each of which may be the same or different from the neighboring shell. The term "at least one shell" means one or more, for example 1 to 6, preferably 3 to 4 layers. The terms "activator" and "sensitizer" are well known in the art of such upconverting lanthanide crystals.

In the present case, in certain embodiments the nanocrystalline core comprises a $NaGdF_4$, $NaLuF_4$, $LiYF_4$, $NaYF_4$, $KYF_4$, $KYb_2F_7$, $BaF_2$, $CaF_2$, $SrF_2$, $LaF_3$, $YF_3$, $BaYF_5$, $BaGdF_5$, $KY_3F_{10}$, YOF, LuOF, or GdOF host doped with one or more lanthanides such as Er, Gd, Ho, Tm, Y, or Yb, and optionally one or more transition metal ions, e.g., Fe. Typically, the dopants are present as their trications, for example as $Er^{3+}$, $Fe^{3+}$, $Gd^{3+}$, $Ho^{3+}$, $Tm^{3+}$, $Y^{3+}$, or $Yb^{3+}$. In other embodiments, the nanocrystalline core comprises the at least one lanthanide activator that is Gd, Nd, Yb, Eu, Tb, Dy, and/or Sm. In preferred embodiments, the at least one lanthanide sensitizer comprises Gd, Nd, and/or Yb. In other embodiments, the core is inert, and the at least one lanthanide activator is present on at least one of the shells.

In some embodiments, the nanocrystalline core comprises one or more of Er, Fe, Gd, Ho, Tm, Y, or Yb, preferably Tm, Er, Fe, Ho, or combination thereof. In other embodiments, the nanocrystalline core comprises a host doped with one or more of (i) Er or Tm and (ii) Yb ($NaYF_4$:Yb, Er/Tm). In certain preferred embodiments, the core is doped with Y, Yb, and Tm.

Given the wavelengths at which these ions typically emit, Tm appears to be preferred in cases where the aborption maxima of the photoinitiators are in the lower UV-Vis range (e.g., ca. 250-350 nm, emitting wavelengths well into this range. In certain embodiments, Tm is present as a dopant at levels in a range of from 0.1 to 3 mol %, preferably from 0.1 to 0.5 mol %, and more preferably at 0.2 to 0.3 mol %.

In other cases, where mid-range photoinitiators are used, lower energy, higher wavelength emission bands may be used, providing suitable excitation energies for the intended purpose.

The dopants may further comprise transition metal ions, for example comprising Co, Ti, Zr, and/or Hf, and/or other lanthanides, for example comprising Pr, Nd, Sm, Eu, Gd, Tb, and/or Dy. As described elsewhere herein, addition of a transmitter ion, such as comprising Fe, greatly enhances emission at 365 nm, thereby mimicking the performance of larger, Tm-containing upconverting nanocrystals. As shown herein, the use of Fe as a dopant, representative of other transition metal dopants, produced an emission at 365 nm similar to these larger Tm-doped materials. Note here that the use of transition metal dopants, including Fe ions, for this or any other purpose is not limited to upconverting core-shell nanocrystals. That is, these dopants also serve as effective transmitters in single phase upconverting nanocrystals (e.g., equivalent to the core of a core-shell nanocrystal with no shells or with a core and one or more inert coating layers).

Other embodiments include those upconverting core-shell nanocrystals with other arrangements of shells, for example, where a sensitizer is incorporated into a shell. For example, a layered constructions including an isolated Nd layer gave access to another excitation wavelength at 808 nm. These particles, then, independent activated at both 808 nm or 980 nm produced similar emissions at 365 nm. Switching to 808 nm can minimize heating due to local minima in the water adsorption spectra.

In related embodiments, the upconverting core-shell nanoparticles may include inert cores and the sensitizers in the shells.

Generally, these lanthanide ion (or transition metal ion) dopants are present at levels suitable for its intended purpose, as recognized by a person of skill in the art. In certain specific embodiments, at least one is present in a range of from about 0.1 to 0.25 mol %, from 0.25 to 0.5 mol %, from 0.5 to 1 mol %, from 1 to 2 mol %, from 2 to 3 mol %, from 3 to 5 mol %, from 5 to 10 mol %, from 10 to 20 mol %, or in a range containing two or more of these ranges.

In certain embodiments, the absorption wavelength of the at least one type of upconverting core-shell nanocrystal is the target of laser excitation. In other embodiments, the at least one emission peak is matched to the absorption maximum of the photoinitiator. In certain embodiments, 311 nm and 365 nm are attractive target wavelengths.

While these nanocrystals are also known to exist in shapes including the cubic, spheroid, and ellipsoid, in preferred embodiments, those upconverting nanocrystal present as hexagonal platelets appear to provide the best results.

The lanthanide activators can be the same or different than the lanthanide sensitizer; often both are mixtures that can contain both common and different lanthanides, but can also contain the same elements and may even be the same composition (e.g., use of Y or Gd as common ingredient).

It is found that coating the upconverting core-shell nanoparticles with inert outer shells enhances their ability to perform in the environments of the intraocular lenses. Without intending to be bound by any particular theory, it is believes that the inert layer reduces environmental quenching so as to provide increased higher energy emissions. In this regard, it is found that coating the nanocrystals with materials such as yttrium, a $C_{6-24}$ saturated or unsaturated fatty acid, an optionally functionalized silicate polymer coating (e.g., mesoporous silica), or a alkali metal fluoride or alkaline earth metal fluoride (e.g., $CaF_2$) suitably provides such enhancement. More generally, this coating can be more broadly defined in terms of inorganic (e.g., glass) coatings, or using organic compounds, having hydrophilic "head" that bonds to the nanoparticle and a hydrophilic or hydrophobic "tail" that provides dispersibility in the polymeric matrix of the lens materials. Methods for providing these coatings are described in the Examples.

Depositing an outer silica layer provided a route to facile chemical modifications. A variety of silane linkers are cheap and readily available. These can be used to coat the particles with similar compositions used in the intraocular lenses for better dispersion in the material. The chemical handles also provide a means to link the photo-initiator to the nanocrystal surface, which can be used to increase the photo-activation efficiency. In certain aspects then, the at least one type of upconverting nanocrystal is tethered to at least one of the photoinitiators by coupling a functional group on the photoinitiator with the presented functional group of the surface modified upconverting nanocrystal.

Similar functionalization can be used to further enhance other aspects of performance. For example, these nanocrystals can also be surface-modified which to enhance their hydrophilicity or functionality, for example by attaching molecules having two or more linked functional groups, such as amido, amino, carboxylic acid, hydroxy, or thiol group, to their surface. Illustrative linker molecules used in this capacity include, for example, $C_{2-18}$ carboxy-hydroxy compounds (such as citric or glycolic acid), $C_{2-18}$ dicarboxy-acids (such as hexanedioic or 1,10-decanedicarboxylic acid), $C_{2-18}$ carboxy-thiol compounds (such as 11-mercaptoundecanoic acid), $C_{2-18}$ carboxy-amine compounds (such as 6-aminohexanoic acid), $C_{2-18}$ carboxy-thiol compounds (such as thioglycolic acid or 3-mercaptopropionic acid), or $C_{2-18}$ diphosphonates (such as 1-hydroxyethane-1,2-diphosphonic acid). Such molecules may also include oligomers or polymers containing these types of amido, amino, carboxylic acid, hydroxy, or thiol groups. In doing so, the nanocrystals can be made to present one or more of these functional groups external to the nanocrystal surface. See for example, Seidmeier, A., et al., *Chem Soc. Rev.*, 2015, 44, 1526-1560, which is incorporated by reference for its methods of achieving such surface modifications and the specific modifications achieved. These exposed amido, amino, carboxylic acid, hydroxy, or thiol groups not only modify the hydrophilicity of the particles, improving or affecting their dispersibility in the photoactive compositions, but also provide points of attachment for linking these nanocrystals to the photoinitiators or prepolymers, through complementary functional groups on the latter species, thereby allowing tethering of the upconverting crystal to the photoinitiator, the prepolymer, or both.

In typical embodiments, the upconverting core-shell nanocrystals are present in the photoactivated compositions in a range of from about 0.1 to 0.5 wt %, 0.5 to 1 wt %, 1 to 1.5 wt %, 1.5 to 2 wt %, 2 to 2.5 wt %, 2.5 to 3 wt %, 3 to 3.5 wt %, 3.5 to 4 wt %, 4 to 5 wt %, or a combination derived from a combination of tow or more of these ranges, for example, from 0.5 to 1.5 wt %, relative to the weight of the entire photoactive composition.

UV-Vis Blockers

As described elsewhere herein, the present methods are directed to the use of NIR light to activate photoinitiators typically activated by UV-Vis light. While in place, the significant amounts of incident light are absorbed by either melanin or hemoglobin of the tissue in which the compositions are present, preventing activation by these photoinitiators. Nevertheless, in some cases, it is preferred to protect these photoinitiators from ambient light even further. In such cases, the use of additional UV-Vis-blockers is desirable. These UV-Vis-blockers, which may also be characterized as masking or absorbing compounds, are used to absorb or block incident UV-Vis light over a wavelength range that prevents the activation of the UV-Vis photoinitiator with ambient or superambient levels of UV-Visible light. Typically, such UV-Vis-blockers comprise one or more compounds each having extended conjugation. Optionally substituted derivatives of azobenzene, benzophenone, benzotriazole, or the like may be used in this capacity. Such UV blockers are described in U.S. Patent Application Publication Nos. 2017/0020658 and US2007/0055369, both of which are incorporated by reference herein, at least for their teaching of such UV-Vis blocking compositions.

These UV-Vis blockers may be usefully applied as distributed within the intraocular lenses, or preferably as layered spectral blockers, present on the "front" of the lens to block the lens from incident UV light from sun exposure. Likewise, to the extent that the upconverting core-shell nanoparticles emit UV-Vis light upon irradiation, it can also be useful to apply these UV-Vis blockers to the "back" of the lens, to protect the retina from emissions from the nanoparticles. Such front or back layers typically have thicknesses in a range of 0.001 to 250 microns. Such layers may be formed by applying a polymer layer onto at least one surface of the lens. The polymer layer contains the light absorbing material necessary to create the blocking zone or region. Any known method for applying a polymer layer may be used as long as it does not adversely affect the transmission of the desired wave-lengths.

Methods of Treatment—General Principles

To this point, the disclosure has focused on compositions and optical devices for use in intraocular lenses, but it should be appreciated that the disclosure also includes the methods of using these materials.

In specific aspects of the invention, the methods and compositions may be used for human patients, though the methods may be useful for other mammals, such as a horse, cow, dog, cat, goat, sheep, or pig, for example.

The methods of the present disclosure comprise a step of irradiating a light adjustable lens (LAL) or a photoactive composition with at least one wavelength of near infrared (NIR) light. The general parameters associated with "NIR light" are also defined elsewhere herein, but in certain more specific embodiments, the near infrared wavelength of light used in these methods is in a range of from 780 nm to 1020 nm. Preferably the selected wavelength coincides with the absorption maximum of the upconverting core-shell nanocrystal; more preferably, this is in a range of from 800 nm to 812 nm or from 960 nm to 1000 nm, more preferably 808 nm or 980 nm (e.g., for Tm-containing core-shell nanocrystals).

The duration of the exposure to this NIR light may be of any suitable kind so long as the target molecule(s) are activated from the light. In particular aspects, the light exposure is continuous, although in some cases it is intermittent. The specific duration depends, for example, on the nature of the light source and the concentrations of the ingredients in the light adjustable lens and/or photoactive composition. In certain preferred embodiments, the light is applied with a pulsed laser. Using pulsed illumination beams are attractive as they provide improvements in the relative intensities of the desirable peaks ca. 365 nm relative to less desirable peaks in the 400-800 nm visible region; i.e., increasing the up-conversion efficiency towards higher energy, lower wavelength emission bands. Pulsing also reduces patient exposure to the irradiating energies. Exemplary pulse durations include those with irradiative pulses less than 10 ms, less than 6 ms, less than 4 ms, less than 2 ms, less than 1 ms, less than 500 microsec, and less than 200 microsec. See, e.g., Deng, R. et al., *Nat. Nanotech.*, 2015, 10, 237-242 (which is incorporated by reference herein in its entirety, or at least for its description of this phenomenon, as well as representative pulse duration/frequency pairs). Pulsing the laser, at frequencies ranging from about 10 to 200 Hz, for example from about 15 to 120 Hz (ca. 1 pulse per 10 ms to 60 ms), allows higher doses of power to be delivered since there is a down time between each dose, potentially helping to prevent or reduce thermal damage normally associated from continuous wave laser exposures. Additionally, pulsing the laser may generate shifted emission spectra of the upconverting nanocrystals, by constructively aiding in the excited state light combination and helping to promote the higher energy, lower wavelength emission from the upconverting nanocrystals.

Exemplary light sources for NIR light irradiation include lamps, lasers, and light-emitting diodes (LED). Light is generally used at an intensity of 10 mW/cm$^2$ to 5 W/cm$^2$, preferably 1-2.5 W/cm$^2$, consistent with biological exposure limits, with the particular light intensity dependent on, among other factors, the tissues and photoinitiators compound(s) involved. Emissions quantum yield of these core-shell nanocrystals respond in an exponential fashion to increasing excitation power. Individual embodiments include those where the intensity is in a range of from 10 to 50 mW/cm$^2$, from 50 to 100 mW/cm$^2$, from 100 to 200 mW/cm$^2$, from 200 to 300 mW/cm$^2$, from 300 to 400 mW/cm$^2$, from 400 to 500 mW/cm$^2$, from 500 to 750 mW/cm$^2$, from 750 to 1000 mW/cm$^2$, from 1000 mW/cm$^2$ to 1250 mW/cm$^2$, from 1250 mW/cm$^2$ to 1500 mW/cm$^2$, from 1.5 W/cm$^2$ to 2 W/cm$^2$, from 2 W/cm$^2$ to 3 W/cm$^2$, from 3 W/cm$^2$ to 4 W/cm$^2$, from 4 W/cm$^2$ to 5 W/cm$^2$, or a range derived from the combination of two or more of these ranges, consistent with acceptable biological limits. One of skill in the art will readily be able to adjust light intensity and time of illumination for a particular application.

Treatments may be repeated in the individual as needed. For example, a second or more treatment may be applied within days of a previous treatment, within weeks of a previous treatment, or within months of a previous treatment.

Specific embodiments include the treatment of a patient having an ocular deformation condition. In specific embodiments, the ocular deformation condition comprises degenerative myopia, regular myopia and/or scleral staphylomas, glaucoma, normal tension glaucoma, and ocular hypertension. In some embodiments, the methods herein may be used prophylactically to reduce the risk of or prevent an ocular deformation condition including any of the foregoing. In other embodiments, the treatments are designed to correct or slow the progression of one or more of these conditions in a patient where the conditions already exist.

In an exemplary procedure, following insertion of the light adjustable lens or direct application of the respective photoactive composition, the eye is irradiated with NIR light for a time and under conditions sufficient to effect the desired change, the specific conditions depending on the nature of the treatment and specific composition of the irradiated material. Suitable modes of clinical implementation of irradiation include having the patient in a supine position and delivering light through an operating microscope or having the patient seated and delivering light using a slit lamp system. Because NIR light is used, the light may be delivered through the patient's pupil or other portion of the eye.

In independent embodiments, the directly applied photoactive composition or the lens may be irradiated entirely or in targeted areas. In separate embodiments, individual portions of the directly applied photoactive compositions may be irradiated separately, either positionally or temporally, or both. Irradiation may involve a patterned application of light. Suitable exemplary methods to control the irradiation pattern incident on the tissue include rastering the irradiation beam, using a spatial light modulator, using a digital mirror device, or using a fiber optic coupled to a laser. The amount of light exposure may also be changed to adjust the degree of polymerization or crosslinking that is occurring in the light adjustable lens. The exposure of the NIR light may directed to a particular region of the sclera or the light adjustable lens, as identified by diagnostic imaging. Exemplary diagnostic imaging techniques include ultrasound imaging, optical coherence tomography (OCT) imaging, OCT Doppler imaging, or magnetic resonance imaging (MRI).

Additionally, in separate embodiments, these methods further comprise determining that a change in optical properties is required or desired prior to treatment.

Further, any of these processes may be repeated, after waiting a suitable time to evaluate effect of the change of the properties. In the presence of the UV-Vis blocker, there may be no need to "lock in" the shape or properties, as the presence of the blocker compound will prevent further changes in the light adjustable lens until the element is further exposed to the NIR light of the proper frequency and sufficient intensity. This allows for future readjustments at a later time if further corrections are need. Where UV-Vis blocker not present, it may be useful to "lock-in" the shape or properties of the light adjustable lens with a more global application of the MR light.

Methods of Treatment—Irradiating Light Absorbing Lenses (LALs)

Some embodiments provide methods comprising irradiating a light adjustable lens (LAL) with a near infrared wavelength of light, the light adjustable lens comprising the composition of any one of the disclosed compositions described herein, wherein the irradiation of the light adjustable lens results in a change in a refractive property of the light adjustable lens. The light adjustable lens may or may not contain a separate photopolymerizable prepolymer, if the matrix material contains suitable functionality to crosslink. In certain of these embodiments, the lens is irradiated either as a whole or in targeted areas. In separate embodiments, individual portions of the lens may be irradiated separately, either positionally or temporally, or both. The exposure of the NIR light may directed to a region of the lens identified by diagnostic imaging. Exemplary diagnostic imaging techniques include ultrasound imaging, optical coherence tomography (OCT) imaging, OCT Doppler imaging, or magnetic resonance imaging (MM).

In specific embodiments, the methods comprise irradiating a light adjustable lens with a near infrared wavelength of light, the light adjustable lens comprising any of the compositions described elsewhere herein. The refractive property may be any property that effects the ability of the lens to pass light, for example, refractive index, distribution of fluid within the lens, shape, or local or total density of the material caused by the polymerization or crosslinking of the materials within the lens.

The composition and characteristics of the various components are described elsewhere, and these compositions and characteristics are equally applicable to these embodied methods. In addition, separate embodiments provide for the compositions which result from the treatment of the light adjustable lens with the NIR light; i.e., the compositions comprising a matrix polymer, a partially or completely polymerized prepolymer, and incorporating the upconverting nanocrystal(s).

In separate embodiments, the lens is implanted in the eye of a patient, e.g., as an intraocular lens, and additional embodiments include those steps of implanting the lens in the eye of a patient prior to irradiation.

Where the photopolymerizable prepolymers incorporated into the lens polymer matrix have photocleavable linkages, these materials provide additional options for subsequently altering the shapes and/or optical characteristics of the devices. For example, certain methods provide for irradiating the inventive optical hydrogel composition or devices with at least one suitable wavelength of light in a range of from about 200 nm to about 1 micron, with sufficient power and duration, so as to cleave at least a portion of the photocleavable linkages within a pre-determined volume of the hydrogel. Upon cleavage of these linkages, any water contained in the matrix is re-distributed within the hydrogel, in some cases providing three-dimensional pockets, channels, or layers of higher concentrations of water, resulting in a deformation of the shape, a change in the refractive index, or both deformation and change of refractive index of the of the composition or device, relative to its initial state. Alternatively, the photocleavage may relieve any stress associated with the original crosslinking of the prepolymers. In some cases, the irradiation may be applied by a laser of sufficient character that it can be done while the optical device is implanted in the patient. Preferably the laser is capable of providing a two or multi-photon light source. By effectively reversing the polymerization process by selectively photo-cleaving the cross-linker to precisely and selectively change the swelling in certain regions of the lens, which result in a change in the refractive power of the lens. The region with cleaved cross-likers is able to take up more water and since water and the matrix material have different refractive indices, this region of the lens will change power and the shape of the lens will change.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially" of. For those embodiments provided in terms of "consisting essentially of," the basic and novel characteristic(s) is the operability of the methods (or the compositions or devices derived therefrom) as providing a photochemically active compositions activated through the use of one or more upconverting nanocrystals. Materials or steps which do not detract from such operability would be considered within the scope of such embodiments.

It is also noted here that any comments or remarks made with respect to the core of a core-shell nanocrystal may equally be directed to a non-core-shell nanocrystal as separate embodiments. For example, the description of the use of Fe or other transition metal dopants to enhance the emissions in the region of 365 nm should not be interpreted as limited to this use in core-shell nanocrystals. Additional embodiments associated with these descriptions also include the use of Fe or other transition metal dopants in single phase nanocrystals (i.e., with no active "shells").

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

The use of brackets or parenthetical prefixes in describing chemical compounds may describe embodiments both where the bracketed content is present or absent, as is understood by the person of skill in the art. For example, the term "[meth]acrylate" refers to independent embodiments of both acrylate and methacrylate. Similarly, the term "[meth] acrylamide" refers to independent embodiments of both acrylamide and methacrylamide The term "biocompatible" as used herein refers to a compound or material that is not toxic or injurious to an individual patient or tissue.

The terms "crosslink" or "crosslinking" carry their normal meaning in its broadest sense, as readily used by a person of skill in the polymer or biochemical arts. It typically refers to formation of a covalent or other bond (e.g., hydrogen bond) between two molecules, typically between two oligomers, macromers, or polymers. For example, a collagen molecule may be crosslinked to other collagen molecules to form a network of interlinked collagen molecules held together by a covalent linkages.

In the context of the present disclosure, the terms "intraocular lens," "lens," "light adjustable lens," and "light adjustable intraocular lens," unless otherwise specified, are used interchangeably.

The terms "nanoparticle(s)" and "nanocrystal(s)" may generally be used interchangeably herein as both refer to nanocrystals having at least one dimension in the range from 1 nm to 250 nm. Such nanomaterials may be shaped as cubes, ellipsoids, platelets, rods, or spheres. In such cases, it is more typical (but not necessarily) that the at least one dimension is characterized as a range of from 1 to 5 nm, from 5 to 10 nm, from 10 to 15 nm, from 15 to 20 nm, from 20 to 25 nm, from 25 to 30 nm, from 30 to 35 nm, from 35 to 40 nm, from 40 to 50 nm, from 50 to 100 nm, from 100 to 150 nm, from 150 to 200 nm, and from 200 to 250 nm, or characterized by a range encompassing two or more of these ranges, for example from 10 nm to 20 nm. When used in lenses, such as intraocular lenses, the dimensions are preferably less than about 100 nm, more preferably less than 50 nm, to avoid specular scatter of incoming light and associated bluriness by the patient. Within these parameters, for nanocrystals used in intraocular lenses, the nanocrystalline cores typically has a maximum dimension in a range of from 25 nm to 75 nm, preferably about 50 nm, with each shell layer ranging from 2 nm to 10 nm. Larger nanoparticles have individual dimensions that are proportionately larger.

"Optional" or "optionally" means that the subsequently described circumstance may or may not occur, so that the description includes instances where the circumstance occurs and instances where it does not. Similarly, embodiments which refer to an ingredient or step as being "optionally present," those embodiments include separate independent embodiments in which the step or ingredient is present or absent. For example, the phrase "optionally deformable" means that a hydrogel may or may not actually deform (at least to any perceptible extent), despite a redistribution of water within the hydrogel following irradiation. Thus, the description "optional" allows for, but does not require, the optional condition to occur.

As used herein, the term "photoactive composition" refers to a composition that is activated by the irradiation with near infrared (NIR) light and comprises at least a UV-Vis photoinitiator and an at least one type of upconverting crystal. The term is used to describe independent embodiments where the composition does or does not further contain a photopolymerizable prepolymer. The term "photoactive direct treatment composition" is used to describe a photoactive composition which does not contain any an added photopolymerizable prepolymer material.

The terms "photoinitiator" and especially "UV-Vis photoinitiator" as used herein refer to a compound or a moiety capable of converting absorbed light energy, generally or especially UV or visible light, into chemical energy in the form of initiating species, e.g., free radicals or cations, that activate polymerization or crosslinking of specific functional groups on the polymer precursors.

The terms "photopolymerize" or "photopolymerizable" carries its normal connotations as understood by the person of skill in the art as referring to the ability of a material to be activated by light, in the instant case, by the actions of a photoinitiator and in turn polymerize, copolymerize, or crosslink with other suitable materials. In some embodiments, the photopolymerization comprises polymerization, copolymerization, or crosslinking with another photopolymerizable prepolymers, substituted photoinitiators, functionalize upconverting core-shell nanocrystals, or subunits thereof, polymerization, copolymerization, or crosslinking with a molecule of the sclera, or both. In the present context, photopolymerizable prepolymers do not polymerize in the absence of a suitable chemical initiator, either separate from the prepolymer or matrix or incorporated therein; i.e., in the absence of such a photoinitiator, they do not polymerize even in the presence of light.

The terms "polyethylene glycol" and "PEG" as used herein refers to a compound comprising more than one partial or whole poly(ethylene-glycol) backbone monomer of ethylene-glycol with or without differing endgroups and also comprising some or no other monomers such as, for example, dimethyl siloxane, methyl methacrylate, lysine, arginine, chondroitin sulfate, keratin sulfate, etc. In specific embodiments, it is defined as an oligomer or a polymer comprising the repeated units of ethylene glycol ($-OCH_2CH_2-$). Prepolymers described in terms of a particular backbone (e.g., PEG, protein, etc.), where the backbone does not contain a polymerizable moiety or moieties typically contain terminal groups capable of serving this purpose. Exemplary polymerizable moieties are described elsewhere herein.

The term "prepolymer" refers to a compound capable of polymerizing, copolymerizing, or crosslinking with another prepolymer, wherein each prepolymer is similarly or complementarily functionalized to achieve these reactions. In some cases, the prepolymer is a monomer, oligomer, or macromer containing one or more functional groups capable of polymerizing, copolymerizing, or crosslinking with another prepolymer. In some aspects, even macromers or polymers containing suitable functional groups making them suitable for crosslinking with other polymers or with lower monomer, oligomer, macromers, or crosslinking agents are considered prepolymers. In still other aspects, a photoinitiator (or a nanocrystal) may contain a functional group capable of participating in polymerization, copolymerization, or crosslinking reactions, in which case the photoinitiator (or nanocrystal) may be considered to be both the prepolymer and the photoinitiator (or nanocrystal). In some embodiments, the prepolymer may additionally comprise a crosslinking compound to crosslink, for example, added crosslinkable polymer or with compositions already present within the sclera. Individual crosslinking molecules that are directly active (e.g., glyceraldehydes) or are activated using UV-Vis light are known in the art.

The term "transition metal" is used as understood by this skilled in the art to include one or more d-block elements. As used herein, the term is distinguished from the lanthanide elements by inclusion of Group 4-12 elements. Exemplary transition metals contemplated herein include Ti, V, Cr, Mn, Fe, Co, Ni, Cu, Zn, Zr, Nb, Mo, Ru, Rh, Pd, Ag, Cd, Hf, Ta, W, Re, Os, Ir, Pt, and/or Au.

"Upconversion" or "upconverting" refers to a property of certain lanthanide nanoparticles to exhibit an anti-Stokes emission, in which lower energy photons are converted to higher energy photons based on long-lived energy states in the inner f-orbitals of certain lanthanide ions. Using NIR light for excitation avoids photodamage of tissue, avoids background fluorescence of biological tissue, and provides for deeper penetration into the tissue.

The term "UV-Visible light" as used herein refers to electromagnetic radiation having a wavelength in a range of from about 200 nm to about 750 nm. Individual embodiments describing UV-Visible light as an important parameter include those in which the range of wavelengths include one or more ranges encompassing 200 to 250 nm, 250 to 300 nm, 300 to 350 nm, 350 to 400 nm, 400 to 450 nm, 450 to 500 nm, 500 to 550 nm, 550 to 600 nm, 600 to 650 nm, 650 to 700 nm, and/or 700 to 750 nm. The term "near infrared light" or "NIR light" refers to electromagnetic radiation in a range of from about 750 nm to about 1400 nm. Individual embodiments describing NIR light as am important parameter include those in which the range of wavelengths include one or more ranges encompassing 750 to 800 nm, 800 to 850 nm, 850 to 900 nm, 900 to 950 nm, 950 to 1000 nm, 1000 to 1050 nm, 1050 to 1100 nm, 1100 to 1200 nm, 1200 to 1300 nm, and/or 1300 to 1400 nm. It should be appreciated that reference to the irradiation by NIR light or by a wavelength of near infrared (NIR) light, as used herein, is intended to connote that the irradiation includes only, or practically only, NIR light; that is, the irradiating light is devoid of any UV-Visible light wavelength capable of activating a UV-Vis photoinitiator, or at least the specific UV-Vis photoinitiator used in the given photoactive composition.

The following listing of embodiments in intended to complement, rather than displace or supersede, the previous descriptions.

Embodiment 1

An optical device comprising:
(a) a photopolymerizable prepolymer;
(b) a UV-Vis photoinitiator;
(c) at least one upconverting core-shell nanocrystal; and
(d) optionally a UV-Vis blocker;
wherein the light adjustable intraocular lens further optionally comprises a polymer matrix in which the photopolymerizable prepolymer material, the UV-Vis photoinitiator, the optional UV-Vis blocker, and the at least one upconverting nanocrystal are distributed. For suitability of purpose, the intraocular lens is transparent or practically transparent.

In certain Aspects of this Embodiment, the optical device is a light adjustable intraocular lens, preferably comprising the polymer matrix. The following Embodiments which describe the light adjustable intraocular lens, unless otherwise indicated, should be read also in terms of the more general optical device as well as the light adjustable intraocular lens as separate Embodiments.

In certain Aspects of this Embodiment, the polymer matrix in which the photopolymerizable prepolymer material, the UV-Vis photoinitiator, the optional UV-Vis blocker, and the at least one upconverting nanocrystal are distributed is present. In other Aspects, the polymer matrix is absent. The polymer matrix may comprise polymerized [meth]acrylate groups. The polymer matrix may be hydrophilic or hydrophobic. The polymer matrix may further comprise water in a range of from 1 wt % to 2 wt %, from 2 wt % to 3 wt %, from 3 wt % to 4 wt %, from 4 wt % to 5 wt %, from 5 wt % to 7 wt %, from 7 wt % to 10 wt %, from 10 wt % to 20 wt %, from 20 wt % to 30 wt %, from 30 wt % to 40 wt %, from 40 wt % to 45 wt %, from 45 wt % to 50 wt %, or a be present in a range defined by two or more of these ranges, relative to the weight of the polymer matrix.

In independent Aspects of this Embodiment, the optional photopolymerizable prepolymer is present. In other independent Aspects of this Embodiments, the optional photopolymerizable prepolymer is absent. The subsequent Embodiments which describe the photopolymerizable prepolymer, unless otherwise indicated, should be read that the photopolymerizable prepolymer is present. Additionally, the subsequent Embodiments should be read as describing independent embodiments where the photopolymerizable prepolymer is separately both absent and present.

Embodiment 2

The light adjustable intraocular lens of Embodiment 1, wherein the photopolymerizable prepolymer comprises a polyethylene glycol (PEG), a poly[alkyl or dialkyl]siloxane, a poly[meth]acrylate, a poly(amino acid), a poly(amino acid)-copolymer, a polycarbohydrate, a protein, or a polysaccharide backbone.

Embodiment 3

Light adjustable intraocular lens of Embodiment 1 or 2, wherein the photopolymerizable prepolymer comprises an acrylate, methacrylate (i.e., [meth]acrylates), acrylamide, methacrylamide (i.e., [meth]acrylamide), allyloxy, cinnamoyl, vinyl, terminal vinyl ether, N-vinyl carbazole, lactone, lactam, cyclic ether (e.g., epoxy), cyclic acetal, cyclic siloxane groups, or a combination thereof. In other Aspects, the photopolymerizable prepolymer may also include a cross-linkable groups such as an acetoxy, alkoxy, amino, anhydride, aryloxy, carboxy, enoxy, epoxy, halide, isocyano, olefinic, or oxine group.

Embodiment 4

The light adjustable intraocular lens of Embodiments 2, wherein the polysaccharide comprises poly(hyaluronic acid), dermatansulfate, chondroitinsulfate or keratansulfate.

Embodiment 5

The light adjustable intraocular lens of Embodiment 2, wherein the protein is a native or engineered elastin. Where the elastin is an engineered elastin, it has therefor one or more natural amino acid substitutions suitable for polymerization. Alternatively or additionally, the engineered elastin may further or instead comprises one or more non-natural amino acids comprising one or more chemical groups that are appropriate for polymerization, for photoinitiation, or both]

Embodiment 6

The light adjustable intraocular lens of any one of Embodiments 1 to 5, wherein the photoinitiator is a Type I or a Type II photoinitiator.

Embodiment 7

The light adjustable intraocular lens of any one of Embodiments 1 to 6, wherein the photoinitator absorbs light in a range of from 250 nm to 600 nm. In certain Aspects of this Embodiment, the photoinitator absorbs light in a range of from 300 nm to 400 nm. In certain specific Aspects of this Embodiment, the photoinitator exhibits and absorption maximum in range of from 350 nm to 450 nm ("blue range", preferably 360 nm to 370 nm) or in a range of from 450 nm to 600 nm ("red range")]

Embodiment 8

The light adjustable intraocular lens of any one of Embodiments 1 to 7, wherein the photoinitiator comprises an acetophenone, a benzophenone, a benzoin ether, a benzil ketal, an α-dialkoxyacetophenone, an alkylphenone, an α-hydroxyalkylphenone, an α-aminoalkylphenone, a xanthone, or a thioxanthone moiety.

Embodiment 9

The light adjustable intraocular lens of any one of Embodiments 1 to 8, wherein the photoinitiator comprises at least one of an acetophenone, anisoin, an anthraquinone, a sodium salt of anthraquinone-2-sulfonic acid, benzil, benzoin, a benzoin ether (e.g., ethyl, methyl, isopropyl, isobutyl ether), benzophenone, 3 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone, 3,4-dimethylbenzophenone, eosinY, 4'-ethoxyacetophenone, 2-ethylanthraquinone, fluorescein, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-mercaptothioxanthone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, or a thioxanthen-9-one.

Embodiment 10

The light adjustable intraocular lens of any one of Embodiments 1 to 9, wherein at least one type of upconverting core-shell nanocrystal comprises:

(a) a nanocrystalline core comprising a lanthanide sensitizer capable of absorbing light in a range of from 780 nm to 1020 nm and having at least one emission peak in the range of from 250 nm to 500 nm;

(b) at least one activating shell superposed on the nanocrystalline core, the shell comprising at least one lanthanide activator; and (c) an optically an inert outer layer superposed over the at least one activating shell.

In certain Aspects of this Embodiment, the absorption wavelength of the at least one type of upconverting core-shell nanocrystal is the target of laser excitation. In other Aspects, the at least one emission peak is matched to the absorption maximum of the photoinitiator. In certain other Aspects, the at least one type of upconverting core-shell nanocrystal is in the form of a hexagonal platelet.

Embodiment 11

The light adjustable intraocular lens of any one of Embodiments 1 to 10, wherein the nanocrystalline core comprises one or more of Er, Gd, Ho, Tm, Y, or Yb.

Embodiment 12

The light adjustable intraocular lens of Embodiment 10 or 11, wherein the nanocrystalline core comprises transition metal ions. In certain Aspects of this Embodiment, the transition metal comprises Co, Fe, Ti, Zr, and/or Hf.

Embodiment 13

The light adjustable intraocular lens of any one of Embodiments 11 to 13, wherein the nanocrystalline core comprises Tm, Er, Fe, or combination thereof.

Embodiment 14

The light adjustable intraocular lens of any one of Embodiments 10 to 13, wherein the nanocrystalline core comprises a $NaGdF_4$, $NaLuF_4$, $LiYF_4$, $NaYF_4$, $KYF_4$, $KYb_2F_7$, $BaF_2$, $CaF_2$, $SrF_2$, $LaF_3$, $YF_3$, $BaYF_5$, $BaGdF_5$, $KY_3F_{10}$, YOF, LuOF, or GdOF host doped with one or more of Er, Fe, Gd, Ho, Tm, Y, or Yb. Typically, the dopants are present as their trications, for example as $Er^{3+}$, $Fe^{3+}$, $Gd^{3+}$, $Tm^{3+}$, $Y^{3+}$, or $Yb^{3+}$.

In other Aspects of this Embodiment, the dopants may further comprise other lanthanides, for example comprising Pr, Nd, Sm, Eu, Gd, Tb, and/or Dy.

Embodiment 15

The light adjustable intraocular lens of any one of Embodiments 10 to 14, wherein the nanocrystalline core comprises a host doped with one or more of (i) Er or Tm and (ii) Yb ($NaYF_4$:Yb, Er/Tm). In certain preferred Aspects of this Embodiment, the core is doped with Y, Yb, and Tm.

Embodiment 16

The light adjustable intraocular lens of any one of Embodiments 1 to 15, wherein the at least one lanthanide activator comprises Gd, Nd, Yb, Eu, Tb, Dy, and/or Sm. In preferred Aspects of this Embodiment, the at least one lanthanide activator comprises Gd, Nd, and/or Yb.

Embodiment 17

The light adjustable intraocular lens of any one of Embodiments 1 to 16, wherein the at least one shell of the core-shell nanoparticle contains Nd.

Embodiment 18

The light adjustable intraocular lens of any one of Embodiments 11 to 17, wherein the optically inert outer layer comprises yttrium, a $C_{6-24}$ saturated or unsaturated fatty acid, an optionally functionalized silicate polymer coating (e.g., mesoporous silica), or a alkali metal fluoride or alkaline earth metal fluoride (e.g., $CaF_2$).

Embodiment 19

The photoactive composition of any one of Embodiments 1 to 18, wherein a portion of the at least one type of upconverting core-shell nanocrystal is surface modified to present an amino, carboxylic acid, hydroxy, or thiol group, or a combination thereof. In certain Aspects of this Embodiments, the at least one type of upconverting nanocrystal is tethered to at least one of the photoinitiators by coupling a functional group on the photoinitiator with the presented functional group of the surface modified upconverting nanocrystal.

Embodiment 20

The photoactive composition of any one of Embodiments 1 to 19, further comprising a UV-Vis blocker. In certain Aspects of this Embodiment, the UV-Vis blocker is a benzotriazole compound.

Embodiment 21

The light adjustable intraocular lens of any one of Embodiments 1 to 20, further comprising a UV blocking front/back layer for the light adjustable intraocular lens. The UV blocking layer should be sufficient to reduce potential retinal exposure to upconverted radiation, emitted by the upconverting core-shell nanoparticles.

Embodiment 22

A method of adjusting the optical properties of the light adjustable intraocular lens of any one of Embodiments 1 to 21, the method comprising irradiating the light adjustable intraocular lens with a near infrared wavelength of light, wherein the irradiation of the light adjustable lens results in a change in a refractive property of the light adjustable intraocular lens.

Embodiment 23

The method of claim 22, wherein the near infrared wavelength of light is applied with a laser, preferably a pulsed laser. In certain Aspects of this Embodiment, the laser provides a power in a range of from 1 $W/cm^2$ to 5 $W/cm^2$, preferably 1-2.5 $W/cm^2$, consistent with biological exposure limits. In certain independent Aspects of this Embodiment, the laser can be applied continuously or in a pulsed manner.

Embodiment 24

The method of Embodiment 22 or 23, wherein the near infrared wavelength of light is in a range of from 780 nm to 1020 nm.

Embodiment 25

The method of any one of Embodiments 22 to 24, wherein the light adjustable intraocular lens is implanted in an eye of a patient prior to irradiation.

Embodiment 26

The method of any one of Embodiments 22 to 25, wherein the refractive property of the light adjustable intraocular lens is refractive index, distribution of fluid, shape, or local or total density, or two or more of these properties of the light adjustable intraocular lens.

Embodiment 279

The method of any one of Embodiments 22 to 26, further comprising determining that a change in optical properties is required or desired.

EXAMPLES

The following Examples are provided to illustrate some of the concepts described within this disclosure. While each Example provided in the text or in the figures is considered to provide a specific individual embodiment of composition or methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1. Synthesis and Characterization of Upconverting Nanoparticles (UCNPs)

Example 1.1. Procedure for the Synthesis of Upconverting Core-Shell Nanocrystals

Example 1.1.1. Single Composition Nanocrystals

The following procedure outlines the synthesis of Thulium (Tm) doped Yttrium (Y)/Ytterbium (Yb) upconverting nanoparticles and is general for the synthesis of other co-doped upconverting nanoparticles. It should be appreciated that other lanthanide doped nanoparticles may be prepared by analogous procedures. See, for example, Boyer, J.-C.; Vetrone, F. Cucciam L. A.; Capobianco, J. A. *J. Am. Chem. Soc.* 2006, 128, 7444-7445; and Li, Z.; Zhang, Y. *Nanotechnology* 2008, 19, 345606, which are incorporated herein for their teaching of these materials and methods of preparing such materials.

The lanthanide oxides were first converted to their trifluoroacetate (TFA) salts. To a 3-necked flask equipped with a dean-stark trap was added $Y_2O_3$ (220.2 mg, 0.975 mmol), $Yb_2O_3$ (98.5 mg, 0.25 mmol), and $Tm_2O_3$ (9.6 mg, 0.025 mmol). To this was added 10 mL of a 50% (v/v) solution of trifluoroacetic acid (TFA) in $H_2O$. The reaction mixture was heated to 80° C. and allowed to stir for 30 min until the solution became homogenous. At this point, the reaction temperature was reduced to 50° C. and the mixture allowed to stir under a stream of argon until complete evaporation of the TFA and water.

The reaction flask was purged with a steady stream of argon for 10 min. To the reaction mixture was added sodium trifluoroacetate (0.34 g. 2.5 mmol), oleic acid (20 mL) and 1-octadecene (20 mL) under a constant pressure of argon. The solution was heated to 100° C. for 1 hr until a homogenous suspension was observed. The reaction was slowly heated to 300° C. and maintained at this temperature for 1 hr. The reaction vessel was slowly cooled to room temperature. Ethanol (100 mL) was added and the particles isolated by centrifugation. The particles were washed with ethanol (15 mL), and collected by centrifugation. This was repeated 3 more times to afford a slightly viscous white powder.

Example 1.1.2. Synthesis of Core-Shell Nanoparticles

A thermolysis approach using lanthanide trifluoroacetate (TFA) salt precursors was used to generate up-converting nanoparticles of varying sizes, layering, and compositions. The metal salts were synthesized from their cheaper metal oxides and were mixed to give specific ratios of the elements to be included. This facile approach allowed for quick and controlled changes when constructing the nanoparticles. In addition, the "shell" TFA salt precursors could be and was prepared in separate flasks that are then added at high temperatures to the "core" nanoparticle in the central pot. This gave added complexity by controlling compositions for each layer of the nanoparticles and significantly decreased synthetic time of the particles because isolation of the particles are not needed before addition of the next layer. This procedure was used to produce an array of nanocrystals of varying sizes, compositions, and constructions.

In addition, another method involving lanthanide chloride salt precursors was used to generate "core" particles. This method allowed for the use of a variety of chloride salts from commercial sources that could be used without further purification. Again, particle size was tuned by varying starting ratios of salts to solvent, and the particles were grown via thermolysis. This approach also allowed for easier doping of other elements into the nanocrystals, such as Fe', which were otherwise not amendable to the TFA salt procedure above. The resulting "core" particles were then subjected to layering via TFA salt procedure. Combining the two methods allowed for the successful generation, for example, of thulium-doped upconverting core-shell nanocrystals that were activatable either by 808 nm or 980 nm light sources.

TFA Salt Preparation:

Lanthanide oxides were processed either homogeneously or as mixtures in the desired ratios of the components. In one embodiment, the mixture was refluxed at 105° C. in 1:1 de-ionized ("DI") water to redistilled trifluoroacetic acid for two hours. The solution was filtered hot to remove any undissolved material. Solvent was removed under reduced pressure and the product was dried and stored for further use. This method provided the desired metal trifluoroacetate salt used in the thermolysis synthesis. A 4 mmol oxide reactant total yielded between 3.5-4 g and could be stored at room temperature. For example, a desired molar ratio of 99.5:0.05 ytterbium (Yb) to thulium (Tm) is weighed out to a total of 4 mmol (3.96 mmol Yb and 0.04 mmol Tm) and mixed with 25 mL of DI water and 25 mL of trifluoroacetic acid. This mixture was refluxed at 105° C. for two hours and then filtered hot. Any remaining water and trifluoroacetic acid was removed via a roto-evaporation and then further dried on a high vacuum line for a minimum of 4 hours. Product yields were between 3.5-4 g and the product was stored at room temperature.

Yttrium trifluoroacetate hydrate is available through Sigma-Aldrich and behaved well in the nanoparticle synthesis. It is a suitable replacement for making the TFA salt in the laboratory.

Upconverting Core-Shell Nanocrystals Core@Shell@:

Syntheses were carried out by having a central "core" flask with subsequent desired "shells" in separate flasks to be added in a specific order. These starting materials must be properly prepared before particle growth to ensure uniform growth and stability. Each flask contained a combination of lanthanide TFA salts, sodium TFA (or calcium TFA), oleic acid, and 1-octadecene. Each mixture was heated to 100° C. under vacuum for 30-60 min and then back-filled with argon. This removed water and oxygen from the mixture while simultaneously forming the oleate complexes. The starting material must be completely dissolved in order to have proper synthetic particle growth. Once under argon, the "shell" flasks were maintained at a temperature<150° C. in preparation to be added to the central "core" flask. Ratios of reactants were varied according to desired particle outcomes. Exemplary lanthanide:sodium TFA ratios included 1:1, 1:2, or 1:4. Increasing the sodium content increase the particle size but, in some cases, had a negative effect on higher upconversion emissions. This was most prominently seen for thulium (Tm) doping. The other important ratio is the total amount of TFA salts to the amount of oleic acid 1-octadecene. Decreasing the amount of the solvent relative to the TFA salts (i.e., higher concentrations of the solutes) generated larger particles. Conversely, increasing the amount of solvent resulted in smaller particles. A 1:10 molar ratio of total TFA salt to oleic acid typically generated particles in the range of 20-40 nm while a 1:5 ratio typically generated particles in the 180-250 nm range. Oleic acid and 1-octadecene were generally kept in a 1:1 volume ratio but in some cases were adjusted to also effect particle size. Increasing 1-octadecene diluted the oleate precursors further, again resulting in smaller particles. Lowering the 1-octadiene content results in more concentrated solutions, resulting in larger particles. By systematically adjusting these parameters, it was possible to provide particles that varied in diameter from 20 nm to 500 nm. The "core" flask—under argon now—were typically heated to temperatures of 300-320° C. at a rate of 10° C./min. Once at the desired temperature, they were maintained there for 30-90 min. By holding the solutions at temperatures above 300° C., it was possible to generate hexagonally shaped nanoparticles, having the preferred morphology for higher energy emission.

Hold times and temperatures also effected particle size. Higher temperatures and longer times produce larger particle growth compared to lower temperatures and shorter times. Longer hold times also resulted in better particle uniformity.

After the "core" of the particle was formed, the "shell" (devoid of oxygen and water and under argon atmosphere) was transferred to the "core" flask while at its elevated temperature (>300° C.). The material was added slowly so not to drop the "core" temperature to <280° C. In some cases, the "shell" was added in two steps as necessary. Incubation times of 30-60 min were appropriate post "shell" additions to allow for proper layer growth on the "core" particles. The "core" particles acted as seeds, allowing the added "shell" material to preferentially grows onto the particles already in the reaction rather than spontaneously forming new particles. Dropping the internal temperature too low caused an undesirable increase in the amount of unseeded nanoparticle growth. By repeating this process, several layers could be added until the designed particle was formed. In this way, particles having between 1 shell and 6 shells were prepared (though the most common construction had 3-4 shells). Following completion of the syntheses, the reaction was cooled to room temperature naturally and precipitated with ethanol or acetone. the resulting nanocrystals were collected by centrifuge and subsequently washed 2-4 times with more ethanol by re-dispersing in the solvent and then centrifuging down to collect. The resulting particles were either stored as the wet material or dried with an argon stream for 30-60 min and re-dispersed in cyclohexane or chloroform for storage and further use. The collected nanocrystals were coated in oleic acid, where the carboxylic head is the ligand associated with the particle while the hydrophobic tail interacts with the surrounding solvent.

Chloride Salts:

The synthesis described by Gnanasammandhan et al. (*Nature Protocols*, 2016, 11, 688-713) was used, with minor changes to fit the desired ending particle. The amount and ratio of oleic acid and 1-octadecene was adjusted to alter the final particle size. Core elements and their ratios needed proper adjustment from their stock chloride salt solutions in water. The storage solutions included chloroform, cyclohexane, or toluene.

Stock solutions are made by dissolving metal chloride salt hydrates in deionized water. A total of 1 mmol of salts were mixed in desired ratios by pipetting desired volumes into a 250 mL 3-necked flask. The thermocouple is attached (touching the glass) and the temperature was set to 110° C. to drive off the water. Oleic acid (6 mL) and 1-octadecene (15 mL) were added at temperature; this ratio of solvents led to upconverting core-shell nanocrystals in the 20-30 nm range size. The temperature was typically increased to 140° C. for 30 minutes or until all the material fully dissolved to form the oleate complex. The reaction mixture was cooled to 60° C. and 5 mL of methanol containing 2.5 mmol sodium hydroxide and 4 mmol ammonium fluoride were added slowly. The reaction vessel was heated to 110° C. for 20 min to drive off the methanol. After the methanol had boiled away, the reaction was put under vacuum for 10 min and then cycled three times between argon and vacuum before finally back filling with argon. The reaction was heated to 300-320° C. for 60 min to form hexagonal nanocrystals, cooled to room temperature and precipitated out using equal volume of acetone to the total solvent in the reaction. After centrifugation, the pellet was dissolved in cyclohexane, chloroform, or toluene for future use. The collected nanocrystals were coated in oleic acid.

Ligand Modification: Silica Coating Upconverting Core-Shell Nanocrystals S:

A reverse micro-emulsion technique proved successful in coating both large (200-250 nm) and small (<50 nm) particles with silica. The smaller particles formed more uniform silica layers and we are easier to analyze by TEM. The larger particles were harder to keep suspended for silica coating, making them less uniform and harder to clean and handle. The larger particles tended to crash out of the reaction mixture faster and form more small (<20 nm), empty silica particles. However, where a silica layer formed on larger particles, the particles more readily re-dispersed in water or ethanol. Particles dissolved in cyclohexane were diluted further into cyclohexane along with Triton X-100, 1-octanol, water, and tetraethyl orthosilicate. These reagents were allowed to equilibrate for 2 hours before adding ammonium hydroxide, which catalyzed the formation of silica for the particles. The particles were stirred for two days at room temperature to ensure full conversion to the silica coating. In some cases, additional tetraethyl orthosilicate was added over this time. Where done, the particles were left to incubate for at least 24 hr incubation after the last dose before recovery. At the completion of this incubation, the reaction was quenched with ethanol and acetone to precipitate the particles. The silica coated nanocrystals were collected by centrifuge and subsequently washed 2-3 times with 1:1 ethanol:DI water. Again, they were dispersed in the wash and then centrifuging down to collect. The resulting nanocrystals were dried with an argon stream for 30-60 min and re-dispersed in water or ethanol for further use.

Figure 4:
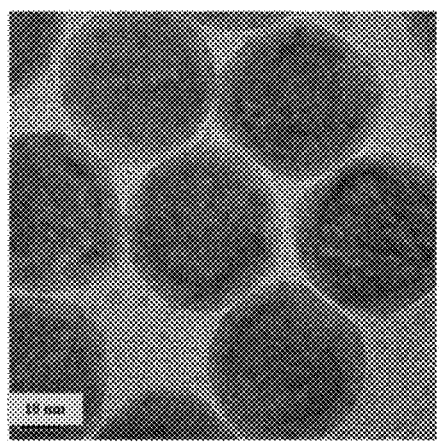
FIG. 4 shows a TEM micrograph of an upconverting core-shell nanocrystal coated with oleic acid (top) and silica, $SiO_2$ (bottom)
Figure 4:
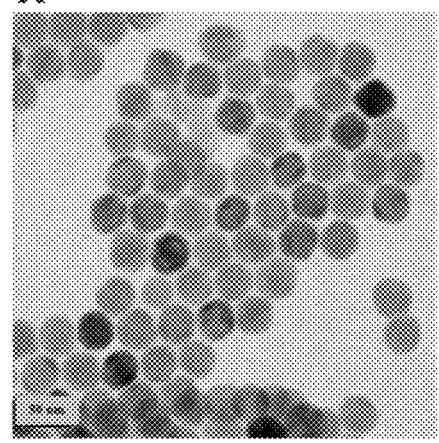
Figure 4:
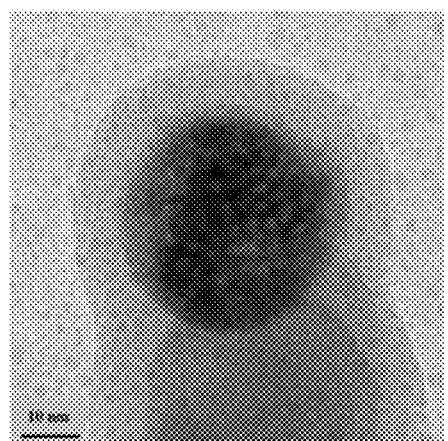
Figure 4:
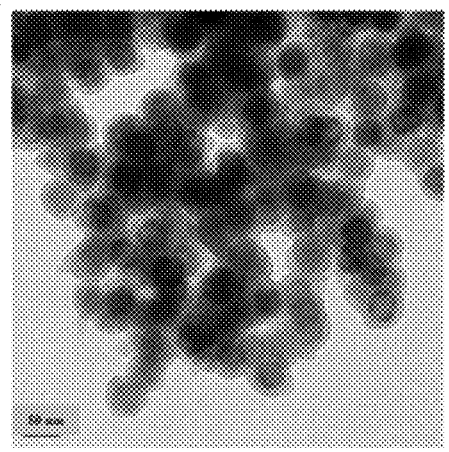

FIG. 4 shows the TEM results of coating nanocrystals with various coatings. In these cases, a reverse micro-emulsion technique using triton X-100 as the detergent was useful in helping deposit a silica layer on both small and large Tm-doped nanocrystals. TEM bright field images showed a new layer growth on the original particles. Layer thickness were controlled by controlling the amount of starting tetraethyl orthosilicate that was present in the reaction.

Example 1.2. Characterization of the Upconverting Core-Shell Nanocrystals s

Transmission electron microscopy (TEM) was performed in the Caltech Center for Applied Physics and Materials using an FEI Tecnai F30ST (300 kV) equipped with a high angle annular dark field detector, an Oxford ultra-thin window EDS detector and a Gatan Ultra Scan 1000XP camera.

A small amount of sample (~5 mg) was dispersed in 5 mL of chloroform using sonication to give an approximate 0.1 wt % solution. One drop of the resulting nanoparticle dispersion was dropcasted onto a carbon film supported on a 300 mesh copper grid and allowed to dry in air at room temperature.

Example 2. Representative Results

Exemplary results for particles prepared as described elsewhere herein are shown in FIGS. 5 to 10.

Figure 5:
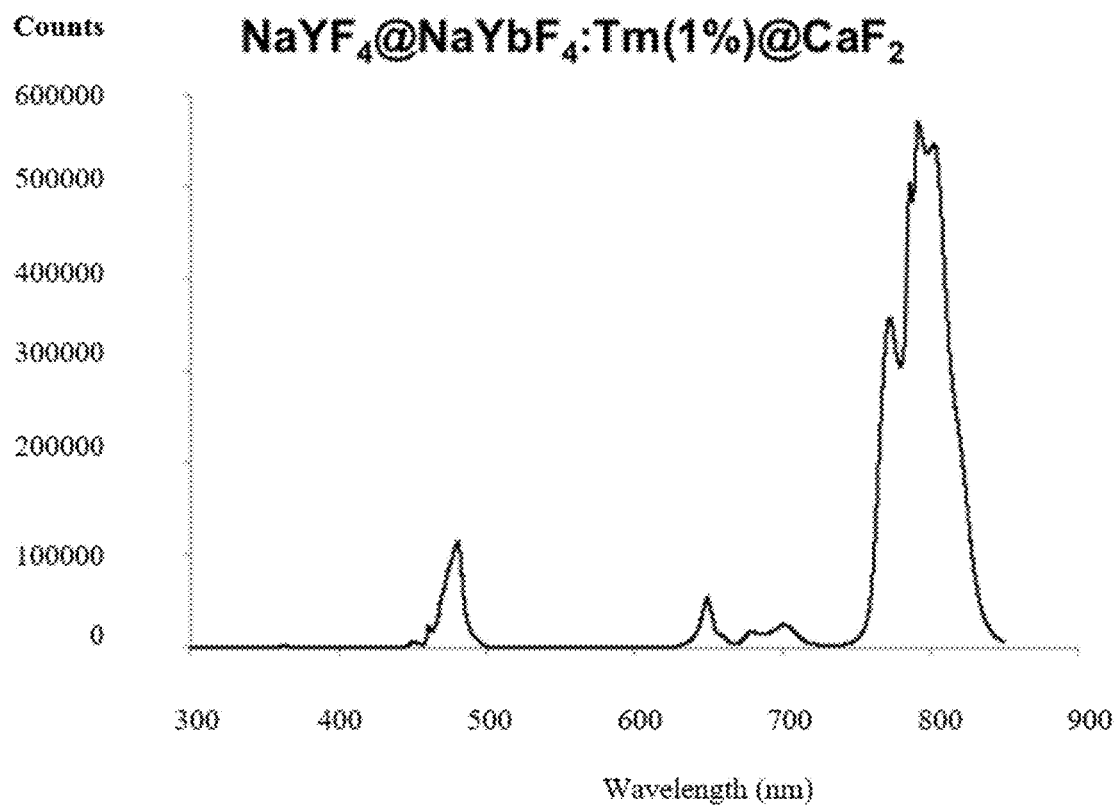
FIG. 5 shows alternative construction and compositions for tuning the emission spectra of upconverting core-shell nanocrystals. These particles were hexagonal and vary in diameter of ~20-50 nm. The nanocrystal size diameters are tunable to ranges in the 100 nm, 200 nm, and 250 nm.

FIG. 5 shows alternative construction and compositions for tuning the emission spectra of the upconverting core-shell nanocrystals. Modifications to the original up-converting core-shell nanocrystal synthesis resulted in a modular protocol that allows for facile addition of specific shell compositions to the nanocrystals and substitution of the emitter dopant to tune emission bands. These particles were hexagonal and varied in diameter of ~20-50 nm. The nanocrystal size diameters were tuned to ranges in the 100 nm, 200 nm, and 250 nm.

Figure 6:
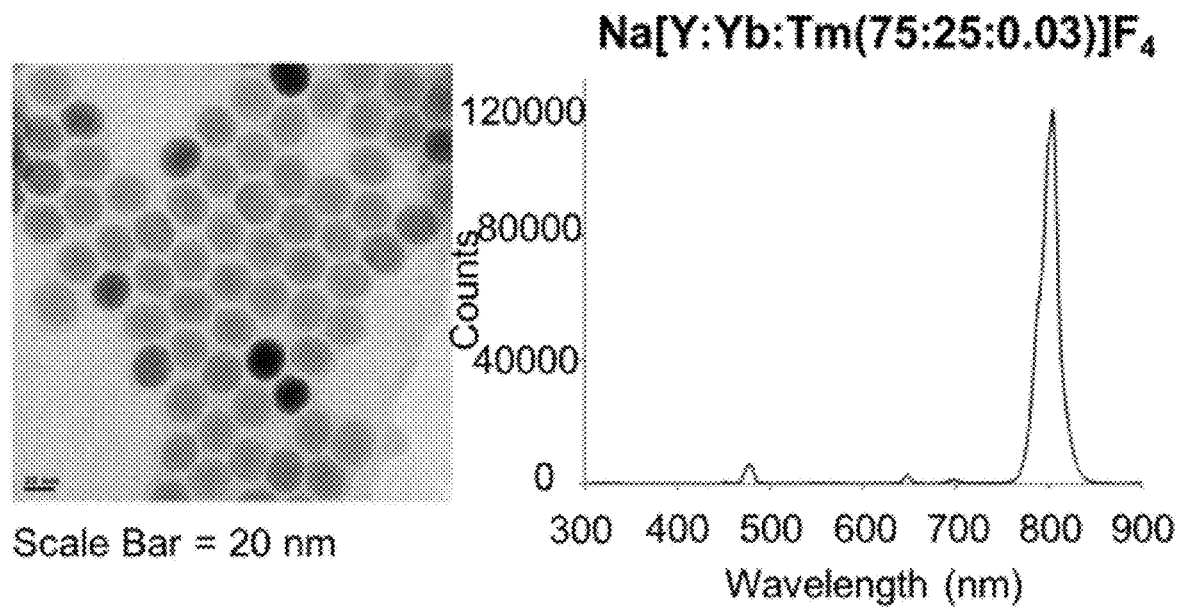
FIG. 6 shows transmission electron micrographs and emission spectra of upconverting core-shell nanoparticles prepared by methods disclosed herein.
Figure 6:
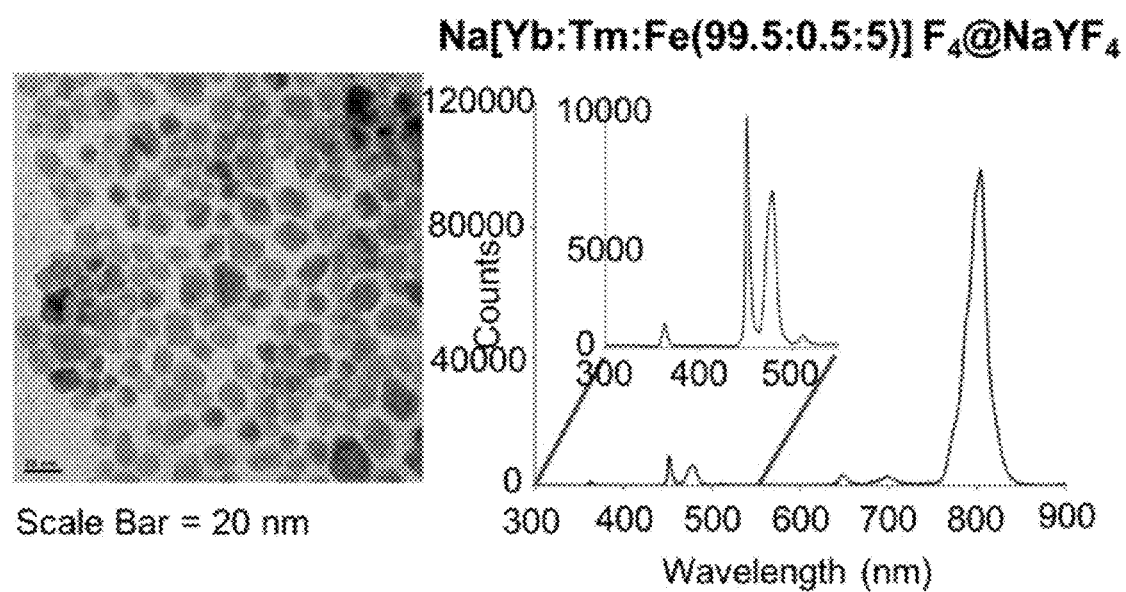
Figure 7:
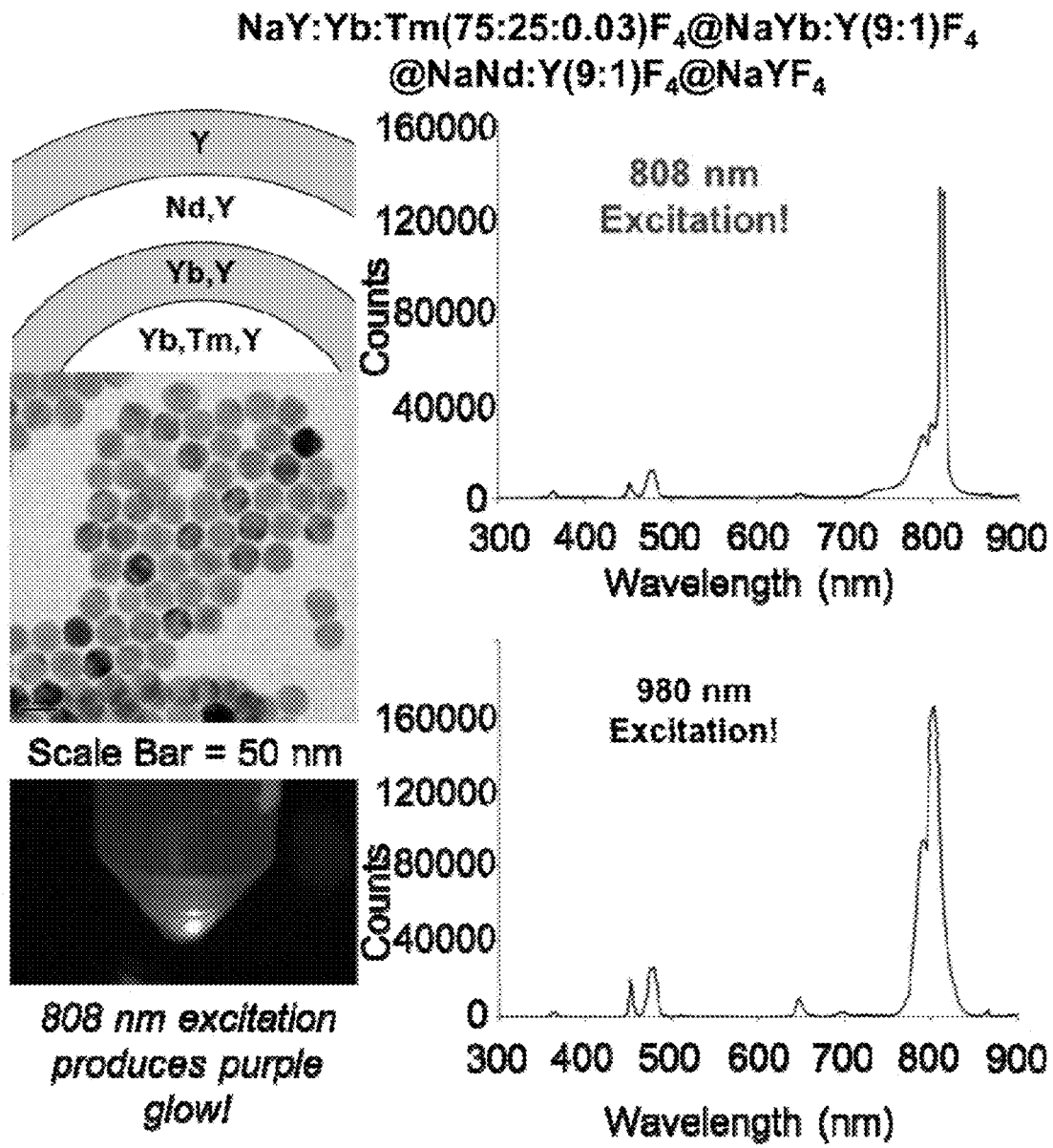
FIG. 7 shows effect of inclusion of Tm in the core to allow for the excitation at 808 nm using method described herein.
Figure 8A:
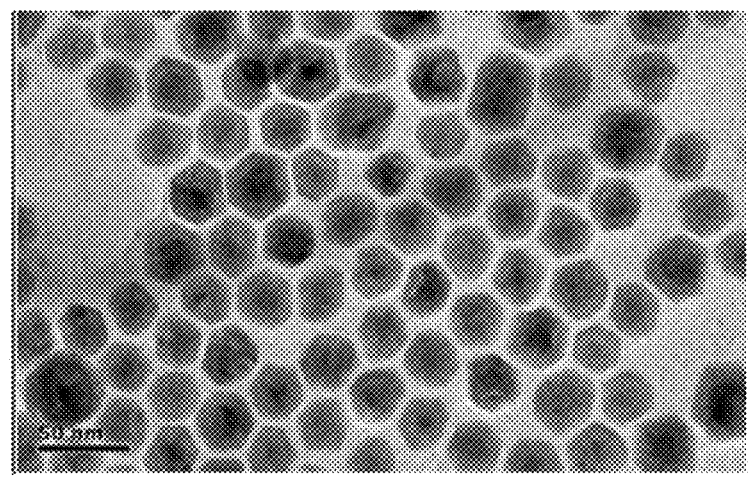
FIGS. 8A-D show results of changing compositions to allow for excitation at 808 nm.
Figure 8A:
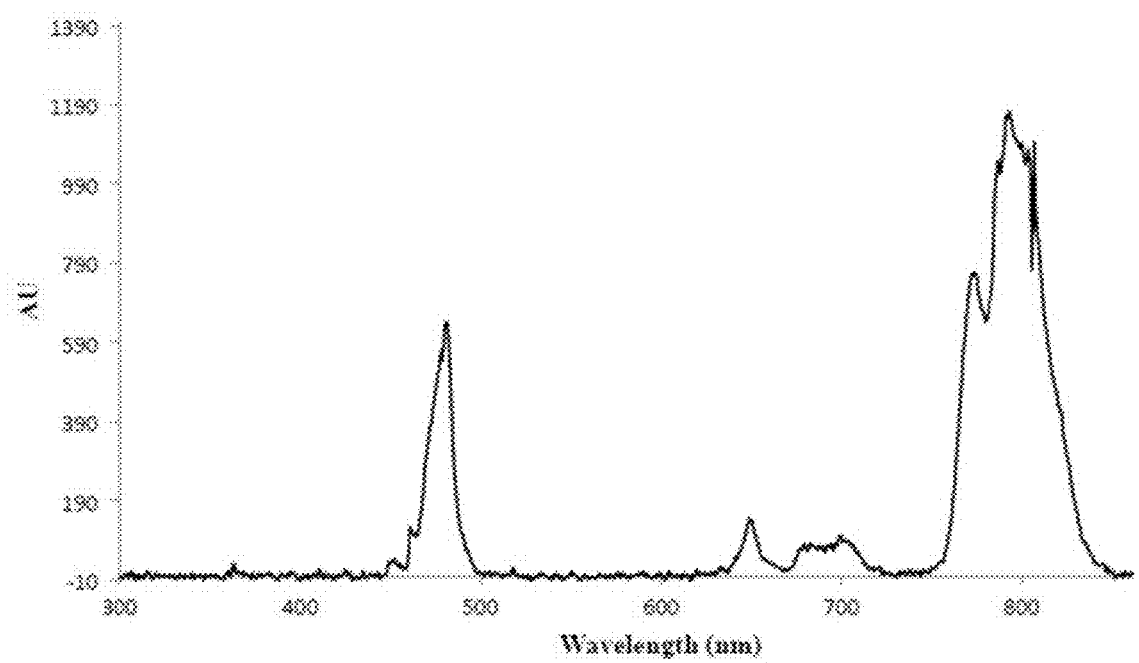
Figure 8A:
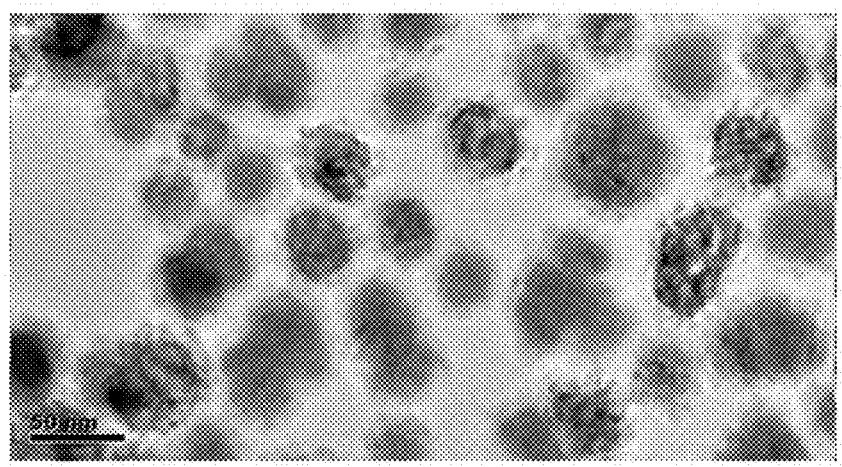
Figure 8A:
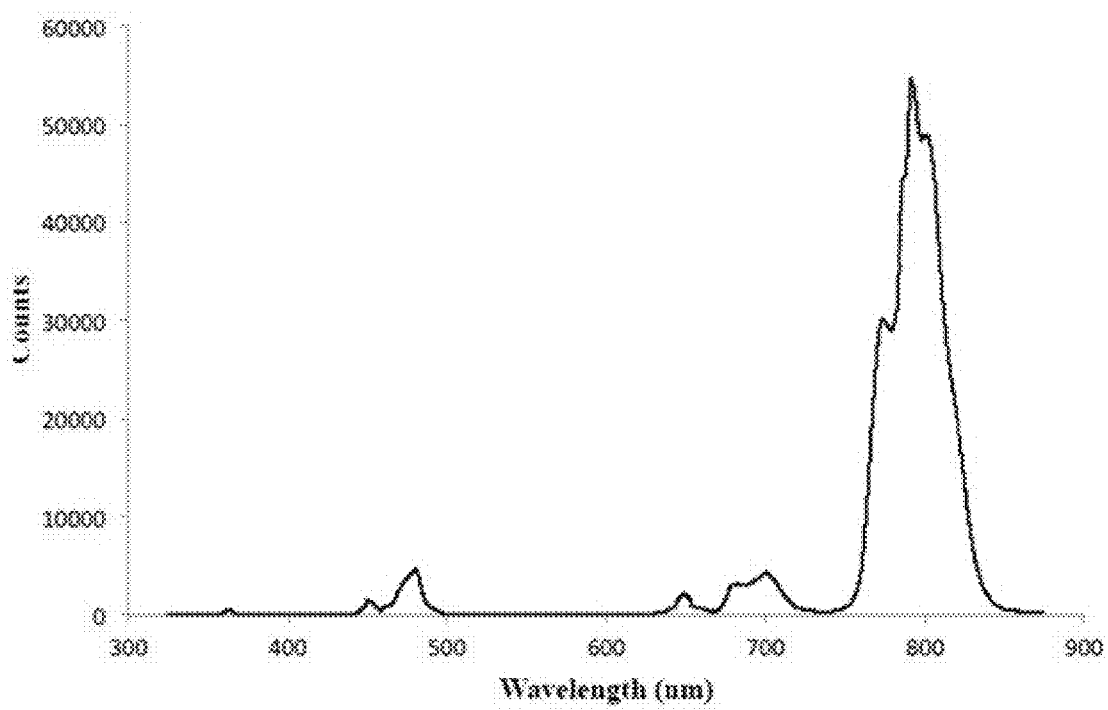
Figure 8A:
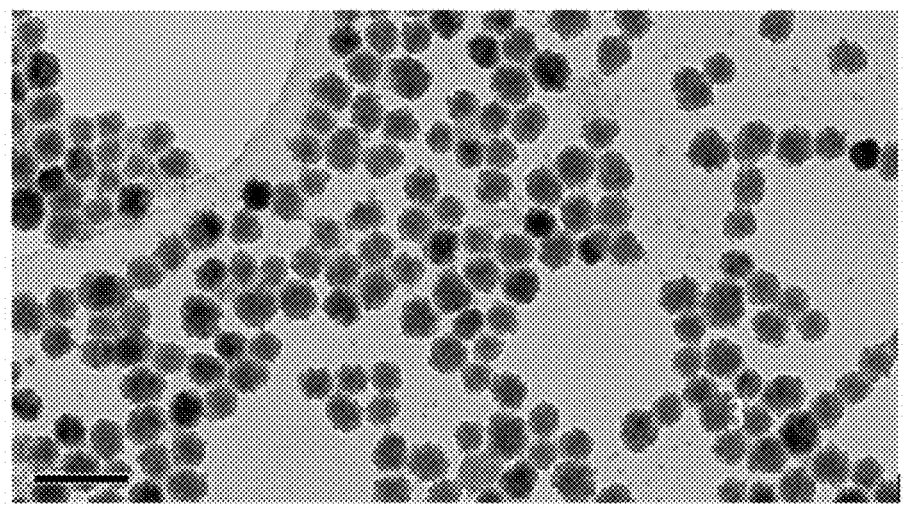
Figure 8A:
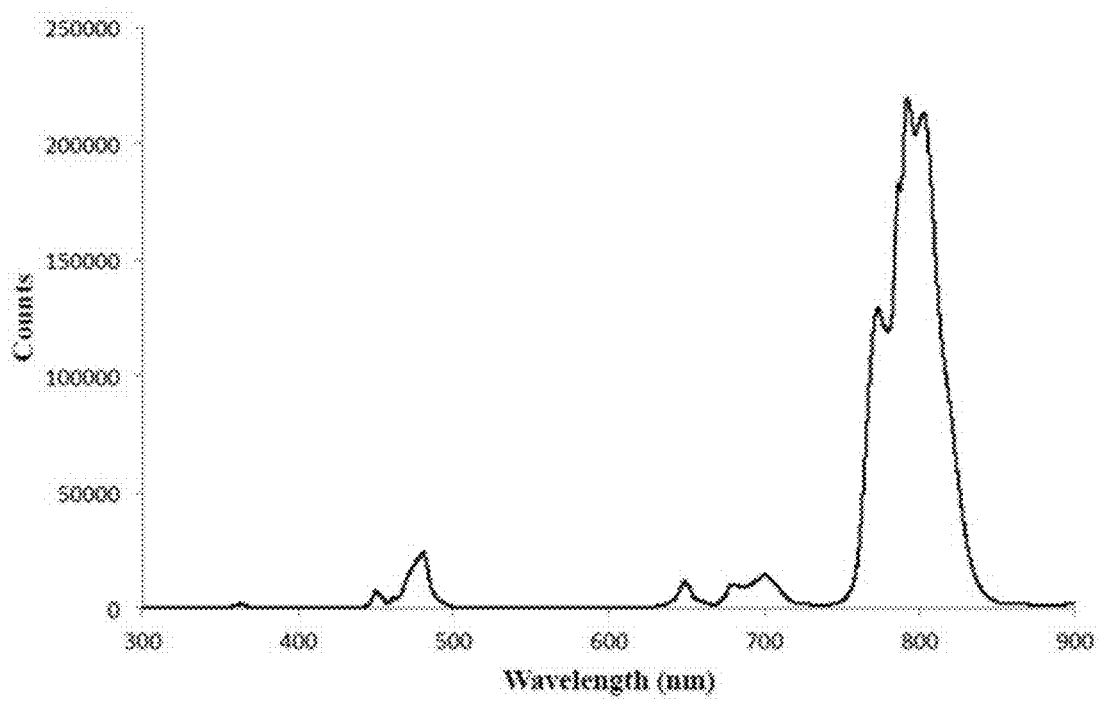
Figure 8B:
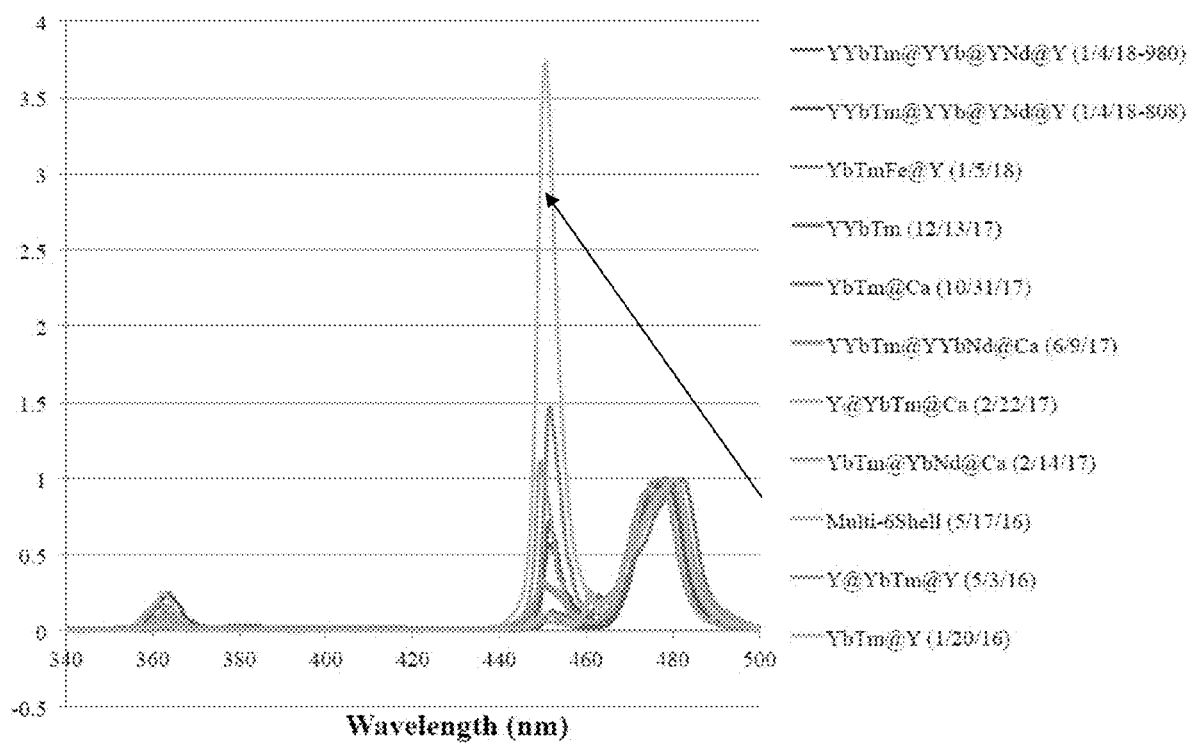
Figure 8C:
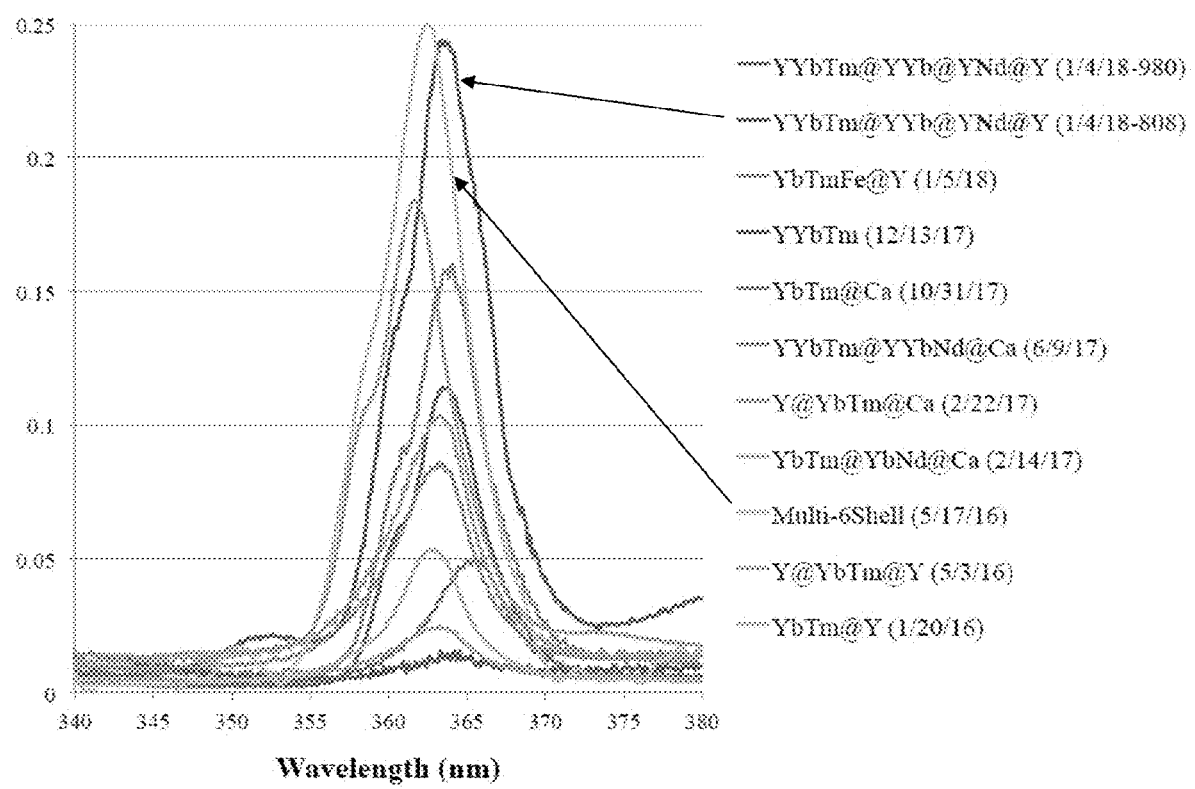
Figure 8D:
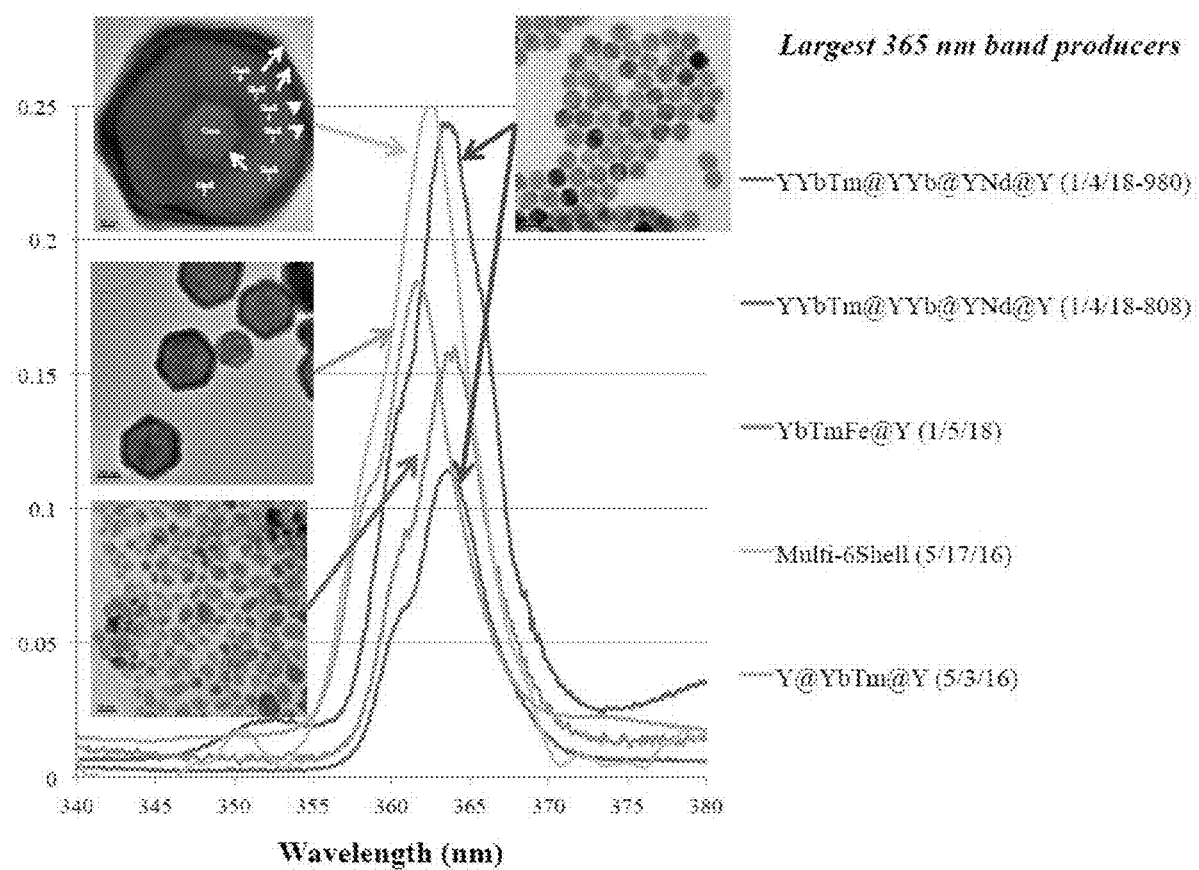

Several exemplary results are shown in FIG. 6 and FIG. 7. In each case, the core was prepared using chloride salt precursors, with subsequent layers being applied using the TFA salt method. In both cases, the high uniformity of crystal sizes was readily apparent. FIG. 6 provides a comparison of the effect of Fe in the core. The presence of an outer protecting shell enhanced the emissions at 365 nm for the Fe doped material (e.g., the relatively small emission at 365 nm in the top image of FIG. 6 was due to the lack of an outer protecting shell. Both the top and bottom images in FIG. 6 have were doped with Fe in the core). What is noteworthy here is the large emission band at 365 nm that is not seen in the same particle construction without the Fe dopant.

The results in FIG. 7 show the effect of the Nd layer. Here again, the core of the particle was made with the chloride salt synthesis, while the subsequent layers were deposited via the TFA salt synthesis. By adjustment of the composition through the use of a Nd coating layer, which absorbs strongly around 810 nm, and doping of Tm in the core, it was possible to construct a core-shell nanocrystal that could be activated by either an 808 nm or 980 nm excitation. A bright purple spot was seen with both excitation sources by eye.

FIGS. 8A-D show results of changing compositions to allow for excitation at 808 nm.

Figure 9:
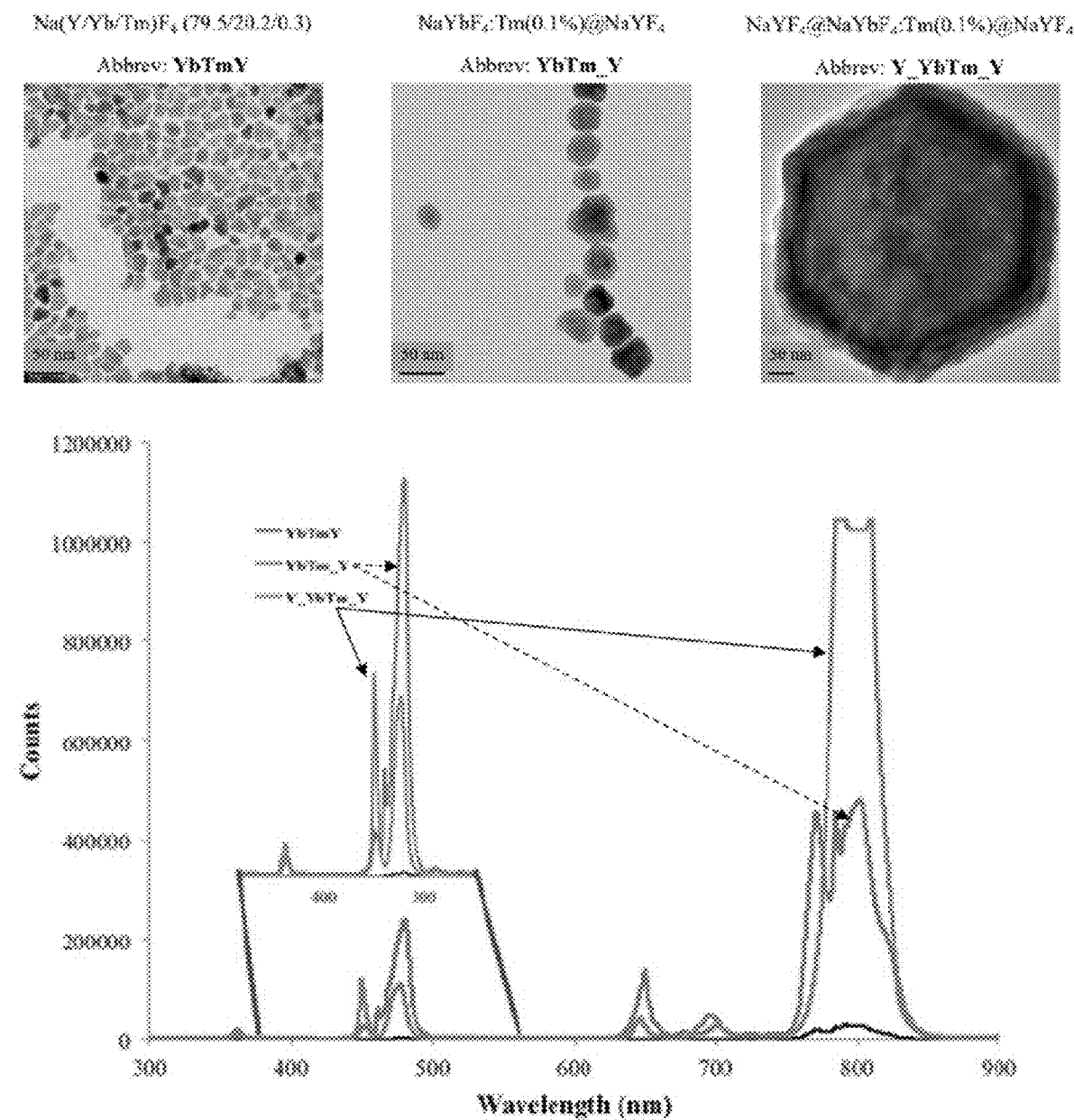
FIG. 9 shows the effect of an outer inert layer on the overall brightness of nanocrystal emissions.

FIG. 9 shows the effect of an outer inert shell ($NaYF_4$) on overall brightness of the nanoparticle emissions. Not only does such a coating increases the overall brightness of the nanoparticles (seen in the increase in fluorescence counts, but it also promotes formation of higher energy, lower wavelength photon emissions. The construction types are as followed (from left to right): Core, Core@Shell, and Core@Shell@Shell. The Core@Shell@Shell has an inert core and outer shell relegating the active up-converting layer to the middle layer. This too promotes a shift in emission bands towards higher energy, lower wavelength photons. For the emission comparison (FIG. 9, bottom image), particles were kept at the same concentration (except the Core which was at 2× concentration) and recorded under the same parameters in succession.

Figure 10:
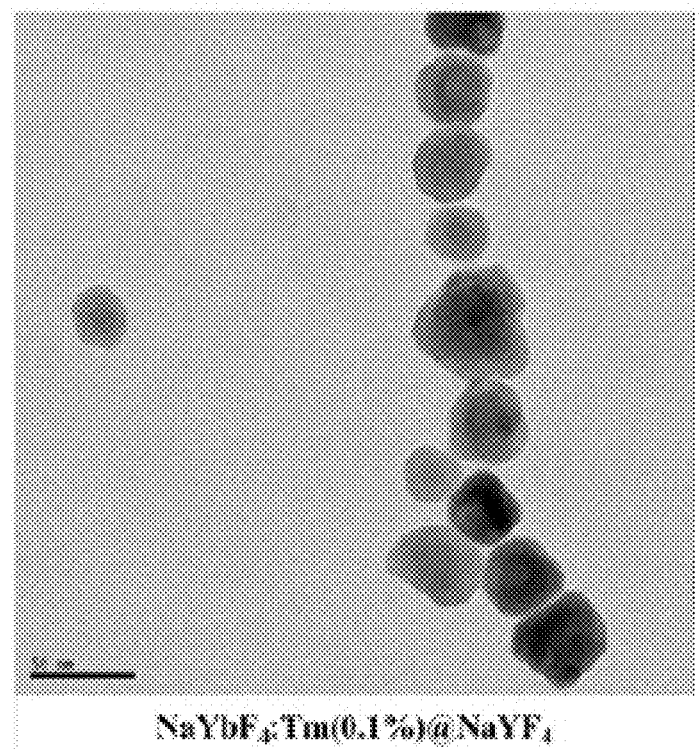
FIG. 10 shows the effect of nanoparticle size and the number of layers on the emission spectra of upconverting core-shell nanocrystals comprising Tm-containing cores.
Figure 10:
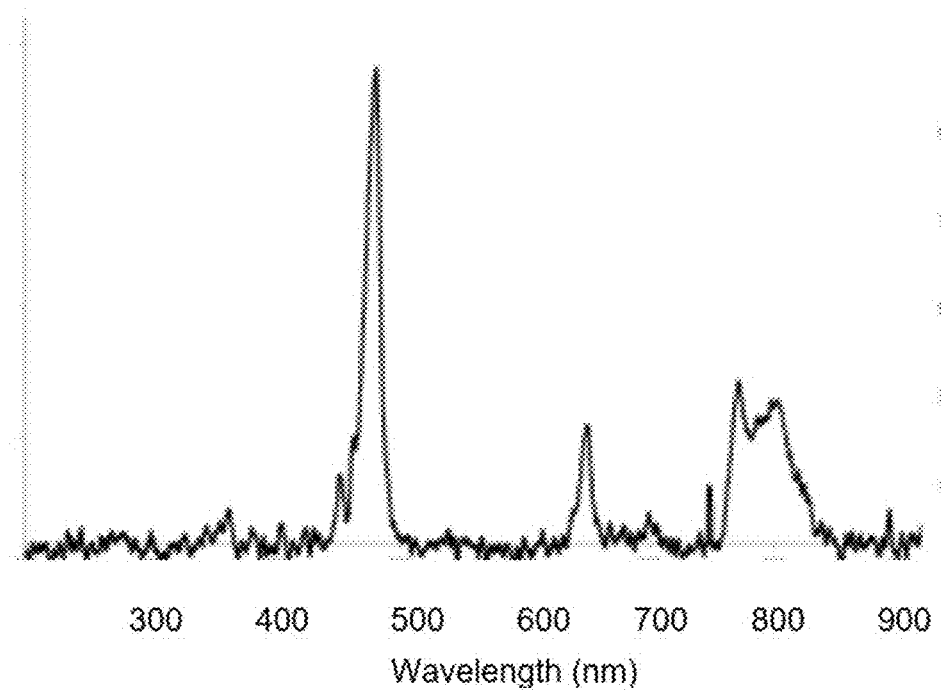
Figure 10:
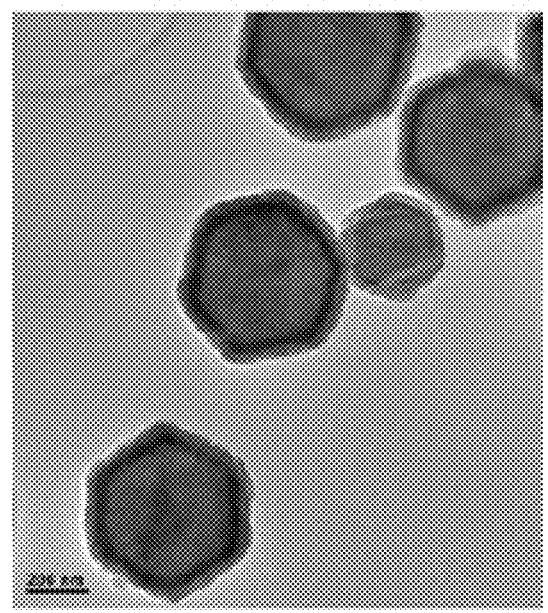
Figure 10:
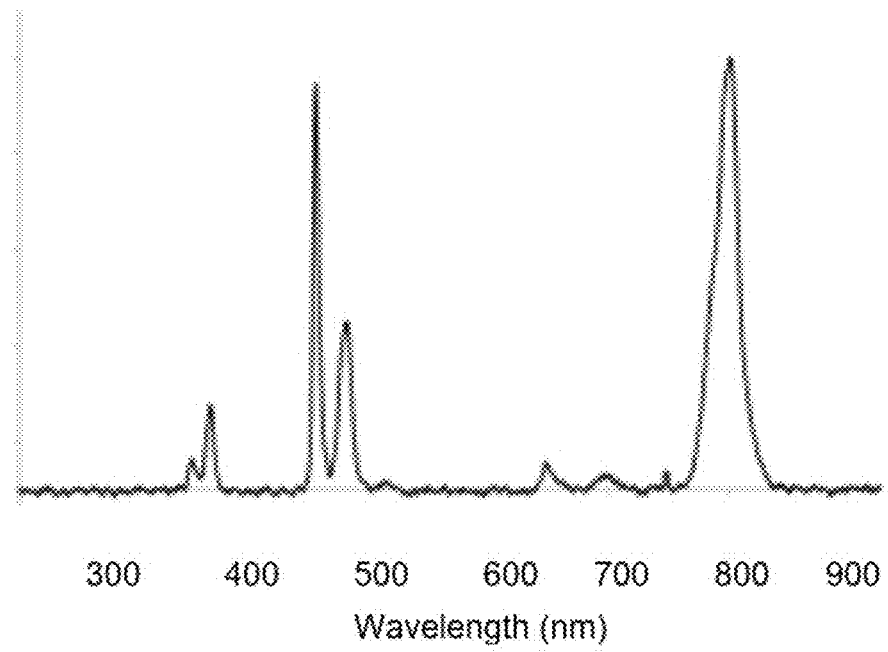
Figure 10:
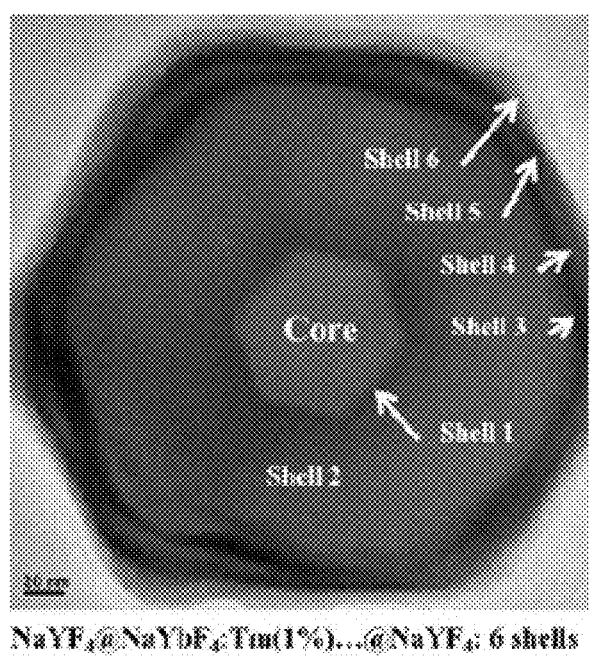
Figure 10:
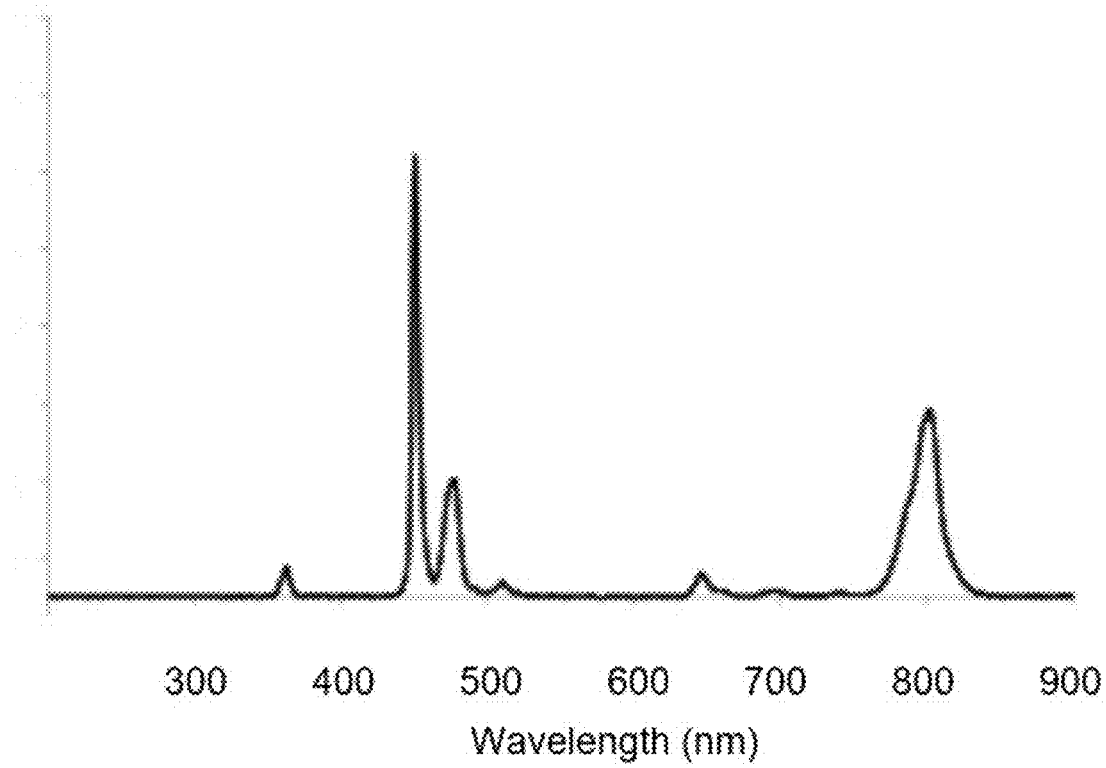
Figure 10:
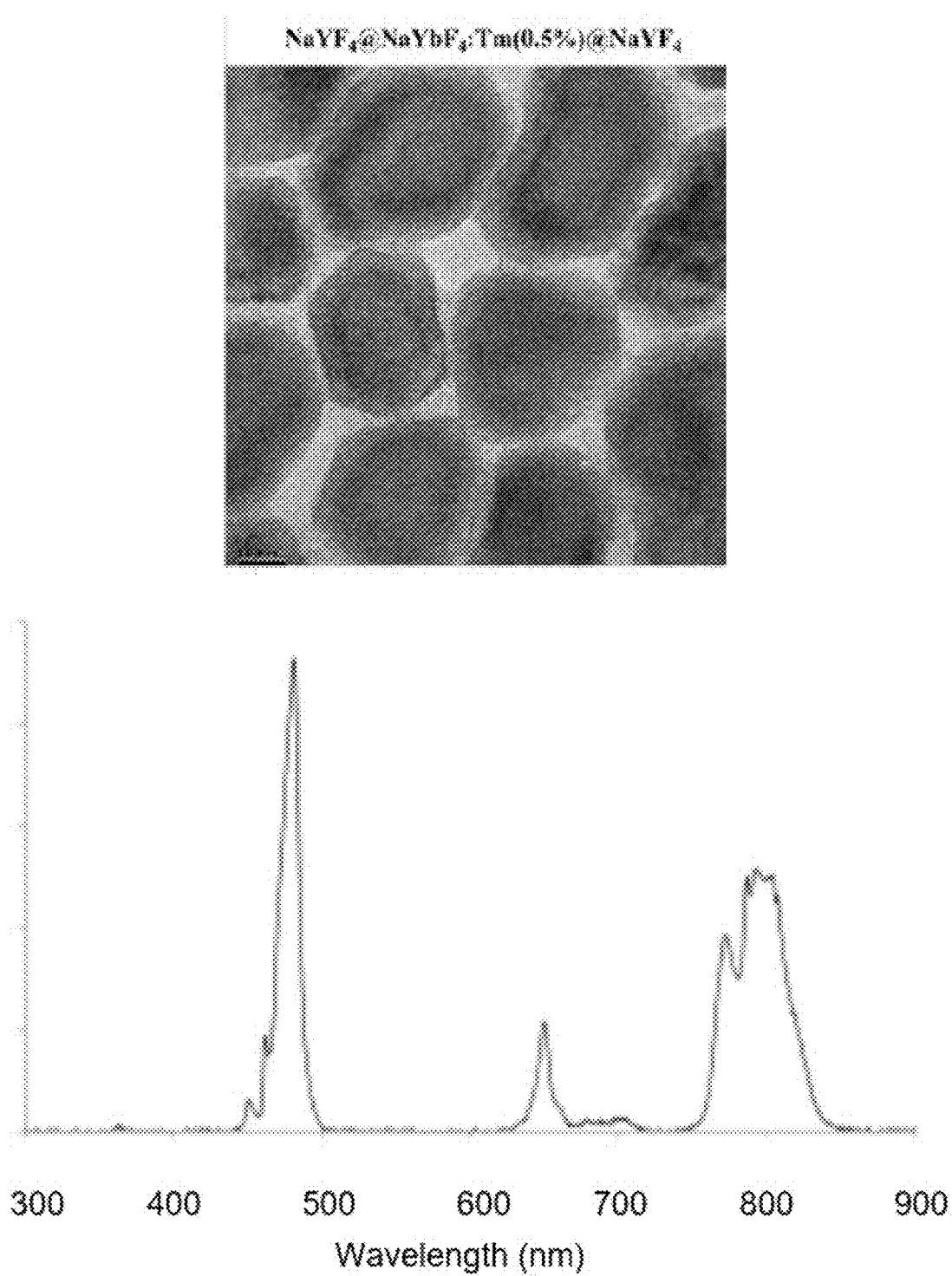
Figure 10:
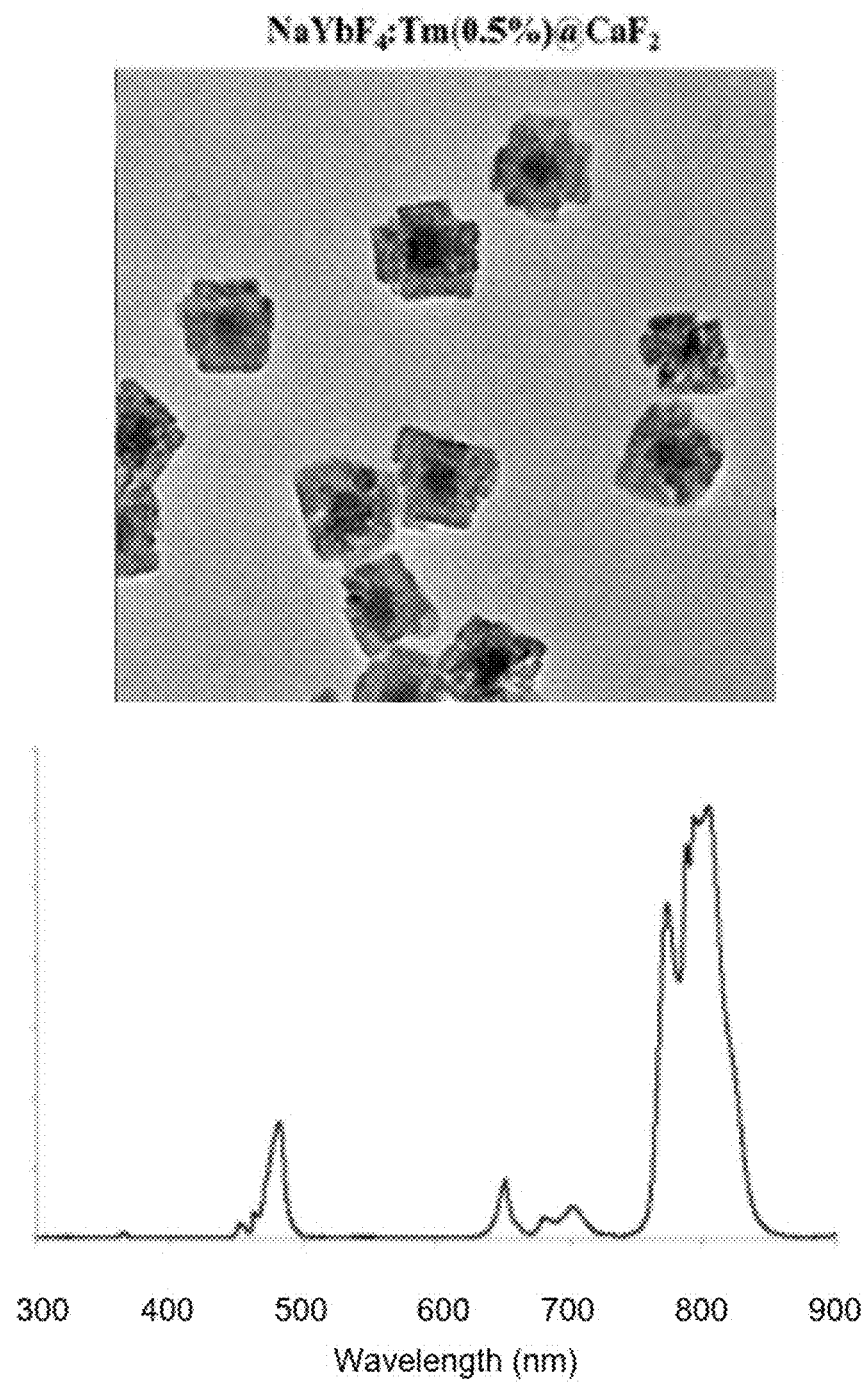
Figure 10:
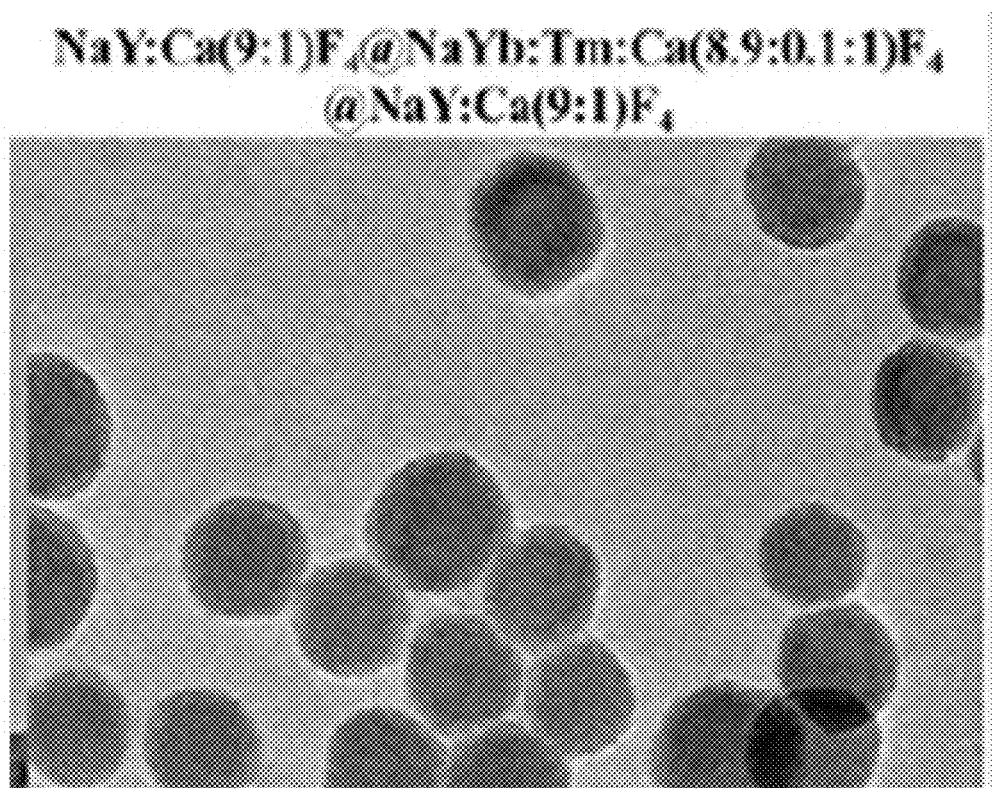
Figure 10:
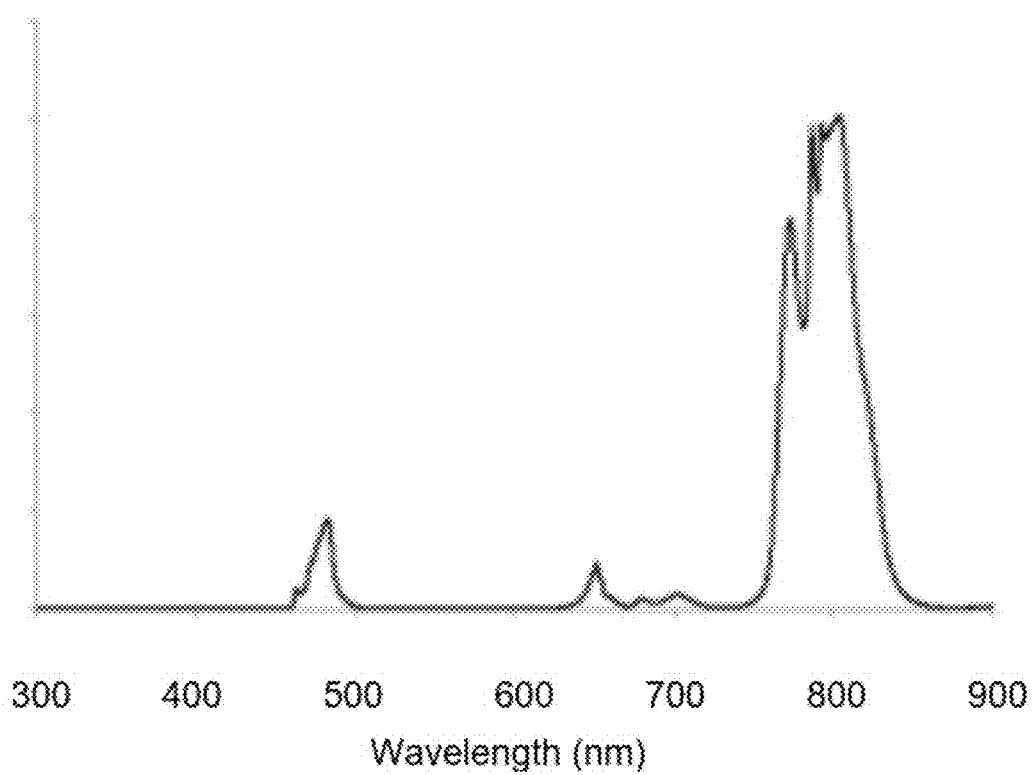

FIG. 10 shows the effect nanoparticle size and number of layers. In each of the examples shown in FIG. 10, the nanocrystal cores were doped with Tm dopants. Using calcium fluoride as the outermost, inert layer produced unique crystal formations on the active "core" of the nanoparticle. Co-doping an inert element (Ca or Y) throughout the core and shells helped create a uniform single crystal nanoparticle. The corresponding emission outputs are presented in the bottom traces in FIG. 10. The relative emission peaks (475 nm as reference peak) as a function of construction is readily apparent.

Example 3. Effects of Irradiating Upconverting Nanoparticles in Intraocular Lenses Example 3.1. Lens Doping for 980 nm Induced Shape Change Commercially available lens components (from RxSight) were modified to alternatively remove the UV absorbers from the casting components and to incorporate various upconverting core-shell nanocrystals. Where added, solid or wet nanocrystals were added directly to the lens mix with no modification. The resulting mixtures were centrifuged in a syringe to remove bubbles and then left for 24 hours in a −20° C. freezer. The lenses were then cast as a slab material or in a intraocular lens mold. Pressure was applied using a C-clamp and the lenses were put in a 37° C. oven for 48-72 hours. The resulting lenses or slabs were optically clear and free of bubbles. The lenses were used for subsequent irradiation studies.

Irradiation experiments consistent of using either a 365 nm source or 980 nm source. The 365 nm source delivered a clinical amount of power to induce shape change in the lens. The 980 nm source was focused using a 16-× magnification to generate powers of about 100 $W/cm^2$. Subsequent additional studies used powers around 20 $W/cm^2$ to induce shape change in the lens. Profilometer scans were taken before and after irradiation to see changes in the lens surface. The post irradiation images show distinct zones of shape change where the sample was irradiated. Earlier samples were irradiated with both 980 nm and 365 nm sources to show the material still behaved in a similar fashion when exposed to the 365 nm source, indicating the upconverting core-shell nanocrystals did not alter the material properties of the lens. Later sample irradiations had longer 980 nm irradiation times to show time dependence in induced shape change. Several variations of Tm-doped nanocrystals showed shape change in the lenses. Empty lenses (no particles in the material), un-doped particles in the lens ($NaYF_4$ or $NaYbF_4$), or mismatched doped particles ($NaYbF_4$:Ho(1%)—emission is green instead of UV) did not show shape change in the lenses under similar irradiation parameters. These controls strongly suggested that shape change was caused from the generated 365 nm emission form the Tm-doped core-shell nanocrystals, which in turn activates the photo-initiator in the lens material.

Example 3.2. Representative Results

Figure 11:
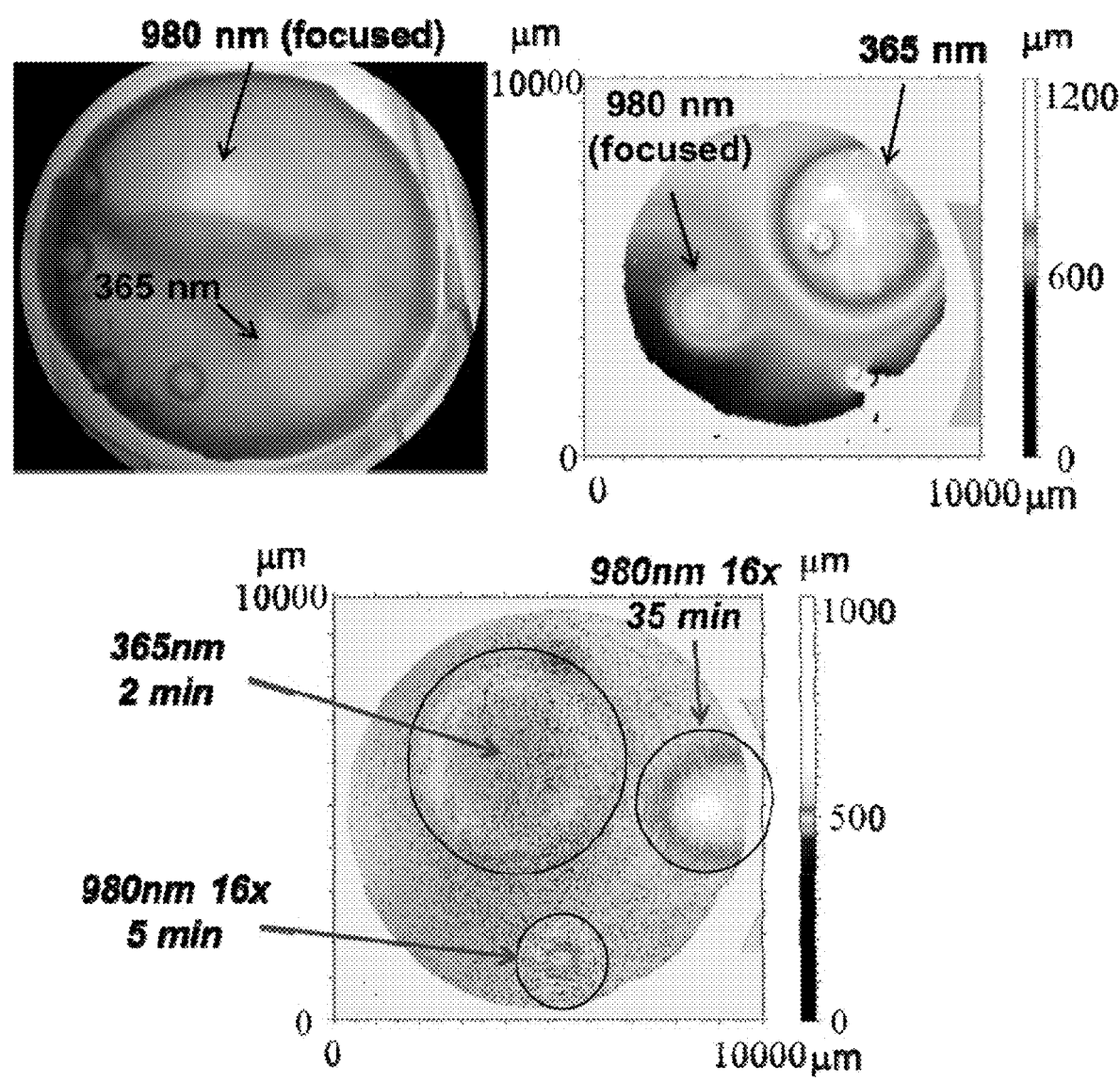
FIG. 11 compares the effect of irradiating an intraocular lens at both 365 nm and 980 nm.
Figure 12:
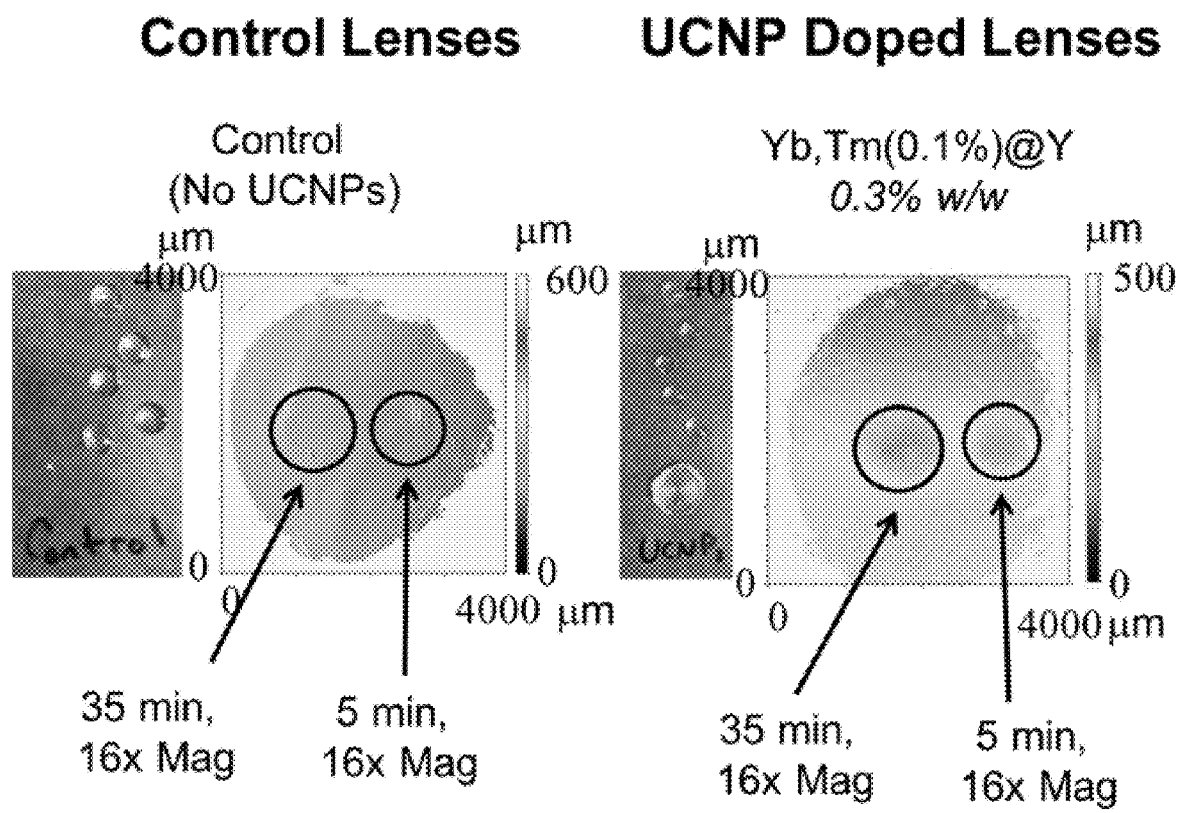
FIG. 12 shows the effect of irradiating an intraocular lens at 980 nm. In comparing a lens with no nanoparticles with a lens with the Tm-doped UCNPs, a shape change was only seen in the Tm-Doped UCNPs.
Figure 13:
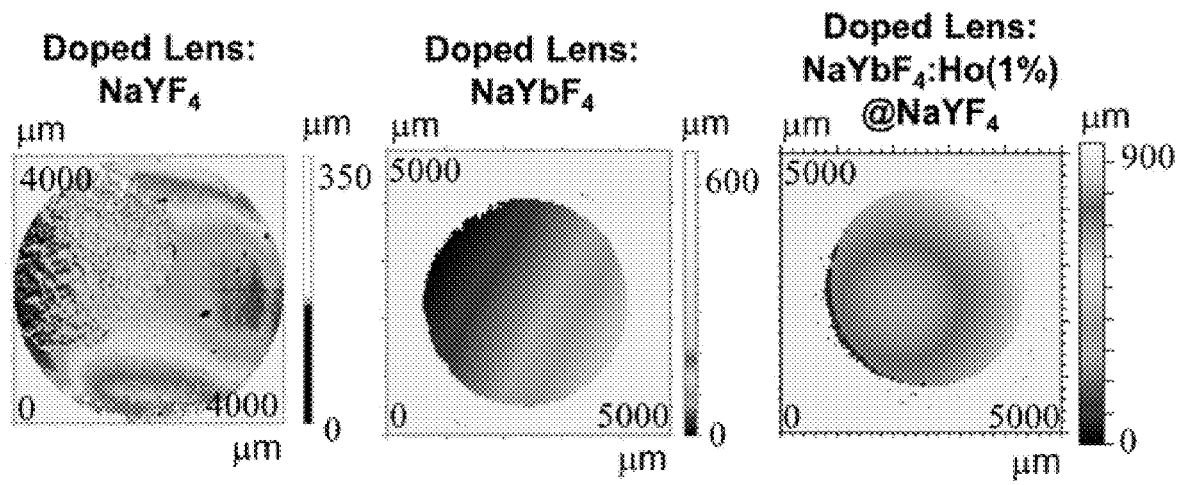
FIG. 13 shows the effect of doping nanocrystals on irradiated intraocular lenses.

Additional exemplary results are shown in FIGS. 11 to 13. In a first example, the UV-absorber component in the crosslinking mixture of a modified lens material (provided by RxSight) was removed and oleic acid coated Tm-upconverting core-shell nanocrystals were mixed into the blend. The material was casted as a slab and then cut to a circular shape to fit the cuvette holders for irradiation and analysis. The material was irradiated with both 365 nm and 980 nm sources. FIG. 11 shows shape change when exposed to both sources. The top two figures show the microscope visual identification of the shape change (left), while the right figure shows the shape change via the profilometer scan. The bottom figure contains a different synthesized set of UCNPs, which still respond in a similar manner. Exposing the sample to longer durations of the focused 980 nm light showed a larger shape change in the material.

In a similar set of experiments, the modified RxSight mixture (removal of absorbers and doped with core-shell nanocrystal) was subjected to casting as intraocular lenses. The left image in FIG. 12 shows a control sample (no nanocrystals) while the right figure contain lenses with the core-shell nanocrystals. Both produce optically clear lenses. The profilometer data showed that no shape change in the control lenses when exposed to the 980 nm light source while the doped lenses show shape change in the material that is exposure dependent.

Additional control lenses showed that shape changes were only induced in the material when the Tm-doped nanocrystals were included.

Additional studies confirmed the utility of the core-shell upconverting nanocrystals. Profilometer images shown in FIG. 13 were the difference where the before and after images were subtracted to generate a new image. The left sample of FIG. 13 contained undoped $NaYF_4$ particles, which did not absorb 980 nm light. The sample was rough because it was exposed to dust. However, no distinct change in the material was observed after irradiation. The middle sample of FIG. 14 was doped with $NaYbF_4$ particles containing Yb, a sensitizer which did absorb 980 nm, but the nanocrystal contained no emitter. No shape change associated with polymerization was seen. It is possible that the particle generated excessive heat during the absorption process and that could in turn initiate a polymerization reaction. But the absence of shape change post-irradiation suggested that the potential heat induced polymerization was not a concern. The right sample of FIG. 13 was made with a Ho-doped core-shell nanocrystal, which contained both an sensitizer and an emitter. But the emission bands did not overlap with the photo-initiator in the material. Here again, no shape change was seen post-irradiation. These tests are indicative of the need for there to be overlap between nanocrystal emissions and absorption by the photoinitiator (e.g., as with the 365 nm emission from the Fe-doped nanocrystals described above).

Such systems were also capable of polymer crosslinking, albeit with longer exposure times. From these studies, upconverting core-shell nanocrystals were shown to be able to serve as a practical method for initiating NIR-mediated photochemical polymerization and crosslinking. That is, the above observations demonstrated that the upconverting core-shell nanocrystals could be used to initiate polymerization using light having wavelengths in greater than 800 nm light and promote photochemistry that is normally carried out in the near UV, as in current light adjustable lens technology.

As those skilled in the art will appreciate, numerous modifications and variations of the present invention are possible in light of these teachings, and all such are contemplated hereby.

The disclosures of each patent, patent application, and publication cited or described in this document are hereby incorporated herein by reference, each in its entirety, for all purposes.

What is claimed:

1. A light adjustable intraocular lens comprising:
   (a) a photopolymerizable prepolymer;
   (b) a UV-Vis photoinitiator;
   (c) at least one upconverting core-shell nanocrystal; and
   (d) optionally a UV-Vis blocker;
   wherein the light adjustable intraocular lens further optionally comprises a polymer matrix in which the photopolymerizable prepolymer material, the UV-Vis photoinitiator, the optional UV-Vis blocker, and the at least one upconverting core-shell nanocrystal are distributed.

2. The light adjustable intraocular lens of claim 1, wherein the photopolymerizable prepolymer comprises a polyethylene glycol (PEG), a poly[alkyl or dialkyl]siloxane, a poly [meth]acrylate, a poly(amino acid), a poly(amino acid)-copolymer, a polycarbohydrate, a protein, or a polysaccharide backbone.

3. The light adjustable intraocular lens of claim 1, wherein the photopolymerizable prepolymer comprises an acrylate, methacrylate, acrylamide, methacrylamide, allyloxy, cinnamoyl, or vinyl group.

4. The light adjustable intraocular lens of claim 2, wherein the polysaccharide comprises poly(hyaluronic acid), dermatansulfate, chondroitinsulfate or keratansulfate.

5. The light adjustable intraocular lens of claim 2, wherein the protein is a native or engineered elastin.

6. The light adjustable intraocular lens of claim 1, wherein the photoinitiator is a Type I or a Type II photoinitiator.

7. The light adjustable intraocular lens of claim 1, wherein the photoinitiator absorbs light in a range of from 250 nm to 600 nm.

8. The light adjustable intraocular lens of claim 1, wherein the photoinitiator comprises an acetophenone, a benzophenone, a benzoin ether, a benzil ketal, an α-dialkoxyacetophenone, an alkylphenone, an α-hydroxyalkylphenone, an α-aminoalkylphenone, a xanthone, or a thioxanthone moiety.

9. The light adjustable intraocular lens of claim 1, wherein at least one type of upconverting core-shell nanocrystal comprises:
   (a) a nanocrystalline core comprising a lanthanide sensitizer capable of absorbing light in a range of from 780 nm to 1020 nm and having at least one emission peak in the range of from 250 nm to 500 nm;
   (b) at least one activating shell superposed on the nanocrystalline core, the shell comprising at least one lanthanide activator; and
   (c) an optically inert outer layer superposed over the at least one activating shell.

10. The light adjustable intraocular lens of claim 9, wherein the nanocrystalline core comprises one or more of Er, Fe, Gd, Ho, Tm, Y, or Yb.

11. The light adjustable intraocular lens of claim 9, wherein the nanocrystalline core comprises Tm, Er, Fe, or combination thereof.

12. The light adjustable intraocular lens of claim 9, wherein the nanocrystalline core comprises a $NaGdF_4$, $NaLuF_4$, $LiYF_4$, $NaYF_4$, $KYF_4$, $KYb_2F_7$, $BaF_2$, $CaF_2$, $SrF_2$, $LaF_3$, $YF_3$, $BaYF_5$, $BaGdF_5$, $KY_3F_{10}$, YOF, LuOF, or GdOF host doped with one or more of Er, Fe, Gd, Ho, Tm, Y, or Yb.

13. The light adjustable intraocular lens of claim 9, wherein the nanocrystalline core comprises a host doped with one or more of (i) Er or Tm and (ii) Yb ($NaYF_4$:Yb, Er/Tm).

14. The light adjustable intraocular lens of claim 9, wherein the at least one lanthanide activator comprises Gd, Nd, or Yb.

15. The light adjustable intraocular lens of claim 9, wherein the optically inert outer layer comprises yttrium, a $C_{6-24}$ saturated or unsaturated fatty acid, an optionally functionalized silicate polymer coating, or an alkali metal fluoride or alkaline earth metal fluoride.

16. The light adjustable intraocular lens of claim 1, wherein the at least one type of upconverting core-shell nanocrystal line core is a hexagonal platelet.

17. The light adjustable intraocular lens of claim 1, wherein at least one shell of the at least one type of upconverting core-shell nanocrystal line contains Nd.

18. The light adjustable intraocular lens of claim 1, wherein a portion of the at least one type of upconverting core-shell nanocrystal is surface modified to present an amino, carboxylic acid, hydroxy, or thiol group, or a combination thereof.

19. The light adjustable intraocular lens of claim 1, further comprising the polymer matrix in which the photopolymerizable prepolymer material, the UV-Vis photoinitiator, the optional UV-Vis blocker, and the at least one upconverting core-shell nanocrystal are distributed.

20. The light adjustable intraocular lens of claim 1, further comprising a UV blocking front and/or back layer.

21. A method of adjusting the optical properties of the light adjustable intraocular lens of claim 1, the method comprising irradiating the light adjustable intraocular lens with a near infrared wavelength of light, wherein the irradiation of the light adjustable lens results in a change in a refractive property of the light adjustable intraocular lens.

22. The method of claim 21, wherein the near infrared wavelength of light is applied with a laser.

23. The method of claim 21, wherein the near infrared wavelength of light is in a range of from 780 nm to 1020 nm.

24. The method of claim 21, wherein the light adjustable intraocular lens is implanted in an eye of a patient prior to irradiation.

25. The method of claim 21, wherein the refractive property of the light adjustable intraocular lens is refractive index, distribution of fluid, shape, or local or total density, or two or more of these properties of the light adjustable intraocular lens.

* * * * *